US007311912B1

(12) United States Patent
Hein et al.

(10) Patent No.: US 7,311,912 B1
(45) **Date of Patent: *Dec. 25, 2007**

(54) EPITHELIAL TISSUE TARGETING AGENT

(75) Inventors: Mich B. Hein, Fallbrook, CA (US); Andrew C. Hiatt, San Diego, CA (US); John H. Fitchen, La Jolla, CA (US)

(73) Assignee: Plantbodies Corporation, Pittsboro, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/005,318

(22) Filed: Jan. 9, 1998

Related U.S. Application Data

(63) Continuation-in-part of application No. 08/782,481, filed on Jan. 10, 1997.

(51) Int. Cl.

| | |
|---|---|
| *A61K 39/395* | (2006.01) |
| *A61K 38/16* | (2006.01) |
| *C07K 16/46* | (2006.01) |
| *C07K 19/00* | (2006.01) |

(52) U.S. Cl. .................. 424/134.1; 424/804; 424/806; 514/12; 530/300; 530/387.3; 530/861; 530/863

(58) Field of Classification Search ............ 424/133.1, 424/134.1, 198.1, 192.1, 193.1, 195.11; 530/350, 530/387.3, 391.7

See application file for complete search history.

(56) References Cited

U.S. PATENT DOCUMENTS

| | | | | |
|---|---|---|---|---|
| 4,350,764 | A * | 9/1982 | Baxter et al. | 435/69.4 |
| 4,897,384 | A * | 1/1990 | Janoff et al. | 514/34 |
| 5,169,627 | A | 12/1992 | Cunningham-Rundles | 424/85.91 |
| 5,202,422 | A | 4/1993 | Hiatt et al. | 530/387.3 |
| 5,254,342 | A * | 10/1993 | Shen et al. | 424/401 |
| 5,284,931 | A | 2/1994 | Springer et al. | 424/85.8 |
| 5,366,958 | A * | 11/1994 | Weiner et al. | 514/2 |
| 5,639,947 | A | 6/1997 | Hiatt et al. | 800/205 |
| 5,670,626 | A | 9/1997 | Chang | 530/388.5 |
| 5,814,507 | A * | 9/1998 | Cheng et al. | 435/196 |
| 6,063,905 | A | 5/2000 | Capra et al. | |

FOREIGN PATENT DOCUMENTS

| | | |
|---|---|---|
| JP | 58-134032 | 8/1983 |
| WO | WO 92/16622 | * 10/1992 |

OTHER PUBLICATIONS

Creighton TE. (1984) Proteins: Structures and Molecular Properties. W.H. Freeman, New York, p. 2.*
Weissleder et al. Quantitation of slow drug release from an implantable and degradable gentamicin conjugate by in vivo magnetic resonance imaging. Antimicrob Agents Chemother Apr. 1995;39(4):839-45.*
Bowie et al. Deciphering the message in protein sequences: tolerance to amino acid substitutions. Science, (Mar. 16, 1990) 247 (4948) 1306-10.*
Ngo et al., in The Protein Folding Problem and Tertiary Structure Prediction, Merz and Le Grand (Eds), Aug. 1994, Springer Verlag, pp. 433 and 492-495.*
Pierce Chemical Company. ImmunoTechnology Catalog and Handbook. 1992-93, pp. E-8, E-15, E-21, E-58.*
Carayannopoulos et al. Recombinant human IgA expressed in insect cells. Proc Natl Acad Sci U S A. Aug. 30, 1994;91(18):8348-52.*
Carayannopoulos et al. Localization of the binding site for the monocyte immunoglobulin (Ig) A-Fc receptor (CD89) to the domain boundary between Calpha2 and Calpha3 in human IgA1. J Exp Med Apr. 1, 1996;183(4):1579-86.*
Morton et al. Purification and characterization of chimeric human IgA1 and IgA2 expressed in COS and Chinese hamster ovary cells. J Immunol Nov. 1, 1993;151(9):4743-52.*
Lemaitre-Coelho et al. In vivo experiments involving secretory component in the rat hepatic transfer of polymeric IgA. Immunology Jun. 1981;43(2):261-70.*
Koshland ME. The coming of age of the immunoglobulin J chain. Annu Rev Immunol. 1985;3:425-53.*
Brandtzaeg et al. Intestinal secretion of IgA and IgM: a hypothetical model. Ciba Found Symp. Apr. 26-28, 1977;(46):77-113.*
Brandtzaeg P. Blocking effect of J chain and J-chain antibody on the binding of secretory component to human IgA and IgM. Scand J. Immunol. 1975;4(8):837-42.*
Bowie et al. Deciphering the message in protein sequences: tolerance to amino acid substitutions. Science, (Mar. 16, 1990) 247 (4948) 1306-10.*
Ngo et al., in The Protein Folding Problem and Tertiary Structure Prediction, Merz and Le Grand (Eds), Aug. 1994, Springer Verlag, pp. 433 and 492-495.*

Marston FA. The purification of eukaryotic polypeptides synthesized in *Escherichia coli*. Biochem J. Nov. 15, 1986;240(1):1-12.*

Janknecht et al. Affinity purification of histidine-tagged proteins transiently produced in HeLa cells. Gene. Nov. 16, 1992;121(2):321-4.*
Chamow SM, Ashkenazi A. Immunoadhesins: principles and applications. Trends Biotechnol. Feb. 1996;14(2):52-60.*
Martin et al. Efficient neutralization and disruption of rhinovirus by chimeric ICAM-1/immunoglobulin molecules. J Virol. Jun. 1993;67(6):3561-8.*

Ferkol et al., "Gene Transfer into Respiratory Epithelial Cells by Targeting the Polymeric Immunoglobulin Receptor," *J. Clin. Invest. 92*: 2394-2400, 1993.

Terskikh et al., "Dimeric Recombinant IgA Directed Against Carcino-Embryonic Antigen, A Novel Tool For Carcinoma Localization," *Molecular Immunology 31*(17): 1313-1319, 1994.

Hendrickson et al., "Altered Hepatic Transport of Immunoglobulin A in Mice Lacking the J Chain," *J. Exp. Med. 182*: 1905-1911, 1995.
Max and Korsmeyer, "Human J Chain Gene. Structure and Expression in B Lymphoid Cells," *Journal of Experimental Medicine 161*: 832-849, 1985.

(Continued)

*Primary Examiner*—David S. Romeo
(74) *Attorney, Agent, or Firm*—Alston & Bird LLP

(57) ABSTRACT

Targeting molecules for use in delivering biological agents to epithelial tissue are disclosed. Upon delivery, the biological agent(s) may remain within an epithelial cell or may undergo transepithelial transport via transcytosis. The targeting molecules may be used, for example, for the delivery of therapeutic agents.

17 Claims, 1 Drawing Sheet

OTHER PUBLICATIONS

Frutiger et al., "Disulfide Bond Assignment in Human J Chain and Its Covalent Pairing with Immunoglobulin M," *Biochemistry 31*: 12643-12647, 1992.

Allen et al., "An immunoperoxidase study of epithelial marker antigens in ulcerative colitis with dysplasia and carcinoma," *J. Clin. Pathol. 38*: 18-29, 1985.

Brown and Koshland, "Evidence for a long-range conformational change induced by antigen binding to IgM antibody," *Proc. Natl. Acad. Sci. USA 74*(12): 5682-5686, 1977.

Brandtzaeg and Baklien, "Immunohistochemical studies of the immunoglobulin-producing cell systems of the human intestinal mucosa," *Acta Histochemica Suppl. 21*: 105-119, 1980.

Burns et al., "Protective Effect of Rotavirus VP6-Specific IgA Monoclonal Antibodies That Lack Neutralizing Activity," *Science 272*: 104-107, 1996.

Emancipator and Lamm, "IgA Nephropathy: Overproduction of Decreased Clearance of Immune Complexes?" *Laboratory Investigation 61*(4): 365-367, 1989.

Kaetzel et al., "Epithelial Transcytosis of Monomeric IgA and IgG Cross-linked Through Antigen to Polymeric IgA. A Role for Monomeric Antibodies in the Mucosal Immune System," *Journal of Immunology 152*: 72-76, 1994.

Kaetzel et al., "The polymeric immunoglobulin receptor (secretory component) mediates transport of immune complexes across epithelial cells: A local defense function for IgA," *Proc. Natl. Acad. Sci. 88*: 8796-8800, 1991.

Kulseth and Rogne, "Cloning and Characterization of the Bovine Immunoglobulin J Chain cDNA and Its Promoter Region," *DNA and Cell Biology 13*(1): 37-42, 1994.

Mannik and Arend, "Fate of Preformed Immune Complexes in Rabbits and Rhesus Monkeys," *Journal of Experimental Medicine 134*(3 pt. 2): 19s-31s, 1971.

Mazanec et al., "Intracellular Neutralization of Influenza Virus by Immunoglobulin A Anti-Hemagglutinin Monoclonal Antibodies," *Journal of Virology 69*(2): 1339-1343, 1995.

Mestecky et al., "The Role of the Liver in Catabolism of Mouse and Human IgA," *Immunological Investigations 18*(1-4): 313-324, 1989.

Nagura et al., "Translocation of Dimeric IgA Through Neoplastic Colon Cells In Vitro," *Journal of Immunology 123*(5): 2359-2368, 1979.

Rifai and Mannik, "Clearance Kinetics and Fate of Mouse IgA Immune Complexes Prepared with Monomeric or Dimeric IgA," *Journal of Immunology 130*(4): 1826-1832, 1983.

Rifai et al., "Clearance Kinetics and Fate of Macromolecular IgA in Patients with IgA Nephropathy," *Laboratory Investigation 61*(4): 381-388, 1989.

Sheldrake et al., "Selective Transport of Serum-Derived IgA Into Mucosal Secretions," *Journal of Immunology 132*(1): 363-368, 1984.

Verma and Somia, "Gene therapy—promises, problems and prospects," *Nature 389*: 239-242, 1997.

Wells, James A., "Perspectives in Biochemistry. Additivity of Mutational Effects in Proteins," *Biochemistry 29*(37): 8509-8517, 1990.

Youngman et al., "Inhibition of IFN-$\gamma$ Activity in Supernatants from Stimulated Human Intestinal Mononuclear Cells Prevents Up-Regulation of the Polymeric Ig Receptor in an Intestinal Epithelial Cell Line," *Journal of Immunology 153*: 675-681, 1994.

Hexham, J., et al., "A Human Immunoglobulin (Ig)A C$\alpha$3 Domain Motif Directs Polymeric Ig Receptor-Mediated Secretion," *J. Exp. Med.*, 1999, pp. 747-751, vol. 189(4), The Rockefeller University Press.

Johansen, F., et al., "The J Chain is Essential for Polymeric Ig Receptor-Mediated Epithelial Transport of IgA," *Journal of Immunology*, 2001, pp. 5185-5192, The American Association of Immunologists.

Vaerman, J., et al., "Antibody Against the Human J Chain Inhibits Polymeric Ig Receptor-Mediated Biliary and Epithelial Transport of Human Polymeric IgA," *Eur. J. Immunol.*, 1998, pp. 171-182, vol. 28, WILEY-VCH Verlag GmbH, Weinheim, Germany.

White, K.D. and J.D. Capra, "Targeting Mucosal Sites by Polymeric Immunoglobulin Receptor-Directed Peptides," *J. Exp. Med.*, 2002, pp. 551-555, vol. 196(4), The Rockefeller University Press.

\* cited by examiner

SEQUENCE COMPARISON OF J CHAIN PROTEINS AND DEDUCED J CHAIN SEQUENCES
FROM SIX ORGANISMS

```
          10        20        30        40        50        60
-1--------X---------X---------X---------X---------X---------X
QEDERIVLVDNKCKCARITSRIIRSSEDPNEDIVERNIRIIVPLNNRENISDPTSPLRTRF
-DENERIV---------------P-A---SQ------V--------S----------M--K-
D--ATI-A----M-T-V-----P-T--------------V-----------------RN-
---ST--------Q-V--------DPDN-S----------------T------------E-
 EQEYI-AN------VK-S--FVP-T-R-G-E-L----Q-TI-TSS-MX----Y-----Q-
        ---M-T-V-A--RGTR----------Y---N---K--G----------NQ- 70        80        90       100       110       120
---------X---------X---------X---------X---------X---------X
VYHLSDLCKKCDPTEVELDNQIVTATQSNICDEDSAT ETCYTY    DRNKCYTAVVPL
---------------T-----ED-V---S------S-A ------   -------NR-K-
------V------V----ED-V---------N--DGVP----M-    -------TM---
K-N-AN----------I-----VF--S-----PD-DYS ------   -------TL--I
--N-W-I-Q----VQL-IGGIP-L-S-PXXSKP-dE            ---TE-NF
-----PS------   YEDGV----ET---YP-QGVPQS-RD-CPEL-------VL--P 130       140
---------X---------X---------X---
VYGGETKMVETALTPDACYPD              HUMAN
S-R-Q-----------S----              BOVINE
R-H------QA-----S----              MOUSE
THR-V-R--KAT----S----              RABBIT
K        KKVP----S--EYSE           BULL FROG
G-T------QN----------              EARTH WORM
```

*Fig. 1*

```
                         SEQUENCE LISTING

<160> NUMBER OF SEQ ID NOS: 140

<210> SEQ ID NO 1
<211> LENGTH: 137
<212> TYPE: PRT
<213> ORGANISM: Homo sapiens

<400> SEQUENCE: 1

Gln Glu Asp Glu Arg Ile Val Leu Val Asp Asn Lys Cys Lys Cys Ala
 1               5                  10                  15

Arg Ile Thr Ser Arg Ile Ile Arg Ser Ser Glu Asp Pro Asn Glu Asp
             20                  25                  30

Ile Val Glu Arg Asn Ile Arg Ile Ile Val Pro Leu Asn Asn Arg Glu
         35                  40                  45

Asn Ile Ser Asp Pro Thr Ser Pro Leu Arg Thr Arg Pro Val Tyr His
     50                  55                  60

Leu Ser Asp Leu Cys Lys Lys Cys Asp Pro Thr Glu Val Glu Leu Asp
 65                  70                  75                  80

Asn Gln Ile Val Thr Ala Thr Gln Ser Asn Ile Cys Asp Glu Asp Ser
                 85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
    130                 135

<210> SEQ ID NO 2
<211> LENGTH: 135
<212> TYPE: PRT
<213> ORGANISM: Mus sp.

<400> SEQUENCE: 2

Gln Asp Glu Asn Glu Arg Ile Val Val Asp Asn Lys Cys Lys Cys Ala
 1               5                  10                  15

Arg Ile Thr Ser Arg Ile Ile Pro Ser Ala Glu Asp Pro Ser Gln Asp
             20                  25                  30

Ile Val Glu Arg Asn Val Arg Ile Ile Val Pro Leu Asn Ser Arg Glu
         35                  40                  45

Asn Ile Ser Asp Pro Thr Ser Pro Met Arg Thr Lys Pro Val Tyr His
     50                  55                  60

Leu Ser Asp Leu Cys Lys Lys Cys Asp Thr Thr Glu Val Glu Leu Glu
 65                  70                  75                  80

Asp Gln Val Val Thr Ala Ser Gln Ser Asn Ile Cys Asp Ser Asp Ala
                 85                  90                  95

Glu Thr Cys Tyr Thr Tyr Asp Arg Asn Lys Cys Tyr Thr Asn Arg Val
            100                 105                 110

Lys Leu Ser Tyr Arg Gly Gln Thr Lys Met Val Glu Thr Ala Leu Thr
        115                 120                 125
```

Pro Asp Ser Cys Tyr Pro Asp
        130                 135

<210> SEQ ID NO 3
<211> LENGTH: 137
<212> TYPE: PRT
<213> ORGANISM: Oryctolagus cuniculus

<400> SEQUENCE: 3

Asp Asp Glu Ala Thr Ile Leu Ala Asp Asn Lys Cys Met Cys Thr Arg
 1               5                  10                  15

Val Thr Ser Arg Ile Ile Pro Ser Thr Glu Asp Pro Asn Glu Asp Ile
                20                  25                  30

Val Glu Arg Asn Ile Arg Ile Val Pro Leu Asn Asn Arg Glu Asn
            35                  40                  45

Ile Ser Asp Pro Thr Ser Pro Leu Arg Arg Asn Pro Val Tyr His Leu
     50                  55                  60

Ser Asp Val Cys Lys Lys Cys Asp Pro Val Glu Val Glu Leu Glu Asp
 65                  70                  75                  80

Gln Val Val Thr Ala Thr Gln Ser Asn Ile Cys Asn Glu Asp Asp Gly
                85                  90                  95

Val Pro Glu Thr Cys Tyr Met Tyr Asp Arg Asn Lys Cys Tyr Thr Thr
            100                 105                 110

Met Val Pro Leu Arg Tyr His Gly Glu Thr Lys Met Val Gln Ala Ala
        115                 120                 125

Leu Thr Pro Asp Ser Cys Tyr Pro Asp
        130                 135

<210> SEQ ID NO 4
<211> LENGTH: 136
<212> TYPE: PRT
<213> ORGANISM: Bos sp.

<400> SEQUENCE: 4

Glu Asp Glu Ser Thr Val Leu Val Asp Asn Lys Cys Gln Cys Val Arg
 1               5                  10                  15

Ile Thr Ser Arg Ile Ile Arg Asp Pro Asp Asn Pro Ser Glu Asp Ile
                20                  25                  30

Val Glu Arg Asn Ile Arg Ile Ile Val Pro Leu Asn Thr Arg Glu Asn
            35                  40                  45

Ile Ser Asp Pro Thr Ser Pro Leu Arg Thr Glu Pro Lys Tyr Asn Leu
     50                  55                  60

Ala Asn Leu Cys Lys Lys Cys Asp Pro Thr Glu Ile Glu Leu Asp Asn
 65                  70                  75                  80

Gln Val Phe Thr Ala Ser Gln Ser Asn Ile Cys Pro Asp Asp Tyr
                85                  90                  95

Ser Glu Thr Cys Tyr Thr Tyr Asp Arg Asn Lys Cys Tyr Thr Thr Leu
            100                 105                 110

Val Pro Ile Thr His Arg Gly Val Thr Arg Met Val Lys Ala Thr Leu
        115                 120                 125

Thr Pro Asp Ser Cys Tyr Pro Asp
        130                 135

<210> SEQ ID NO 5
<211> LENGTH: 119
<212> TYPE: PRT
<213> ORGANISM: Rana sp.

```
<220> FEATURE:
<221> NAME/KEY: MOD_RES
<222> LOCATION: (47)
<223> OTHER INFORMATION: Variable amino acid
<220> FEATURE:
<221> NAME/KEY: MOD_RES
<222> LOCATION: (88)..(89)
<223> OTHER INFORMATION: Variable amino acid
<220> FEATURE:
<221> NAME/KEY: MOD_RES
<222> LOCATION: (91)
<223> OTHER INFORMATION: Variable amino acid

<400> SEQUENCE: 5

Glu Gln Glu Tyr Ile Leu Ala Asn Asn Lys Cys Lys Cys Val Lys Ile
 1               5                  10                  15

Ser Ser Arg Phe Val Pro Ser Thr Glu Arg Pro Gly Glu Glu Ile Leu
             20                  25                  30

Glu Arg Asn Ile Gln Ile Thr Ile Pro Thr Ser Ser Arg Met Xaa Ile
         35                  40                  45

Ser Asp Pro Tyr Ser Pro Leu Arg Thr Gln Pro Val Tyr Asn Leu Trp
     50                  55                  60

Asp Ile Cys Gln Lys Cys Asp Pro Val Gln Leu Glu Ile Gly Gly Ile
 65                  70                  75                  80

Pro Val Leu Ala Ser Gln Pro Xaa Xaa Ser Xaa Pro Asp Asp Glu Cys
                 85                  90                  95

Tyr Thr Thr Glu Val Asn Phe Lys Lys Lys Val Pro Leu Thr Pro Asp
            100                 105                 110

Ser Cys Tyr Glu Tyr Ser Glu
        115

<210> SEQ ID NO 6
<211> LENGTH: 128
<212> TYPE: PRT
<213> ORGANISM: Lumbricus sp.

<400> SEQUENCE: 6

Asn Lys Cys Met Cys Thr Arg Val Thr Ala Arg Ile Arg Gly Thr Arg
 1               5                  10                  15

Glu Asp Pro Asn Glu Asp Ile Val Glu Arg Tyr Ile Arg Ile Asn Val
             20                  25                  30

Pro Leu Lys Asn Arg Gly Asn Ile Ser Asp Pro Thr Ser Pro Leu Arg
         35                  40                  45

Asn Gln Pro Val Tyr His Leu Ser Pro Ser Cys Lys Lys Cys Asp Pro
     50                  55                  60

Tyr Glu Asp Gly Val Val Thr Ala Thr Glu Thr Asn Ile Cys Tyr Pro
 65                  70                  75                  80

Asp Gln Gly Val Pro Gln Ser Cys Arg Asp Tyr Cys Pro Glu Leu Asp
                 85                  90                  95

Arg Asn Lys Cys Tyr Thr Val Leu Val Pro Pro Gly Tyr Thr Gly Glu
            100                 105                 110

Thr Lys Met Val Gln Asn Ala Leu Thr Pro Asp Ala Cys Tyr Pro Asp
        115                 120                 125

<210> SEQ ID NO 7
<211> LENGTH: 421
<212> TYPE: DNA
<213> ORGANISM: Homo sapiens
<220> FEATURE:
<221> NAME/KEY: CDS
<222> LOCATION: (1)..(414)
```

```
<220> FEATURE:
<221> NAME/KEY: sig_peptide
<222> LOCATION: (1)..(6)
<220> FEATURE:
<221> NAME/KEY: mat_peptide
<222> LOCATION: (7)..(414)

<400> SEQUENCE: 7 gat cag gaa gat gaa cgt att gtt ctg gtt gac aac aag tgc aag tgt      48
Asp Gln Glu Asp Glu Arg Ile Val Leu Val Asp Asn Lys Cys Lys Cys
     -1   1               5                  10 gct cgt att act tct aga atc atc cgt agc tca gag gac cca aat gaa      96
Ala Arg Ile Thr Ser Arg Ile Ile Arg Ser Ser Glu Asp Pro Asn Glu
 15                  20                  25                  30 gat ata gtc gaa cgt aac atc cgt atc atc gtc cca ctg aat aac cgg     144
Asp Ile Val Glu Arg Asn Ile Arg Ile Ile Val Pro Leu Asn Asn Arg
                 35                  40                  45 gag aat atc tca gat cct aca agt ccg ttg cgc aca cgc ttc gta tac     192
Glu Asn Ile Ser Asp Pro Thr Ser Pro Leu Arg Thr Arg Phe Val Tyr
         50                  55                  60 cac ctg tca gat ctg tgt aag aag tgt gat cca aca gag gta gag ctg     240
His Leu Ser Asp Leu Cys Lys Lys Cys Asp Pro Thr Glu Val Glu Leu
     65                  70                  75 gac aat cag ata gtc act gcg act caa agc aac att tgc gat gag gac     288
Asp Asn Gln Ile Val Thr Ala Thr Gln Ser Asn Ile Cys Asp Glu Asp
 80                  85                  90 agc gct aca gaa acc tgc agc acc tac gat agg aac aaa tgc tac acg     336
Ser Ala Thr Glu Thr Cys Ser Thr Tyr Asp Arg Asn Lys Cys Tyr Thr
 95                 100                 105                 110 gcc gtg gtt ccg ctc gtg tat ggt gga gag aca aaa atg gtg gaa act     384
Ala Val Val Pro Leu Val Tyr Gly Gly Glu Thr Lys Met Val Glu Thr
                115                 120                 125 gcc ctt acg ccc gat gca tgc tat ccg gac tgaattc                     421
Ala Leu Thr Pro Asp Ala Cys Tyr Pro Asp
                130                 135

<210> SEQ ID NO 8
<211> LENGTH: 215
<212> TYPE: DNA
<213> ORGANISM: Homo sapiens
<220> FEATURE:
<221> NAME/KEY: CDS
<222> LOCATION: (1)..(213)

<400> SEQUENCE: 8 gat cag aag tgc aag tgt gct cgt att act tct aga atc atc cgt agc      48
Asp Gln Lys Cys Lys Cys Ala Arg Ile Thr Ser Arg Ile Ile Arg Ser
  1               5                  10                  15 tca gag gac cca aat gaa gat ata gtc gaa cgt aac atc cgt atc atc      96
Ser Glu Asp Pro Asn Glu Asp Ile Val Glu Arg Asn Ile Arg Ile Ile
                 20                  25                  30 gtc cca ctg aat aac cgg gag aat atc tca gat cct aca agt ccg ttg     144
Val Pro Leu Asn Asn Arg Glu Asn Ile Ser Asp Pro Thr Ser Pro Leu
         35                  40                  45 cgc aca cgc ttc gta tac cac ctg tca gat ctg tgt aag aag gat gag     192
Arg Thr Arg Phe Val Tyr His Leu Ser Asp Leu Cys Lys Lys Asp Glu
     50                  55                  60 gac agc gct aca gaa acc tgc tg                                      215
Asp Ser Ala Thr Glu Thr Cys
 65                  70

<210> SEQ ID NO 9
<211> LENGTH: 140
```

```
<212> TYPE: DNA
<213> ORGANISM: Homo sapiens

<400> SEQUENCE: 9
ctagaatcat ccgtagctca gaggacccaa atgaagatat agtcgaacgt aacatccgta      60
tcatcgtccc actgaataac cgggagaata tctcagatcc tacaagtccg ttgcgcacac     120
gcttcgtata ccacctgtca                                                 140

<210> SEQ ID NO 10
<211> LENGTH: 31
<212> TYPE: DNA
<213> ORGANISM: Homo sapiens

<400> SEQUENCE: 10
gatcagaagt gcaagtgtgc tcgtattact t                                     31

<210> SEQ ID NO 11
<211> LENGTH: 44
<212> TYPE: DNA
<213> ORGANISM: Homo sapiens
<220> FEATURE:
<221> NAME/KEY: CDS
<222> LOCATION: (1)..(42)

<400> SEQUENCE: 11 gat ctg tgt aag aag gat gaa gat tcc gct aca gaa acc tgc tg             44
Asp Leu Cys Lys Lys Asp Glu Asp Ser Ala Thr Glu Thr Cys
 1               5                  10

<210> SEQ ID NO 12
<211> LENGTH: 109
<212> TYPE: DNA
<213> ORGANISM: Homo sapiens

<400> SEQUENCE: 12
gcacctacga taggaacaaa tgctacacgg ccgtggttcc gctcgtgtat ggtggagaga      60
caaaaatggt ggaaactgcc cttacgcccg atgcatgcta ccctgactg                 109

<210> SEQ ID NO 13
<211> LENGTH: 286
<212> TYPE: DNA
<213> ORGANISM: Homo  sapiens
<220> FEATURE:
<221> NAME/KEY: CDS
<222> LOCATION: (1)...(282)

<400> SEQUENCE: 13 gac aac aag tgc aag tgt gct cgt att act tct aga atc atc cgt agc        48
Asp Asn Lys Cys Lys Cys Ala Arg Ile Thr Ser Arg Ile Ile Arg Ser
 1               5                  10                  15 tca gag gac cca aat gaa gat ata gtc gaa cgt aac atc cgt atc atc        96
Ser Glu Asp Pro Asn Glu Asp Ile Val Glu Arg Asn Ile Arg Ile Ile
                20                  25                  30 gtc cca ctg aat aac cgg gag aat atc tca gat cct aca agt ccg ttg       144
Val Pro Leu Asn Asn Arg Glu Asn Ile Ser Asp Pro Thr Ser Pro Leu
            35                  40                  45 cgc aca cgc ttc gta tac cac ctg tca gat ctg tgt aag aag tgt gat       192
Arg Thr Arg Phe Val Tyr His Leu Ser Asp Leu Cys Lys Lys Cys Asp
        50                  55                  60 cca aca gag gta gag ctg gac aat cag ata gtc act gcg act caa agc       240
Pro Thr Glu Val Glu Leu Asp Asn Gln Ile Val Thr Ala Thr Gln Ser
65                  70                  75                  80
```

-continued

```
aac att tgc gat gag gac agc gct aca gaa acc tgc tac tga                282
Asn Ile Cys Asp Glu Asp Ser Ala Thr Glu Thr Cys Tyr  *
                 85                  90 attc                                                                    286
```

<210> SEQ ID NO 14
<211> LENGTH: 105
<212> TYPE: DNA
<213> ORGANISM: Homo sapiens
<220> FEATURE:
<221> NAME/KEY: CDS
<222> LOCATION: (1)..(105)

<400> SEQUENCE: 14

```
gat ctg tgt aag aag tgt gat cca aca gag gta gag ctg gac aat cag         48
Asp Leu Cys Lys Lys Cys Asp Pro Thr Glu Val Glu Leu Asp Asn Gln
 1               5                  10                  15 ata gtc act gcg act caa agc aac att tgc gat gag gac agc gct aca         96
Ile Val Thr Ala Thr Gln Ser Asn Ile Cys Asp Glu Asp Ser Ala Thr
             20                  25                  30 gaa acc tgc                                                             105
Glu Thr Cys
         35
```

<210> SEQ ID NO 15
<211> LENGTH: 61
<212> TYPE: DNA
<213> ORGANISM: Homo sapiens

<400> SEQUENCE: 15

```
gatcaggaag atgaacgtat tgttctggtt gacaacaagt gcaagtgtgc tcgtattact       60
t                                                                       61
```

<210> SEQ ID NO 16
<211> LENGTH: 198
<212> TYPE: DNA
<213> ORGANISM: Homo sapiens

<400> SEQUENCE: 16

```
gcgatgacga cgataaggcc caaacggaga cctgtactgt tgcgcctcgt gaacggcaaa       60
actgcggatt cccgggagta acaccctctc agtgcgctaa taaggctgc tgttttgatg       120 acacggtacg gggcgttccg tggtgcttct accccaatac aattgacgtt ccgcctgaag      180
aagagtgcga gttttaag                                                    198
```

<210> SEQ ID NO 17
<211> LENGTH: 138
<212> TYPE: PRT
<213> ORGANISM: Homo sapiens

<400> SEQUENCE: 17

```
Asp Gln Glu Asp Glu Arg Ile Val Leu Val Asp Asn Lys Cys Lys Cys
 -1  1               5                  10

Ala Arg Ile Thr Ser Arg Ile Ile Arg Ser Ser Glu Asp Pro Asn Glu
 15                  20                  25                  30

Asp Ile Val Glu Arg Asn Ile Arg Ile Ile Val Pro Leu Asn Asn Arg
                 35                  40                  45

Glu Asn Ile Ser Asp Pro Thr Ser Pro Leu Arg Thr Arg Phe Val Tyr
             50                  55                  60

His Leu Ser Asp Leu Cys Lys Lys Cys Asp Pro Thr Glu Val Glu Leu
 65                  70                  75
```

```
Asp Asn Gln Ile Val Thr Ala Thr Gln Ser Asn Ile Cys Asp Glu Asp
         80                  85                  90

Ser Ala Thr Glu Thr Cys Ser Thr Tyr Asp Arg Asn Lys Cys Tyr Thr
 95                 100                 105                 110

Ala Val Val Pro Leu Val Tyr Gly Gly Glu Thr Lys Met Val Glu Thr
                115                 120                 125

Ala Leu Thr Pro Asp Ala Cys Tyr Pro Asp
            130                 135
```

<210> SEQ ID NO 18
<211> LENGTH: 71
<212> TYPE: PRT
<213> ORGANISM: Homo sapiens

<400> SEQUENCE: 18

```
Asp Gln Lys Cys Lys Cys Ala Arg Ile Thr Ser Arg Ile Ile Arg Ser
 1               5                  10                  15

Ser Glu Asp Pro Asn Glu Asp Ile Val Glu Arg Asn Ile Arg Ile Ile
                20                  25                  30

Val Pro Leu Asn Asn Arg Glu Asn Ile Ser Asp Pro Thr Ser Pro Leu
            35                  40                  45

Arg Thr Arg Phe Val Tyr His Leu Ser Asp Leu Cys Lys Lys Asp Glu
     50                  55                  60

Asp Ser Ala Thr Glu Thr Cys
 65                  70
```

<210> SEQ ID NO 19
<211> LENGTH: 49
<212> TYPE: PRT
<213> ORGANISM: Homo sapiens

<400> SEQUENCE: 19

```
Ser Arg Ile Ile Arg Ser Ser Glu Asp Pro Asn Glu Asp Ile Val Glu
 1               5                  10                  15

Arg Asn Ile Arg Ile Ile Val Pro Leu Asn Asn Arg Glu Asn Ile Ser
                20                  25                  30

Asp Pro Thr Ser Pro Leu Arg Thr Arg Phe Val Tyr His Leu Ser Asp
            35                  40                  45

Leu
```

<210> SEQ ID NO 20
<211> LENGTH: 12
<212> TYPE: PRT
<213> ORGANISM: Homo sapiens

<400> SEQUENCE: 20

```
Asp Gln Lys Cys Lys Cys Ala Arg Ile Thr Ser Arg
 1               5                  10
```

<210> SEQ ID NO 21
<211> LENGTH: 14
<212> TYPE: PRT
<213> ORGANISM: Homo sapiens

<400> SEQUENCE: 21

```
Asp Leu Cys Lys Lys Asp Glu Asp Ser Ala Thr Glu Thr Cys
 1               5                  10
```

<210> SEQ ID NO 22

```
<211> LENGTH: 36
<212> TYPE: PRT
<213> ORGANISM: Homo sapiens

<400> SEQUENCE: 22

Ser Thr Tyr Asp Arg Asn Lys Cys Tyr Thr Ala Val Val Pro Leu Val
 1               5                  10                  15

Tyr Gly Gly Glu Thr Lys Met Val Glu Thr Ala Leu Thr Pro Asp Ala
            20                  25                  30

Cys Tyr Pro Asp
        35

<210> SEQ ID NO 23
<211> LENGTH: 93
<212> TYPE: PRT
<213> ORGANISM: Homo sapiens

<400> SEQUENCE: 23

Asp Gln Lys Cys Lys Cys Ala Arg Ile Thr Ser Arg Ile Ile Arg Ser
 1               5                  10                  15

Ser Glu Asp Pro Asn Glu Asp Ile Val Glu Arg Asn Ile Arg Ile Ile
            20                  25                  30

Val Pro Leu Asn Asn Arg Glu Asn Ile Ser Asp Pro Thr Ser Pro Leu
        35                  40                  45

Arg Thr Arg Phe Val Tyr His Leu Ser Asp Leu Cys Lys Lys Cys Asp
    50                  55                  60

Pro Thr Glu Val Glu Leu Asp Asn Gln Ile Val Thr Ala Thr Gln Ser
65                  70                  75                  80

Asn Ile Cys Asp Glu Asp Ser Ala Thr Glu Thr Cys Tyr
                85                  90

<210> SEQ ID NO 24
<211> LENGTH: 35
<212> TYPE: PRT
<213> ORGANISM: Homo sapiens

<400> SEQUENCE: 24

Asp Leu Cys Lys Lys Cys Asp Pro Thr Glu Val Glu Leu Asp Asn Gln
 1               5                  10                  15

Ile Val Thr Ala Thr Gln Ser Asn Ile Cys Asp Glu Asp Ser Ala Thr
            20                  25                  30

Glu Thr Cys
        35

<210> SEQ ID NO 25
<211> LENGTH: 22
<212> TYPE: PRT
<213> ORGANISM: Homo sapiens

<400> SEQUENCE: 25

Asp Gln Glu Asp Glu Arg Ile Val Leu Val Asp Asn Lys Cys Lys Cys
 1               5                  10                  15

Ala Arg Ile Thr Ser Arg
            20

<210> SEQ ID NO 26
<211> LENGTH: 66
<212> TYPE: PRT
<213> ORGANISM: Homo sapiens

<400> SEQUENCE: 26
```

```
Cys Ser Asp Asp Asp Lys Ala Gln Thr Glu Thr Cys Thr Val Ala
 1               5                  10                  15

Pro Arg Glu Arg Gln Asn Cys Gly Phe Pro Gly Val Thr Pro Ser Gln
            20                  25                  30

Cys Ala Asn Lys Gly Cys Cys Phe Asp Asp Thr Val Arg Gly Val Pro
                35              40                  45

Trp Cys Phe Tyr Pro Asn Thr Ile Asp Val Pro Pro Glu Glu Glu Cys
    50                  55                  60

Glu Phe
 65
```

<210> SEQ ID NO 27
<211> LENGTH: 421
<212> TYPE: DNA
<213> ORGANISM: Homo sapiens

<400> SEQUENCE: 27

| | | | | | | |
|---|---|---|---|---|---|---|
| gaattcagtc | cggatagcat | gcatcgggcg | taagggcagt | ttccaccatt | tttgtctctc | 60 |
| caccatacac | gagcggaacc | acggccgtgt | agcatttgtt | cctatcgtag | gtgctgcagg | 120 |
| tttctgtagc | gctgtcctca | tcgcaaatgt | tgctttgagt | cgcagtgact | atctgattgt | 180 |
| ccagctctac | ctctgttgga | tcacacttct | tacacagatc | tgacaggtgg | tatacgaagc | 240 |
| gtgtgcgcaa | cggacttgta | ggatctgaga | tattctcccg | ttattcagt | gggacgatga | 300 |
| tacgatgtt | acgttcgact | atatcttcat | ttgggtcctc | tgagctacgg | atgattctag | 360 |
| aagtaatacg | agcacacttg | cacttgttgt | caaccagaac | aatacgttca | tcttcctgat | 420 |
| c | | | | | | 421 |

<210> SEQ ID NO 28
<211> LENGTH: 219
<212> TYPE: DNA
<213> ORGANISM: Homo sapiens

<400> SEQUENCE: 28

| | | | | | | |
|---|---|---|---|---|---|---|
| aattcagcag | gtttctgtag | cgctgtcctc | atccttctta | cacagatctg | acaggtggta | 60 |
| tacgaagcgt | gtgcgcaacg | gacttgtagg | atctgagata | ttctcccggt | tattcagtgg | 120 |
| gacgatgata | cggatgttac | gttcgactat | atcttcattt | gggtcctctg | agctacggat | 180 |
| gattctagaa | gtaatacgag | cacacttgca | cttctgatc | | | 219 |

<210> SEQ ID NO 29
<211> LENGTH: 140
<212> TYPE: DNA
<213> ORGANISM: Homo sapiens

<400> SEQUENCE: 29

| | | | | | | |
|---|---|---|---|---|---|---|
| gatctgacag | gtggtatacg | aagcgtgtgc | gcaacggact | tgtaggatct | gagatattct | 60 |
| cccggttatt | cagtgggacg | atgatacgga | tgttacgttc | gactatatct | tcatttgggt | 120 |
| cctctgagct | acggatgatt | | | | | 140 |

<210> SEQ ID NO 30
<211> LENGTH: 31
<212> TYPE: DNA
<213> ORGANISM: Homo sapiens

<400> SEQUENCE: 30

| | | | |
|---|---|---|---|
| ctagaagtaa | tacgagcaca | cttgcacttc | t | 31 |

<210> SEQ ID NO 31
<211> LENGTH: 44
<212> TYPE: DNA
<213> ORGANISM: Homo sapiens

<400> SEQUENCE: 31
aattcagcag gtttctgtag cggactcttc atccttctta caca              44

<210> SEQ ID NO 32
<211> LENGTH: 117
<212> TYPE: DNA
<213> ORGANISM: Homo sapiens

<400> SEQUENCE: 32
aattcagtca gggtagcatg catcgggcgt aagggcagtt tccaccattt ttgtctctcc    60
accatacacg agcggaacca cggccgtgta gcatttgttc ctatcgtagg tgctgca      117

<210> SEQ ID NO 33
<211> LENGTH: 282
<212> TYPE: DNA
<213> ORGANISM: Homo sapiens

<400> SEQUENCE: 33
tcagtagcag gtttctgtag cgctgtcctc atcgcaaatg ttgctttgag tcgcagtgac    60
tatctgattg tccagctcta cctctgttgg atcacacttc ttacacagat ctgacaggtg   120
gtatacgaag cgtgtgcgca acggacttgt aggatctgag atattctccc ggttattcag   180
tgggacgatg atacggatgt tacgttcgac tatatcttca tttgggtcct ctgagctacg   240
gatgattcta gaagtaatac gagcacactt gcacttctga tc                     282

<210> SEQ ID NO 34
<211> LENGTH: 105
<212> TYPE: DNA
<213> ORGANISM: Homo sapiens

<400> SEQUENCE: 34
gcaggtttct gtagcgctgt cctcatcgca aatgttgctt tgagtcgcag tgactatctg    60
attgtccagc tctacctctg ttggatcaca cttcttacac agatc                  105

<210> SEQ ID NO 35
<211> LENGTH: 61
<212> TYPE: DNA
<213> ORGANISM: Homo sapiens

<400> SEQUENCE: 35
ctagaagtaa tacgagcaca cttgcacttg ttgtcaacca gaacaatacg ttcatcttcc    60
t                                                                   61

<210> SEQ ID NO 36
<211> LENGTH: 205
<212> TYPE: DNA
<213> ORGANISM: Homo sapiens

<400> SEQUENCE: 36
aattcttaaa actcgcactc ttcttcaggc ggaacgtcaa ttgtattggg gtagaagcac    60
cacggaagcc ccgtaccgtg tcatcaaaac agcagccttt attagcgcac tgagagggtg   120
ttactcccgg gaatccgcag ttttgccgtt cacgaggcgc aacagtacag gtctccgttt   180
gggccttatc gtcgtcatcg ctgca                                       205

<210> SEQ ID NO 37
<211> LENGTH: 13
<212> TYPE: PRT
<213> ORGANISM: Homo sapiens

<400> SEQUENCE: 37

Asp Gln Glu Asp Glu Arg Ile Val Leu Val Asp Asn Lys
 1               5                  10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 38

Glu Asn Leu Tyr Phe Gln Ser
 1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Linker
      peptide

<400> SEQUENCE: 39

Lys Ala His Lys Val Asp Met Val Gln Tyr Thr
 1               5                  10

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Linker
      peptide

<400> SEQUENCE: 40

Val Gln Tyr Thr
 1

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Linker
      peptide

<400> SEQUENCE: 41

Glu Lys Ala Val Ala Asp
 1               5

<210> SEQ ID NO 42
<211> LENGTH: 131
<212> TYPE: DNA
<213> ORGANISM: Homo sapiens
<220> FEATURE:
<221> NAME/KEY: CDS
<222> LOCATION: (1)..(78)

<400> SEQUENCE: 42

```
atg aaa ttc tta gtc aac gtt gcc ctt ttt atg gtc gta tac att tct       48
Met Lys Phe Leu Val Asn Val Ala Leu Phe Met Val Val Tyr Ile Ser
  1               5                  10                  15 tac atc tat gcg gat ccg agc tcg agt gct ctagatctgc agctggtacc          98
Tyr Ile Tyr Ala Asp Pro Ser Ser Ser Ala
                20                  25 atggaattcg aagcttggag tcgactctgc tga                                  131
```

<210> SEQ ID NO 43
<211> LENGTH: 26
<212> TYPE: PRT
<213> ORGANISM: Homo sapiens

<400> SEQUENCE: 43

```
Met Lys Phe Leu Val Asn Val Ala Leu Phe Met Val Val Tyr Ile Ser
  1               5                  10                  15

Tyr Ile Tyr Ala Asp Pro Ser Ser Ser Ala
                20                  25
```

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence:
      Intracellular targeting signal

<400> SEQUENCE: 44

```
Lys Asp Glu Leu
  1
```

<210> SEQ ID NO 45
<211> LENGTH: 16
<212> TYPE: PRT
<213> ORGANISM: Homo sapiens

<400> SEQUENCE: 45

```
Ala Ile Gln Asp Pro Arg Leu Phe Ala Glu Glu Lys Ala Val Ala Asp
  1               5                  10                  15
```

<210> SEQ ID NO 46
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
gatcaggaag atgaacgtat tgttctggtt gacaacaagt gcaagtgtgc tcgtattact      60
t                                                                     61
```

<210> SEQ ID NO 47
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
ctagaagtaa tacgagcaca cttgcacttg ttgtcaacca gaacaatacg ttcatcttcc      60
t                                                                     61
```

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gatcagaagt gcaagtgtgc tcgtattact t                                      31

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ctagaagtaa tacgagcaca cttgcacttc t                                      31

<210> SEQ ID NO 50
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gatcaggaag atgaacgtat tgttctggtt gacaacaagt gcaagtccgc tcgtattact       60
t                                                                       61

<210> SEQ ID NO 51
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ctagaagtaa tacgagcgga cttgcacttg ttgtcaacca gaacaatacg ttcatcttcc       60
t                                                                       61

<210> SEQ ID NO 52
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gatcaggaag atgaacgtat tgttctggtt gacaacaagt gcaaggttgc tcgtattact       60
t                                                                       61

<210> SEQ ID NO 53
<211> LENGTH: 61
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 53
ctagaagtaa tacgagcaac cttgcacttg ttgtcaacca gaacaatacg ttcatcttcc    60
t    61

<210> SEQ ID NO 54
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ctagaatcat ccgtagctca gaggacccaa atgaagatat agtcgaa    47

<210> SEQ ID NO 55
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gatacggatg ttacgttcga ctatatcttc atttgggtcc tctgagctac ggatgatt    58

<210> SEQ ID NO 56
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cgtaacatcc gtatcatcgt cccactgaat aaccgggaga atatctcag    49

<210> SEQ ID NO 57
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cgtaacatcc gtatcatcgt cccactgaat aaccgggagc acatctcag    49

<210> SEQ ID NO 58
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
acggacttgt aggatctgag atattctccc ggttattcag tgggacgat    49

<210> SEQ ID NO 59
<211> LENGTH: 49
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 59
acggacttgt aggatctgag atgtgctccc ggttattcag tgggacgat                    49

<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
atcctacaag tccgttgcgc acacgcttcg tataccacct gtca                        44

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gatctgacag gtggtatacg aagcgtgtgc gca                                    33

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gatctgtgta agaagtgtga tccaacagag gtagagctgg acaatcagat agtcactgca       60

<210> SEQ ID NO 63
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gatctgtgta agaaggatga ggacagcgct acagaaacct gctg                        44

<210> SEQ ID NO 64
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aattcagcag gtttctgtag cgctgtcctc atccttctta caca                        44

<210> SEQ ID NO 65
<211> LENGTH: 62
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 65
gatctgtgta agaaggatga ggacagcgct acagaaacct gctacgagaa ggatgagctg    60
tg                                                                  62

<210> SEQ ID NO 66
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
aattcacagc tcatccttcg cgtcgcaggt ttctgtagcg ctgtcctcat ccttcttaca    60
ca                                                                  62

<210> SEQ ID NO 67
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gatctgtgta agaagtctga tatcgatgaa gattccgcta cagaaacctg cagcacatg     59

<210> SEQ ID NO 68
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
aattcatgtg ctgcaggttt ctgtagcgga atcttcatcg atatcagact tcttacaca    59

<210> SEQ ID NO 69
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gatctgtcta agaagtctga tatcgatgaa gattacagat tcttcagact atagctactt    60
ctaa                                                                64

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aatcttcatc gatatcagac ttcttagaca                                    30

<210> SEQ ID NO 71

```
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gatctggtta agaagtctga tatcgatgaa gattaccaat tcttcagact atagctactt     60
ctaa                                                                  64

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aatcttcatc gatatcagac ttcttaacca                                      30

<210> SEQ ID NO 73
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
attgtccagc tctacctctg ttggatcaca cttcttacac a                         41

<210> SEQ ID NO 74
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
actcaaagca acatttgcga tgaggacagc gctacagaaa cctgca                    46

<210> SEQ ID NO 75
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggtttctgta gcgctctgct catcgcaaat gttgctttga gtcgcagtga ctatctg        57

<210> SEQ ID NO 76
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gcacctacga taggaacaaa tgctacacgg ccgtggttcc gctcgtgtat ggtggagag      59
```

<210> SEQ ID NO 77
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gagcggaacc acggccgtgt agcatttgtt cctatcgtag gtgctgca                   48

<210> SEQ ID NO 78
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
acaaaaatgg tggaaactgc ccttacgccc gatgcatgct atccggactg                 50

<210> SEQ ID NO 79
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aattcagtcc ggatagcatg catcgggcgt aagggcagtt tccaccattt ttgtctctcc      60
accatacac                                                              69

<210> SEQ ID NO 80
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
acaaaaatgg tggaaactgc ccttacgccc gatgcatgct atccggacaa ggatgaattg      60
tg                                                                     62

<210> SEQ ID NO 81
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
aattcacaat tcatccttgt ccggatagca tgcatcgggc gtaagggcag tttccaccat      60
ttttgtctct ccaccataca c                                                81

<210> SEQ ID NO 82
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gatcaggtcg ctgccatcca agacccgagg ctgttcgccg aagagaaggc cgtcgctgac    60
tccaagtgca agtgtgctcg tattactt                                      88

<210> SEQ ID NO 83
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ctagaagtaa tacgagcaca cttgcacttg gagtcagcga cggccttctc ttcggcgaac    60
agcctcgggt cttggatggc agcgacct                                      88

<210> SEQ ID NO 84
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 84
tggtacgaat tccaggtsma rctgcagsag tcrg                               34

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 85
acagatatcg ggatttctcg cagactc                                       27

<210> SEQ ID NO 86
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 86
acagaatatc gtcaacacct tcccaccc                                      28

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 87
acaaagcttt tatttacccg acagacggtc                                    30

<210> SEQ ID NO 88
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 88

```
gtcccccctc gagcgayaty swgmtsaccc artct                      35
```

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 89

```
acactgcagc agttggtgca gcatcagc                              28
```

<210> SEQ ID NO 90
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 90

```
ctgcaggaag cggaagcgga ggaagcggaa gcggaggaag cggaagcgaa ttc  53
```

<210> SEQ ID NO 91
<211> LENGTH: 47
<212> TYPE: DNA
<213> ORGANISM: Artificial Sequence
<220> FEATURE:
<223> OTHER INFORMATION: Description of Artificial Sequence: Linker
      complement

<400> SEQUENCE: 91

```
ccttcgcctt cgcctccttc gccttcgcct ccttcgcctt cgcttaa         47
```

<210> SEQ ID NO 92
<211> LENGTH: 76
<212> TYPE: DNA
<213> ORGANISM: Artificial Sequence
<220> FEATURE:
<223> OTHER INFORMATION: Description of Artificial Sequence: Signal
      peptide

<400> SEQUENCE: 92

```
acaggatcca tggaaacccc agcgcagctt ctcttcctcc tgctactctg gctcccaaga  60
taccaccgga cccggg                                                  76
```

<210> SEQ ID NO 93
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 93

```
tggtacagat ctaggtsmar ctgcagsagt crg                        33
```

<210> SEQ ID NO 94
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 94

```
acaggaattc aattttcttg tccacctt                              28
```

```
<210> SEQ ID NO 95
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 95
gttctagaga yatyswgmts acccartct                                    29

<210> SEQ ID NO 96
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 96
acaccgcggc agttggtgca gcatcagc                                     28

<210> SEQ ID NO 97
<211> LENGTH: 75
<212> TYPE: DNA
<213> ORGANISM: Homo sapiens

<400> SEQUENCE: 97
acaggatcca tggaaacccc agcgcagctt ctcttcctcc tgctactctg gctcccagat   60
accaccggaa gatct                                                   75

<210> SEQ ID NO 98
<211> LENGTH: 75
<212> TYPE: DNA
<213> ORGANISM: Homo sapiens

<400> SEQUENCE: 98
acaactagta tggaaacccc agcgcagctt ctcttcctcc tgctactctg gctcccagat   60
accaccggat ctaga                                                   75

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Linker
      peptide

<400> SEQUENCE: 99

Val Ala Val Gln Ser Ala Gly Thr Pro Ala Ser Gly Ser
 1               5                  10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Nuclear
      targeting sequence

<400> SEQUENCE: 100

Cys Ala Ala Pro Lys Lys Lys Arg Lys Val
 1               5                  10

<210> SEQ ID NO 101
<211> LENGTH: 22
<212> TYPE: PRT
```

```
<213> ORGANISM: Artificial Sequence
<220> FEATURE:
<223> OTHER INFORMATION: Description of Artificial Sequence: Nuclear
      targeting sequence

<400> SEQUENCE: 101

Cys Ala Ala Lys Arg Pro Pro Ala Ala Ile Lys Lys Ala Ala Ala Gly
  1               5                  10                  15

Gln Ala Lys Lys Lys Lys
             20

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence:
      Intracellular targeting signal

<400> SEQUENCE: 102

His Asp Glu Leu
  1

<210> SEQ ID NO 103
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gcgatgacga cgataaggcc caaacggaga cctgtactgt tgcgcctcgt gaacggcaaa      60
actgcggatt cccggga                                                    77

<210> SEQ ID NO 104
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gttttgccgt tcacgaggcg caacagtaca ggtctccgtt tgggccttat cgtcgtcatc      60
gctgca                                                                66

<210> SEQ ID NO 105
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gtaacaccct ctcagtgcgc taataaaggc tgctgttttg atgacacggt acggggcgtt      60
ccgtggtgct tc                                                         72

<210> SEQ ID NO 106
<211> LENGTH: 72
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 106
gccccgtacc gtgtcatcaa aacagcagcc tttattagcg cactgagagg gtgttactcc    60
cgggaatccg ca                                                        72

<210> SEQ ID NO 107
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
taccccaata caattgacgt tccgcctgaa gaagagtgcg agttttaag               49

<210> SEQ ID NO 108
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aattcttaaa actcgcactc ttcttcaggc ggcaagtcaa ttgtattggg gtagaagcac    60
cacggaac                                                             68

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Linker
      peptide

<400> SEQUENCE: 109

Pro Leu Gly Ile Ile Gly Gly
  1               5

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence: Linker
      peptide

<400> SEQUENCE: 110

Ile Ile Gly Gly
  1

<210> SEQ ID NO 111
<211> LENGTH: 30
<212> TYPE: PRT
<213> ORGANISM: Homo sapiens

<400> SEQUENCE: 111

Val Arg Asp Gln Ala Gln Glu Asn Arg Ala Ser Gly Asp Ala Gly Ser
  1               5                  10                  15

Ala Asp Gly Gln Ser Arg Ser Ser Ser Lys Val Leu Phe
             20                  25                  30

-continued

<210> SEQ ID NO 112
<211> LENGTH: 25
<212> TYPE: PRT
<213> ORGANISM: Homo sapiens

<400> SEQUENCE: 112

Val Pro Ser Thr Pro Pro Thr Pro Ser Pro Ser Thr Pro Pro Thr Pro
 1               5                  10                  15

Ser Pro Ser Cys Cys His Pro Arg Leu
            20                  25

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 113

Glu Gln Lys Leu Ile Ser Glu Asp Leu
 1               5

<210> SEQ ID NO 114
<211> LENGTH: 68
<212> TYPE: PRT
<213> ORGANISM: Homo sapiens

<400> SEQUENCE: 114

Cys Lys Cys Ala Arg Ile Thr Ser Arg Ile Ile Arg Ser Ser Glu Asp
 1               5                  10                  15

Pro Asn Glu Asp Ile Val Glu Arg Asn Ile Arg Ile Ile Val Pro Leu
            20                  25                  30

Asn Asn Arg Glu Asn Ile Ser Asp Pro Thr Ser Pro Leu Arg Thr Arg
        35                  40                  45

Pro Val Tyr His Leu Ser Asp Leu Cys Lys Lys Asp Glu Asp Ser Ala
    50                  55                  60

Thr Glu Thr Cys
65

<210> SEQ ID NO 115
<211> LENGTH: 12
<212> TYPE: PRT
<213> ORGANISM: Homo sapiens

<400> SEQUENCE: 115

Cys Lys Cys Ala Arg Asp Ser Asp Ala Glu Thr Cys
 1               5                  10

<210> SEQ ID NO 116
<211> LENGTH: 69
<212> TYPE: PRT
<213> ORGANISM: Homo sapiens

<400> SEQUENCE: 116

Cys Met Cys Thr Arg Val Thr Ser Arg Ile Ile Pro Ser Thr Glu Asp
 1               5                  10                  15

Pro Asn Glu Asp Ile Val Glu Arg Asn Ile Arg Ile Val Val Pro Leu
            20                  25                  30

Asn Asn Arg Glu Asn Ile Ser Asp Pro Thr Ser Pro Leu Arg Arg Asn
        35                  40                  45

Pro Val Tyr His Leu Ser Asp Val Cys Lys Lys Asn Glu Asp Asp Gly

```
                50                  55                  60
Val Pro Glu Thr Cys
 65

<210> SEQ ID NO 117
<211> LENGTH: 68
<212> TYPE: PRT
<213> ORGANISM: Homo sapiens

<400> SEQUENCE: 117

Cys Gln Cys Val Arg Ile Thr Ser Arg Ile Ile Arg Asp Pro Asp Asn
 1               5                  10                  15

Pro Ser Glu Asp Ile Val Glu Arg Asn Ile Arg Ile Val Pro Leu
            20                  25                  30

Asn Thr Arg Glu Asn Ile Ser Asp Pro Thr Ser Pro Leu Arg Thr Glu
        35                  40                  45

Pro Lys Tyr Asn Leu Ala Asn Leu Cys Lys Lys Pro Asp Asp Asp Tyr
    50                  55                  60

Ser Glu Thr Cys
 65

<210> SEQ ID NO 118
<211> LENGTH: 67
<212> TYPE: PRT
<213> ORGANISM: Homo sapiens
<220> FEATURE:
<221> NAME/KEY: VARIANT
<222> LOCATION: 37, 60, 62
<223> OTHER INFORMATION: Xaa = Any Amino Acid

<400> SEQUENCE: 118

Cys Lys Cys Val Lys Ile Ser Ser Arg Phe Val Pro Ser Thr Glu Arg
 1               5                  10                  15

Pro Gly Glu Glu Ile Leu Glu Arg Asn Ile Gln Ile Thr Ile Pro Thr
            20                  25                  30

Ser Ser Arg Met Xaa Ile Ser Asp Pro Tyr Ser Pro Leu Arg Thr Gln
        35                  40                  45

Pro Val Tyr Asn Leu Trp Asp Ile Cys Gln Lys Xaa Ser Xaa Pro Asp
    50                  55                  60

Asp Glu Cys
 65

<210> SEQ ID NO 119
<211> LENGTH: 69
<212> TYPE: PRT
<213> ORGANISM: Homo sapiens

<400> SEQUENCE: 119

Cys Met Cys Thr Arg Val Thr Ala Arg Ile Arg Gly Thr Arg Glu Asp
 1               5                  10                  15

Pro Asn Glu Asp Ile Val Glu Arg Tyr Ile Arg Ile Asn Val Pro Leu
            20                  25                  30

Lys Asn Arg Gly Asn Ile Ser Asp Pro Thr Ser Pro Leu Arg Asn Gln
        35                  40                  45

Pro Val Tyr His Leu Ser Pro Ser Cys Lys Lys Tyr Pro Asp Gln Gly
    50                  55                  60

Val Pro Gln Ser Cys
 65
```

```
<210> SEQ ID NO 120
<211> LENGTH: 87
<212> TYPE: PRT
<213> ORGANISM: Homo sapiens

<400> SEQUENCE: 120

Cys Lys Cys Ala Arg Ile Thr Ser Arg Ile Ile Pro Ser Ala Glu Asp
 1               5                  10                  15

Pro Ser Gln Asp Ile Val Glu Arg Asn Val Arg Ile Ile Val Pro Leu
                20                  25                  30

Asn Ser Arg Glu Asn Ile Ser Asp Pro Thr Ser Pro Met Arg Thr Lys
            35                  40                  45

Pro Val Tyr His Leu Ser Asp Leu Cys Lys Lys Cys Asp Thr Thr Glu
        50                  55                  60

Val Glu Leu Glu Asp Gln Val Thr Ala Ser Gln Ser Asn Ile Cys
 65                  70                  75                  80

Asp Ser Asp Ala Glu Thr Cys
                85

<210> SEQ ID NO 121
<211> LENGTH: 90
<212> TYPE: PRT
<213> ORGANISM: Homo sapiens

<400> SEQUENCE: 121

Cys Met Cys Thr Arg Val Thr Ser Arg Ile Ile Pro Ser Thr Glu Asp
 1               5                  10                  15

Pro Asn Glu Asp Ile Val Glu Arg Asn Ile Arg Ile Val Val Pro Leu
                20                  25                  30

Asn Asn Arg Glu Asn Ile Ser Asp Pro Thr Ser Pro Leu Arg Arg Asn
            35                  40                  45

Pro Val Tyr His Leu Ser Asp Val Cys Lys Lys Cys Asp Pro Val Glu
        50                  55                  60

Val Glu Leu Glu Asp Gln Val Val Thr Ala Thr Gln Ser Asn Ile Cys
 65                  70                  75                  80

Asn Glu Asp Asp Gly Val Pro Glu Thr Cys
                85                  90

<210> SEQ ID NO 122
<211> LENGTH: 89
<212> TYPE: PRT
<213> ORGANISM: Homo sapiens

<400> SEQUENCE: 122

Cys Gln Cys Val Arg Ile Thr Ser Arg Ile Ile Arg Asp Pro Asp Asn
 1               5                  10                  15

Pro Ser Glu Asp Ile Val Glu Arg Asn Ile Arg Ile Ile Val Pro Leu
                20                  25                  30

Asn Thr Arg Glu Asn Ile Ser Asp Pro Thr Ser Pro Leu Arg Thr Glu
            35                  40                  45

Pro Lys Tyr Asn Leu Ala Asn Leu Cys Lys Lys Cys Asp Pro Thr Glu
        50                  55                  60

Ile Glu Leu Asp Asn Gln Val Phe Thr Ala Ser Gln Ser Asn Ile Cys
 65                  70                  75                  80

Pro Asp Asp Asp Tyr Ser Glu Thr Cys
                85

<210> SEQ ID NO 123
```

```
<211> LENGTH: 85
<212> TYPE: PRT
<213> ORGANISM: Homo sapiens
<220> FEATURE:
<221> NAME/KEY: VARIANT
<222> LOCATION: 37, 82, 83, 85
<223> OTHER INFORMATION: Xaa = Any Amino Acid

<400> SEQUENCE: 123
```

Cys Lys Cys Val Lys Ile Ser Ser Arg Phe Val Pro Ser Thr Glu Arg
1               5                   10                  15

Pro Gly Glu Glu Ile Leu Glu Arg Asn Ile Gln Ile Thr Ile Pro Thr
            20                  25                  30

Ser Ser Arg Met Xaa Ile Ser Asp Pro Tyr Ser Pro Leu Arg Thr Gln
                35                  40                  45

Pro Val Tyr Asn Leu Trp Asp Ile Cys Gln Lys Cys Asp Pro Val Gln
        50                  55                  60

Leu Glu Ile Gly Gly Ile Pro Leu Leu Ala Ser Gln Pro Xaa Xaa Ser
65                  70                  75                  80

Xaa Pro Asp Asp Glu
                85

```
<210> SEQ ID NO 124
<211> LENGTH: 84
<212> TYPE: PRT
<213> ORGANISM: Homo sapiens

<400> SEQUENCE: 124
```

Cys Thr Arg Val Thr Ala Arg Ile Arg Gly Thr Arg Glu Asp Pro Asn
1               5                   10                  15

Glu Asp Ile Val Glu Arg Tyr Ile Arg Ile Asn Val Pro Leu Lys Asn
            20                  25                  30

Arg Gly Asn Ile Ser Asp Pro Thr Ser Pro Leu Arg Asn Gln Pro Val
                35                  40                  45

Tyr His Leu Ser Pro Ser Cys Lys Lys Cys Asp Pro Tyr Glu Asp Gly
        50                  55                  60

Val Val Thr Ala Thr Glu Thr Asn Ile Cys Tyr Pro Asp Gln Gly Val
65                  70                  75                  80

Pro Gln Ser Cys

```
<210> SEQ ID NO 125
<211> LENGTH: 12
<212> TYPE: PRT
<213> ORGANISM: Homo sapiens

<400> SEQUENCE: 125
```

Gln Glu Asp Glu Arg Ile Val Leu Val Asp Asn Lys
1               5                   10

```
<210> SEQ ID NO 126
<211> LENGTH: 12
<212> TYPE: PRT
<213> ORGANISM: Homo sapiens

<400> SEQUENCE: 126
```

Gln Asp Glu Asn Glu Arg Ile Val Val Asp Asn Lys
1               5                   10

```
<210> SEQ ID NO 127
<211> LENGTH: 11
<212> TYPE: PRT
```

```
<213> ORGANISM: Homo sapiens

<400> SEQUENCE: 127

Asp Asp Glu Ala Thr Ile Leu Ala Asp Asn Lys
 1               5                  10

<210> SEQ ID NO 128
<211> LENGTH: 11
<212> TYPE: PRT
<213> ORGANISM: Homo sapiens

<400> SEQUENCE: 128

Asp Asp Glu Ala Thr Ile Leu Ala Asp Asn Lys
 1               5                  10

<210> SEQ ID NO 129
<211> LENGTH: 10
<212> TYPE: PRT
<213> ORGANISM: Homo sapiens

<400> SEQUENCE: 129

Glu Gln Glu Tyr Ile Leu Ala Asn Asn Lys
 1               5                  10

<210> SEQ ID NO 130
<211> LENGTH: 7
<212> TYPE: PRT
<213> ORGANISM: Homo sapiens

<400> SEQUENCE: 130

Tyr Thr Tyr Asp Arg Asn Lys
 1               5

<210> SEQ ID NO 131
<211> LENGTH: 7
<212> TYPE: PRT
<213> ORGANISM: Homo sapiens

<400> SEQUENCE: 131

Tyr Thr Tyr Asp Arg Asn Lys
 1               5

<210> SEQ ID NO 132
<211> LENGTH: 7
<212> TYPE: PRT
<213> ORGANISM: Homo sapiens

<400> SEQUENCE: 132

Tyr Met Tyr Asp Arg Asn Lys
 1               5

<210> SEQ ID NO 133
<211> LENGTH: 7
<212> TYPE: PRT
<213> ORGANISM: Homo sapiens

<400> SEQUENCE: 133

Tyr Thr Tyr Asp Arg Asn Lys
 1               5

<210> SEQ ID NO 134
<211> LENGTH: 11
<212> TYPE: PRT
<213> ORGANISM: Homo sapiens
```

<400> SEQUENCE: 134

Arg Asp Tyr Cys Pro Glu Leu Asp Arg Asn Lys
1               5                   10

<210> SEQ ID NO 135
<211> LENGTH: 29
<212> TYPE: PRT
<213> ORGANISM: Homo sapiens

<400> SEQUENCE: 135

Cys Tyr Thr Ala Val Val Pro Leu Val Tyr Gly Gly Glu Thr Lys Met
1               5                   10                  15

Val Glu Thr Ala Leu Thr Pro Asp Ala Cys Tyr Pro Asp
            20                  25

<210> SEQ ID NO 136
<211> LENGTH: 29
<212> TYPE: PRT
<213> ORGANISM: Homo sapiens

<400> SEQUENCE: 136

Cys Tyr Thr Asn Arg Val Lys Leu Ser Tyr Arg Gly Gln Thr Lys Met
1               5                   10                  15

Val Glu Thr Ala Leu Thr Pro Asp Ser Cys Tyr Pro Asp
            20                  25

<210> SEQ ID NO 137
<211> LENGTH: 29
<212> TYPE: PRT
<213> ORGANISM: Homo sapiens

<400> SEQUENCE: 137

Cys Tyr Thr Thr Met Val Pro Leu Arg Tyr His Gly Glu Thr Lys Met
1               5                   10                  15

Val Gln Ala Ala Leu Thr Pro Asp Ser Cys Tyr Pro Asp
            20                  25

<210> SEQ ID NO 138
<211> LENGTH: 29
<212> TYPE: PRT
<213> ORGANISM: Homo sapiens

<400> SEQUENCE: 138

Cys Tyr Thr Thr Leu Val Pro Ile Thr His Arg Gly Val Thr Arg Met
1               5                   10                  15

Val Lys Ala Thr Leu Thr Pro Asp Ser Cys Tyr Pro Asp
            20                  25

<210> SEQ ID NO 139
<211> LENGTH: 24
<212> TYPE: PRT
<213> ORGANISM: Homo sapiens

<400> SEQUENCE: 139

Cys Tyr Thr Thr Glu Val Asn Phe Lys Lys Val Pro Leu Thr Pro
1               5                   10                  15

Asp Ser Cys Tyr Glu Tyr Ser Glu
            20

<210> SEQ ID NO 140
<211> LENGTH: 29
<212> TYPE: PRT

```
<213> ORGANISM: Homo sapiens

<400> SEQUENCE: 140

Cys Tyr Thr Val Leu Val Pro Pro Gly Tyr Thr Gly Glu Thr Lys Met
1               5                   10                  15

Val Gln Asn Ala Leu Thr Pro Asp Ala Cys Tyr Pro Asp
            20                  25
```

EPITHELIAL TISSUE TARGETING AGENT

CROSS-REFERENCE TO RELATED APPLICATION

This application is a continuation-in-part of U.S. patent application Ser. No. 08/782,481, filed Jan. 10, 1997.

TECHNICAL FIELD

The present invention relates generally to the targeting of therapeutic compounds to specific cells and tissues. The invention is more particularly related to targeting molecules for use in delivering compounds to epithelial tissue. Such targeting molecules may be used in a variety of therapeutic procedures.

BACKGROUND OF THE INVENTION

Improving the delivery of drugs and other agents to target tissues has been the focus of considerable research for many years. Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., cytotoxic agents and other anti-cancer or anti-viral drugs) that can be administered. By comparison, although oral administration of drugs is generally recognized as a convenient and economical method of administration, oral administration can result in either (a) uptake of the drug through the epithelial barrier, resulting in undesirable systemic distribution, or (b) temporary residence of the drug within the gastrointestinal tract. Accordingly, a major goal has been to develop methods for specifically targeting agents to cells and tissues that may benefit from the treatment, and to avoid the general physiological effects of inappropriate delivery of such agents to other cells and tissues.

In addressing this issue, some investigators have attempted to use chimeric molecules that bind to growth factor receptors on gastrointestinal epithelial cells to facilitate transepithelial transport of therapeutic agents (see WO 93/20834). However, these methods have several disadvantages. For example, such chimeric molecules are transcytosed through the epithelium from the gut lumen and absorbed into the blood stream, resulting in systemic distribution and removal from the epithelium proper. Since the therapeutic agents are targeted specifically away from the epithelium for systemic distribution, these chimeric molecules are generally not useful for treatment of epithelium associated conditions. In addition, TGF-α or other molecules binding to EGF receptors exhibit many or all of the apparent biological activities of EGF, such as stimulation of enterocyte mitogenesis or suppression of gastric secretion. Such effects collateral to the transcytotic uptake of therapeutic agents may not be desirable or may be contraindicated for intervention of epithelium associated conditions or diseases. Furthermore, EGF receptors are not unique to epithelial cells of the gastrointestinal tract, and can be found on numerous other cells including kidney cells and hepatocytes. Thus, molecules which have affinity for the EGF receptor and are distributed systemically in the blood can be rapidly removed from circulation, accumulated in specific organs and potentially degraded or secreted.

Within an alternative approach, other investigators have employed Fab fragments of an anti-polymeric immunoglobulin receptor IgG to target DNA to epithelial cells in vitro that contain such a receptor (see Ferkol et al., *J. Clin. Invest.* 92:2394-2400, 1993). Still other researchers have described the translocation of a chimeric IgA construct across a monolayer of epithelial cells in vitro (see Terskikh et al., *Mol. Immunol.* 31:1313-1319, 1994). Others have used ascites tumor implants in vivo in mice and observed an IgA dimeric antibody produced by subcutaneous tumor cells to accumulate in feces, suggesting that IgA is transported across an epithelial barrier of the gastrointestinal tract (see Greenberg et al., *Science* 272:104-107, 1996).

Notwithstanding the above-noted developments, there remains a need in the art for systems for delivering agents to target cells, particularly epithelial cells and cells or tissues bounded by epithelial cells. The present invention fulfills these needs and further provides other related advantages.

SUMMARY OF THE INVENTION

Briefly stated, the present invention provides targeting molecules for the specific delivery of biological agents to epithelial cells and tissues. In several aspects, the present invention provides a targeting molecule linked to at least one biological agent. In one such aspect, the targeting molecule comprises a polypeptide that (a) forms a closed covalent loop; and (b) contains at least three peptide domains having β-sheet character, each of the domains being separated by domains lacking β-sheet character; wherein the polypeptide is not a full length dimeric IgA. In specific embodiments, the polypeptide further contains one or more of the following additional domains: a fourth peptide domain having β-sheet character, separated from other domains having β-sheet character by a domain lacking β-sheet character; a linear N-terminal domain; and a C-terminal domain, which may comprise a linear peptide having β-sheet character and/or a covalently closed loop.

Within other such aspects, the targeting molecule comprises a sequence recited in any one of SEQ ID NO:1-SEQ ID NO:8 and SEQ ID NO:13.

In a further related aspect, the present invention provides a targeting molecule capable of specifically binding to a basolateral factor associated with an epithelial surface and causing the internalization of a biological agent linked thereto, wherein the targeting molecule is not full length dimeric IgA.

Within related aspects, the targeting molecule comprises a polypeptide that: (a) forms a closed covalent loop; and (b) contains at least three peptide domains having β-sheet character, each of the domains being separated by domains lacking β-sheet character; wherein the targeting molecule is linked to at least one biological agent by a substrate for an intracellular or extracellular enzyme associated with or secreted from an epithelial barrier, or by a side chain of an amino acid in an antibody combining site.

Within further related aspects, the targeting molecule is linked to at least one biological agent, wherein the targeting molecule comprises a polypeptide that: (a) forms a closed covalent loop; and (b) contains at least three peptide domains having β-sheet character, each of the domains being separated by domains lacking β-sheet character; wherein the biological agent is not naturally associated with the targeting molecule, and wherein the biological agent is not iodine.

Within another aspect, the present invention provides a pharmaceutical composition comprising a targeting molecule linked to at least one biological agent, as described above, in combination with a pharmaceutically acceptable carrier.

In further aspects, methods are provided for treating a patient afflicted with a disease associated with an epithelial surface, comprising administering to a patient a pharmaceutical composition as described above. Such diseases include cancer, viral infection, inflammatory disorders, autoimmune disorders, asthma, celiac disease, colitis, pneumonia, cystic fibrosis, bacterial infection, mycobacterial infection and fungal infection.

Within related aspects, the present invention provides methods for inhibiting the development in a patient of a disease associated with an epithelial surface, comprising administering to a patient a pharmaceutical composition as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 is a comparison of native J chain sequences reported for human (top line) (SEQ ID NO:1), mouse (second line) (SEQ ID NO:2), rabbit (third line) (SEQ ID NO:3), cow (fourth line) (SEQ ID NO:4), bull frog (fifth line) (SEQ ID NO:5) and earth worm (sixth line) (SEQ ID NO:6). For each non-human sequence, amino acid residues that are identical to those in the human sequence are indicated by a dash. Residues that differ from the human sequence are indicated using standard one letter abbreviations.

DETAILED DESCRIPTION OF THE INVENTION

As noted above, the present invention is generally directed to targeting molecules (TMs) for use in the delivery of drugs and other biological agents to epithelial cells. Upon delivery to an epithelial cell, the agent may remain within the cell or may undergo transepithelial transport via transcytosis. For example, the agent and TM may be transported across the basolateral surface and remain within the epithelial cell, or the agent may remain within the cell while the TM undergoes transepithelial transport. Agents that remain within the epithelial cell may modify an activity or function of a cellular component or a foreign component, such as a virus. Alternatively, both the agent and TM may undergo transcytosis. For example, an agent linked to a TM may pass through an epithelial cell surface to access an adjacent cell, tissue or compartment (e.g., lumen of the small intestine, bronchial airway, vaginal cavity), and/or may bind a substance within an epithelial cell and then remove the substance from the cell. Further, an agent may (but need not) be designed to be inactive when entering the epithelial cell, and be activated following transcytosis or upon a specific event (e.g., viral infection).

Prior to setting forth the present invention in detail, definitions of certain terms used herein are provided.

Epithelial surface (or epithelial barrier): A surface lining the exterior of the body, an internal closed cavity of the body or body tubes that communicate with the exterior environment. Epithelial surfaces include the genitourinary, respiratory, alimentary, ocular conjunctiva, nasal, oral and pharyngeal cavities, as well as the ducts and secretory portions of glands and receptors of sensory organs. The term "epithelial surface" as used herein is synonymous with "epithelial barrier." One side of an epithelial surface is free of adherence to cellular and extracellular components, other than coating substances and secretions. The other side of the surface is normally adjacent to the basement membrane and is exposed to interstitial fluids and components of the underlying tissues. Epithelial surfaces are typically formed from cells in close apposition to one another, the contact between plasma membranes of adjacent cells characterized by a tight junction (zonula occludens) which delimits the outside and inside domains of an epithelial surface. An experimental epithelial-like surface can be generated in vitro with autonomously replicating cell lines (e.g., MDCK, ATCC No. CCL34; HEC-1A, ATCC No. HTB 112), which form epithelial-like surfaces in culture, have tight junctions and articulate one free (apical) and one adherent (basolateral) domain.

Apical domain: The outside of an epithelial surface which is adjacent to the environment external to the body or to the volume of a body cavity or body tube. The outside of the cells, as delimited by the zonula occludens, is composed of the coating substances, secretions and cell membranes facing the outside of the epithelial surface.

Luminal compartment: The inner space of a body tube, cavity or duct lined by an epithelial surface and adjacent to the apical domain.

Basolateral domain: The inside of the epithelial surface which is delimited from the apical domain by the zonula occludens. The basolateral domain is adjacent to the basement membrane and is exposed to interstitial fluids and components of the tissues underlying epithelial surfaces. The basolateral domain is the inner side of cells of an epidermal surface.

Basolateral membrane: The portion of the plasma membrane of a cell of an epithelial surface which is within the basolateral domain.

Basolateral factor: A component of the basolateral domain which is a naturally occurring element of a basolateral membrane in vivo. A "basolateral factor associated with an epithelial surface" refers to a basolateral factor attached by covalent or noncovalent bonds to a basolateral domain, or a component of the membrane proper in a basolateral domain.

Internalization: The process of uptake into a cell compartment that is bounded by a plasma membrane.

Specific binding: A TM specifically binds to a basolateral domain if it specifically interacts at the basolateral domain of an epithelial surface. Both quantitative and qualitative assays may be used to distinguish specific binding from binding which is not specific within the context of the subject invention. A quantitative measurement of binding affinity ($k_{aff}$) may be used to identify components that bind specifically. In general, a $k_{aff}$ of $10^4$ $M^{-1}$ or higher constitutes specific binding between two binding components. The binding affinity for the cognate components of a binding interaction can be estimated experimentally by a variety of methods that are well known in the art, including equilibrium dialysis assays, precipitation radioimmunoassays, assays with immobilized ligands, assays with isolated cells or membranes, ELISAs, or by other direct or indirect measurements or binding (e.g., plasmon resonance).

Qualitative specificity of binding is demonstrated by differential, or asymmetric distribution of binding of a factor among two or more chemical, spatial or temporal domains. This differential distribution can be observed visually, or by chemical or physical means, and generally reflects approximately at least a 3 to 1 differential in signal intensity between basolateral and non-basolateral domains. Such qualitative specificity may result from substantial differences in the affinity of binding of an agent to one of several domains, or to the number or availability of cognate binding sites on a domain. The qualitative specificity of binding of an agent among several domains can be observed in a competition experiment. In such an experiment a TM is allowed to distribute among domains, and at equilibrium is observed to preferentially bind to one domain over another.

Targeting Molecule (TM): A molecule capable of specifically binding to a cognate factor on epithelial surfaces, which is not uniformly distributed.

Biological agent: Any molecule, group of molecules, virus, component of a virus, cell or cell component that is synthesized by a cell or ex vivo, can be derived from a cell and/or can be demonstrated to modify the properties of a cell. Biological agents include therapeutic agents (i.e., drugs and other medicinal compounds useful for treating or preventing a disorder or regulating the physiology of a patient).

Linked: A biological agent is linked to a TM if it is attached covalently, by ionic interaction and/or by hydrophobic interactions, or by other means such that under physiological conditions of pH, ionic strength and osmotic potential the linked entities are associated with each other at equilibrium.

TMs as described herein are generally capable of specifically binding to a factor preferentially distributed on an epithelial surface, such as a basolateral factor. Through binding to such a factor, TMs are capable of causing the internalization of a biological agent linked to the TM. TMs as described herein have a distinct three-dimensional structure. In general, TMs comprise a polypeptide that forms a closed covalent loop which is referred to herein as the "core." All subunits of the polypeptide may, but need not, be connected by identical chemical bonds. In a preferred embodiment, the polypeptide comprises amino and/or imino acids covalently joined by peptide bonds and one or more cystine disulfide bridges.

The core of a TM typically contains at least three peptide domains having β-sheet character, interspersed among regions lacking β-sheet character. In this regard, a "peptide domain" is a portion of a polypeptide comprising at least three amino acid residues. A peptide domain is said to have β-sheet character if the peptide backbone has an extended conformation with side-chain groups in a near planar and alternating arrangement such that hydrogen bonding can occur between carbonyl and NH groups of the backbone of adjacent β-strands. Furthermore, TMs generally contain at least one cysteine residue not present within an intramolecular cystine. Such cysteine(s) may be used for linking one or more biological agents to the TM, although other means of linking biological agents are also contemplated.

One or more of a variety of other structures may, but need not, be additionally present within a TM. For example, a second peptide loop may be present within the core sequence. Additional N-terminal and/or C-terminal sequences may be present. If present, N-terminal sequences are usually linear. A preferred N-terminal sequence is a short (about 1-20 amino acid residues) peptide domain. C terminal sequences may be linear and/or may form one or more loops. Such sequences may, but need not, possess domains having β-sheet character. These and/or other protein domains may be added to the core by genetic means or chemically, using covalent bonds or noncovalent interactions.

In a preferred embodiment, a TM comprises all or a portion of a native J chain sequence, or a variant thereof. J chain is a 15 kD protein that, in vivo, links IgM or IgA monomers to form pentameric IgM or dimeric IgA (see Max and Korsmeyer, *J. Exp. Med* 161:832-849, 1985). To date, sequences of J chains from six organisms have been deduced (see FIG. 1 and SEQ ID NO:1-SEQ ID NO:6; Kulseth and Rogne, *DNA and Cell Biol.* 13:37-42, 1994; Matsuuchi et al., *Proc. Natl. Acad. Sci. USA* 83:456-460, 1986; Max and Korsmeyer, *J. Exp. Med.* 161:832-849, 1985; Hughes et al., *Biochem J.* 271:641-647, 1990; Mikoryak et al., *J. Immunol.* 140:4279-4285, 1988; Takahashi et al., *Proc. Natl. Acad. Sci. USA* 93:1886-1891, 1996). A TM may comprise a native J chain from one of these organisms, or from any other organism.

Alternatively, a TM may comprise a portion or variant of native J chain sequence. A variant is a polypeptide that differs from a native a sequence only in one or more substitutions and/or modifications. Portions and variants of the native J chain sequence contemplated by the present invention are those that substantially retain the ability of the native J chain to specifically bind to a basolateral factor associated with an epithelial surface, and cause the internalization of a linked biological agent. Such portions and variants may be identified using, for example, the representative assays described herein.

Within the context of the TM compositions provided herein, the TM is not full length dimeric IgA. More specifically, the TM does not contain all of the components present within a naturally-occurring IgA (i.e., a heavy chain containing contiguous variable, $C_H1\alpha$, $C_H2\alpha$ and $C_H3\alpha$ domains and a light chain containing contiguous variable and $C_L$ domains). Such a TM may, of course, contain one or more portions of an IgA molecule, including an IgM.

As noted above, specific binding may be evaluated using quantitative and/or qualitative methods. In one representative quantitative assay, secretory component (SC) isolated from human milk by standard immunoaffinity chromatography methods (Underdown et al., *Immunochemistry* 14:111-120, 1977) is immobilized on a CM5 sensor chip with a BIACORE apparatus (Pharmacia, Piscataway, N.J.) by primary amine coupling. The sensor chip is activated by injection of 30 μL of 0.05M N-hydroxysuccinimide and N-ethyl-N-(3-diethylaminopropyl)carbodiimide, followed by injection of 25 μL of human SC (15 μg/mL) in 10 mM sodium acetate, pH 5.0. Unreacted carbodiimide is then quenched with 30 μL ethanolamine. All reagents are delivered at a flow rate of 5 μL per minute. To evaluate the kinetics of binding and desorption, serial two fold dilutions of TMs at concentrations between 100 μM and 100 nM are injected in binding buffer: 25 mM Tris, pH 7.2, 100 mM NaCl, 10 mM $MgCl_2$ at a flow rate of 20 μL per minute. Between dilutions, the surface is regenerated by injecting 50 μL of 25 mM Tris, pH 7.2, 200 mM NaCl, 2M urea, followed by injecting 50 μL of binding buffer. Association and dissociation constants are derived from sensograms using BIAevaluation 2.1 software to derive simple association ($k_a$) and dissociation constants ($k_d$). The $K_{aff}$ is estimated as $k_a/k_d$.

In one representative qualitative assay, monolayers of HEC-1 A cells can be used to measure qualitative binding of TMs. The procedure is based on previously published protocols (see Ball et al., *In Vitro Cell Biol.* 31:96, 1995). HEC-1A cells are cultured on 24 mm filter transwells (Costar, #3412, 0.4 μm) for one week until cells are confluent. Monolayer-covered filter transwells are washed twice on both surfaces with cold PBS (4° C.). One ml of cold MEM-BSA containing 1.0 μg of biotinylated ligand is added to the apical chamber and 1.5 ml cold MEM-BSA buffer (MEM-BSA (4° C.): minimum essential medium with hank's salts, and 25 mM HEPES buffer without L-glutamine (Life Technologies, Gaithersburg, Md.; Cat. No. 12370) containing 0.5% BSA, which is treated at 56° C. for 30 min to inactivate endogenous protease and filter sterilized) containing 1.5 μg of biotinylated ligand is added to the basolateral chamber. The cultures are kept at 4° C. for 2 hours to achieve maximum binding in the absence of internalization. The medium is removed from both chambers, and the filters are washed twice with cold PBS. Filters are then remove from the transwell supports with a scalpel and incubated with a streptavidin-fluorescein conjugate (#21223, Pierce Chemical Company, Rockford, Ill.), 0.1 μg/mL in cold PBS, then washed 3 times with cold PBS. 1 cm square pieces of filter are then cut from the 24 mm filter and mounted on microscope slides and observed microscopically under epifluorescence illumination (excitation 490 nm, emission 520 nm). Under these conditions the apical membranes show little or no fluorescence, while basolateral membranes demonstrate bright fluorescence (i.e., greater than a 3 to 1 differential in signal intensity) indicating specific binding to the basolateral domain. Similar assays can be employed with isolated epithelial tissues from gastrointestinal, oral or bronchial epithelial tissue layers.

Once bound to the basolateral domain of an epithelial cell, a TM may be internalized within a cell of an epithelium-like monolayer. Suitable cells for evaluating internalization include MDCK cells expressing the human polyimmunoglobulin receptor (pIgR) (see Tamer et al., *J. Immunol* 155:707-714, 1995) and HEC1-A cells. One assay in which internalization can be observed employs a HEC1-A cell line grown to confluent monolayers on permeable membrane supports (such as Costar, Cambridge, Mass., #3412). Briefly, 100 μg to 10 μg of a TM (e.g., fluorescein labeled) may be added to 1.5 mL of assay buffer in the basolateral compartment of cell monolayers and incubated at a temperature that allows binding and internalization of TMs, but that inhibits transcytosis (e.g., 90 minutes at 16° C.). The medium from both compartments is then removed and the filter membranes washed (e.g., twice at 4° C. with PBS). The membrane is immersed in a fixation solution of, for example, 3% (w/v) paraformaldehyde, 1% (w/v) glutaraldehyde, 5% (w/v) sucrose, 100 mM Na phosphate pH 7.4 on ice for 30 minutes. The membranes may be removed from the plastic insert by cutting around the periphery with a scalpel and cut into 5 mm square sections. These wholemount sections may be placed on microscope slides and observed microscopically under epifluorescence illumination (excitation 490 nm, emission 520 nm) or by fluorescence confocal microscopy. Internalized TM is indicated by the presence of bright green-yellow fluorescence in intracellular vesicles.

Substitutions and modifications that result in a variant that retains the qualitative binding specificity for a basolateral factor (i.e., a 3 to 1 or greater differential in signal intensity between basolateral and non-basolateral domains) are considered to be conservative. Preferred conservative substitutions and modifications include alterations in a sequence that render it, at least in part, consistent with the J chains of one or more other species. A TM may also, or alternatively, contain other sequences that confer properties not present in a native J chain. Other preferred modifications include the addition of one or more protein domains at the N- and/or C-terminus and/or altering the order of domains present within a native J chain sequence. A variant may contain any combination of such substitution(s) and/or modification(s), provided that the ability of the variant to specifically bind to an epithelial basolateral factor and cause internalization of the linked biological agent is not substantially reduced.

A native J chain typically has 6 domains. The first (N-terminal) domain is a short linear (i.e., as contrasted to a loop) peptide that serves (in vivo) as the junction between the signal peptide and the core TM molecule. Domain 1 typically contains 1-20 amino acid residues, and the first amino acid is generally D, E or Q. In FIG. 1, Domain 1 contains the amino acids up to and including residue number 11. Domain 1 is not essential for TM function, and variants that do not contain this domain are within the scope of the present invention.

Domain 2 typically contains 90 amino acids, and possesses substantial β-sheet character. This β-sheet region contains peptides of varying length lacking β-strand character (e.g., residues 26-31, 49-53), the peptides usually containing polar and/or charged amino acids. In a TM, Domain 2 is a covalently closed peptide loop, called the core, which is typically formed by an intramolecular cystine composed of the initial and ultimate residues of Domain 2 (residues 12 and 101 of FIG. 1). Within Domain 2, there may be another cystine bond that defines Domain 3, a peptide loop that is nested within the core. It has been found, within the context of the present invention, that the core (with or without Domain 3) is sufficient to provide TM function. Accordingly, a preferred TM contains Domain 2 (i.e., residues 12-70 and 92-101 of FIG. 1), or a portion or variant thereof that substantially retains TM function.

Within Domain 2, the second cysteine is generally separated from the initial cysteine of Domain 2 by a single amino acid residue (see, for instance, FIG. 1). Between the second and third cysteines of Domain 2 is a region of primarily β-sheet character. These two cysteines (2 and 3) when present, typically do not form cystines within the core. The fourth cysteine is typically separated from the third cysteine by two basic amino acid residues and initiates Domain 3. Domain 3 ends with the fifth cysteine which is oxidized by the fourth cysteine. The resulting cystine forms a covalent peptide loop defining Domain 3 contained completely within Domain 2. Cysteine 6 is the ultimate residue of Domain 2, and is oxidized to cystine by the initial residue of Domain 2.

Within the core is a canonical peptide sequence for N-linked glycosylation (e.g., NIS). When produced by eukaryotic cells, carbohydrate moieties can be covalently attached to an N residue of a TM at this site.

When present, Domain 3 is typically a peptide 21 amino acids in length. This domain is delimited by amino and carboxy terminal cysteine residues which form an intramolecular cystine bond that is contained completely within the core.

Domains 4-6 are carboxy terminal domains in native J chains which may, but need not, be present within a TM. Domain 4 is typically a peptide of seven amino acids. In native J chains, this peptide contains no cysteine residues and connects the core to Domain 5. Domain 5 is, when present, typically a peptide of 26 amino acids delimited by amino and carboxy terminal cysteine residues which form an intramolecular cystine bond resulting in a covalently closed loop. In native J chains, the amino and carboxy terminal portions of Domain 5 have substantial β-sheet character and are separated by a short 3-6 residue peptide with low β-sheet propensity. Domain 6 is typically a short peptide of five amino acids or less which serves as the carboxy terminus of a TM. Domains 4-6 are not essential for TM function.

As noted above, numerous variants of native J chain sequences may be employed within TMs as described herein. For example, a TM core, as described above, can serve as a molecular scaffolding for the attachment and/or substitution of Domains and/or additional molecular components. Possible variants include:

TMs in which Domain 1 comprises a peptide of about 13 amino acids, the middle third of which has substantial β-sheet character (e.g., DQEDERIVLVDNK; SEQ ID NO:37);

TMs in which the asparagine residue at position 48 is changed to histidine (e.g., AAT to CAC);

TMs in which Domain 1 comprises a three amino acid peptide DNK;

TMs in which Domain 1 contains a peptide with a sequence specific for recognition and cleavage by a protease which can be used to release distal portion of the TM from a proximal colinear peptide or protein (e.g., a peptide recognized by the tobacco etch virus protease Nia: ENLYFQS; SEQ ID NO:38);

TMs in which Domain 1 contains a peptide sequence which specifies the intracellular targeting of the contiguous peptide (e.g., a nuclear targeting peptide);

TMs in which one or both of the native cysteine residues 2 or 3 within Domain 2 are removed or replaced to eliminate the possibility of intermolecular crosslinking (e.g., substitutions of S, T, A, V or M residues for the native C);

TMs in which a portion of Domain 3 is deleted, such that there is a peptide bond between the amino acid distal to the end of the third β-sheet of Domain 3 and the initial residue of the ultimate peptide of Domain 3;
- TMs in which other peptides that form loop structures or other antiparallel peptide domains are included in place of Domain 3, or between its defining cysteines, to provide functionalities or recognition domains to the TM (e.g., viral capsid protein loops);
- TMs in which Domain 4 is truncated to form a TM without Domains 5 and 6;
- TMs in which Domain 4 is replaced as described above for Domain 3 to introduce a new functionality, specificity and/or structure to the TM;
- TMs in which Domain 4 contains a proteolytic site specific for a cellular compartment which would result in cleavage of the TM into two molecules in a cellular compartment;
- TMs in which the loop structure of Domain 5 is replaced with a peptide sequence to provide functionalities or recognition domains to the TM (e.g., single chain antibody variable region or viral capsid protein loop);
- TMs in which Domain 6 is terminated in a peptide sequence or is replaced with a peptide sequence that would target the contiguous TM protein to an intracellular target (e.g., KDEL, SEQ ID NO:44, or HDEL, SEQ ID NO:102, for retention in the endomembrane system);
- TMs that additionally comprise one or more immunoglobulin-derived sequences (e.g., domains of the Ig heavy chain classes: alpha3, alpha2, alpha1, mu4, mu3, mu2, mu1) linked via one or more disulfide and/or peptide bonds. Such sequences may serve as attachment sites for one or more biological agents.

The above list of representative variants is provided solely for illustrative purposes. Those of ordinary skill in the art will recognize that the modifications recited above may be combined within a single TM and that many other variants may be employed in the context of the present invention.

TMs may generally be prepared using any of a variety of well known purification, chemical and/or recombinant methods. Naturally-occurring TMs (e.g., human J chain) may be purified from suitable biological materials, as described herein. All or part of a TM can be synthesized in living cells, with the sequence and content defined by the universal genetic code, a subset of the genetic code or a modified genetic code specific for the living cells. Any of a variety of expression vectors known to those of ordinary skill in the art may be employed to achieve expression in any appropriate host cell. Suitable host cells include insect cells, yeast cells, mammalian cells, plant cells, algae, bacteria and other animal cells (e.g., hybridoma, CHO, myeloma).

An example of a synthetic gene encoding a targeting molecule is provided in SEQ ID NO:7. Such synthetic genes may be ligated into, for example, a polyhedrin-based baculovirus transfer vector such as pMelBac A, pMelBac B or pMelBac C (Invitrogen, San Diego, Calif.) between suitable restriction sites (e.g., the BamHI and SalI sites) and introduced into insect cells such as High Five, Sf9 or Sf21 in a cotransfection event using Bac-N-Blu AcMNPV DNA (Invitrogen, San Diego, Calif.) according to standard methods. Other suitable vectors and host cells will be readily apparent to those of ordinary skill in the art.

Synthetic polypeptide TMs or portions thereof having fewer than about 100 amino acids, and generally fewer than about 50 amino acids, may be generated using synthetic techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is readily available from suppliers such as Applied BioSystems, Inc., Foster City, Calif., and may be operated according to the manufacturer's instructions.

In addition to the TMs described above, there are other molecules which may bind specifically to a basolateral factor associated with an epithelial cell and subsequently result in internalization into epithelial cells followed by transcytosis through the epithelial barrier. Such molecules include peptides or proteins containing antibody domains which bind to the polyimmunoglobulin receptor. This type of molecule may be identified in screening assays employing epithelium-like surfaces in culture.

Within one suitable screening assay, a combinatorial library of peptides is employed, each peptide of which contains an easily identifiable biochemical or chemical marker such as a biotinyl-lysine residue, or a tyrosine residue modified by covalent linkage to radiolabeled iodine. In such an assay, individual peptides or families of peptides with 8 to 15 amino acid residues are incubated in solutions exposed to the basolateral surface of an epithelium-like monolayer cell culture. After incubation of the peptide solution, the solution on the apical surface of the cell culture is assayed for the presence of transported peptides by analysis for the biochemical or chemical marker included during synthesis. Subsequent analysis of the peptide sequence of the transported peptide, for instance by mass spectrometry, is used to reveal the identity of a peptide which can be transported across an epithelium-like surfaces in culture. Any peptide identified in this manner is then synthesized by chemical means to contain a fluorescent marker. The peptide containing a fluorescent marker is then incubated in solutions exposed to the basolateral surface of an epithelium-like monolayer cell culture under conditions which allow binding, but not internalization (e.g., 4° C.) or under conditions which allow uptake but not transcytosis (e.g., 16° C.) and the cells observed microscopically to determine the ability the peptides to bind or to be internalized by the cells of an epithelium-like layer.

A similar assay can be used to screen populations of monoclonal antibodies, single chain antibodies, antibody combining regions, or Fab fragments for the ability to bind to, be internalized and transcytosed by epithelial cells containing the polyimmunoglobulin receptor. Antibodies raised in animals immunized with secretory component, with the polyimmunoglobulin receptor, or animals naïve to such immunization are incubated in solutions exposed to the basolateral surface of an epithelium-like monolayer cell culture. After incubation of antibodies, the solution on the apical surface of the cell culture is assayed for the presence of transported antibodies by analysis for the presence of antibody or antibody fragment. This evaluation can be performed using commercially available antibodies for enzyme linked immunosorbent assays, or by immunoblotting techniques. Either of these assays can be performed easily by one skilled in the art of characterizing antibodies.

Any antibody or antibody fragment identified in this manner may then be isolated and conjugated to a fluorescent marker. The immunoglobulin thus attached to a fluorescent marker is then incubated in solutions exposed to the basolateral surface of an epithelium-like monolayer cell culture under conditions which allow binding, but not internalization (e.g., 4° C.) or under conditions which allow uptake but not transcytosis (e.g., 16° C.) and the cells observed microscopically to determine the ability the antibodies to bind or to be internalized by the cells of an epithelium-like layer. Ferkol et al., *J. Clin. Invest.* 92:2394-2400 have identified an antibody binding domain by similar methods.

Linkage of a TM to one or more biological agents may be achieved by any means known to those in the art, such as genetic fusion, covalent chemical attachment, noncovalent attachment (e.g., adsorption) or a combination of such means. Selection of a method for linking a TM to a biological agent will vary depending, in part, on the chemical nature of the agent and depending on whether the agent is to function at the basolateral surface, within the epithelial cell, or undergo transcytosis. Linkage by genetic fusion may be performed using standard recombinant DNA techniques to generate a nucleic acid molecule that encodes a single fusion peptide containing both the biological agent(s) and the TM. Optionally, the fusion peptide may contain one or more linker sequences and/or sequences for intracellular targeting (e.g., KDEL (SEQ ID NO:44), protease cleavage sites, nuclear targeting sequences, etc.). The recombinant nucleic acid molecule is then introduced into an appropriate vector and expressed in suitable host cells. Techniques for generating such a recombinant molecule and expressing a fusion peptide are well known to those of ordinary skill in the art (see, e.g., Sambrook et al., *Molecular Cloning: A Laboratory Manual,* 2d ed., Cold Spring Harbor Laboratory, Cold Spring Harbor, N.Y., 1989). Any biological agent having a known polypeptide sequence may be linked to a TM by genetic fusion. For example, using recombinant techniques, one or more immunoglobulin-derived sequences (e.g., single chain antigen binding proteins, hinge, Fv gamma or Fv kappa) may be linked to a TM at the N- and/or C-terminus.

Linkage may also be achieved by covalent attachment, using any of a variety of appropriate methods. For example, the TM and biological agent(s) may be linked using bifunctional reagents (linkers) that are capable of reacting with both the TM and the biological agent(s) and forming a bridge between the two. Commonly available bifunctional cross-linkers are capable of joining carbohydrates, amines, sulfhydryls and carboxyl functional groups, or may employ photoreactive groups to enable covalent linkage. These reagents are particularly useful for the attachment of, for example, additional peptide linkers that are in turn attached to biological agents. Covalent attachment of linkers may be accomplished through bonding to amino acid side chains present in the antigen combining site of an antibody linked to a TM. Briefly, attachment of linkers to such residues can occur as a result of the antibody recognition process itself when the linker is recognized as antigen and compatible reactive residues are present on the linker and in the binding domain of the antibody. Such reactive antibodies typically have antigen combining sites containing amino acid residues with side chains which can act as nucleophiles (e.g., aspartate, glutamate, glutamine, lysine and/or asparagine). For delivery of agents that will remain within the epithelial cell, linkers that are cleaved within the target cell may be particularly useful. Release of the biological agent within the cell may introduce or augment a genetic capability of the cell (e.g., increasing the P53 protein level in carcinoma cells) or may inhibit an existing cellular activity (e.g., antisense oligonucleotides may bind functional intracellular transcripts that are essential for tumorigenesis, tumor maintenance and/or metastases, such as transcripts that generate high levels of glycolytic enzymes).

Any of a variety of molecules may serve as linkers within the present invention. Polynucleotide and/or peptide linkers may be used. Such molecules may then be digested by, for example, intestinal nucleases and proteases (e.g., enterokinase, trypsin) respectively to release the biological agent. Preferred linkers include substrates for proteases associated with an epithelial barrier (i.e., proteases resident in, on or adjacent to epithelial cells or surfaces).

Numerous proteases are present in or associated with epithelial cells and/or epithelial surfaces. Processing of secreted proteins, for example, requires proteolytic scission of a portion of the newly synthesized protein (referred to as the pre-protein) prior to secretion from the cellular endomembrane system. Further processing, which may be required to liberate an active enzyme from the cell, for example, can result from additional proteolysis wherein the substrate may be referred to as the pro-protein or pro-enzyme. The specific proteolytic cleavage sites of these pro-proteins can be identified by comparison of the amino acid sequence of the final secreted protein with the sequence of the newly synthesized protein. These cleavage sites identify the substrate recognition sequences of particular intracellular proteases. One such protease recognition site, specific to epithelial cells, may reside within the amino acid sequence from residues 585-600 of the human polyimmunoglobulin receptor (pIgR, SEQ ID NO:45; numbering according to Piskurich et al., *J. Immunol.* 154:1735-1747, 1995). Alternatively, the intracellular scission of pIgR may be contained within residues 601-630 (VRDQAQENRASGDAGSADGQSRSSSSKVLF, SEQ ID NO:111). Subsequent shortening of SC from the carboxy terminus to yield mature SC may occur due to a carboxypeptidase in the mucosal environment. Peptides comprising all or part of the sequence from residue 601 to 630 may be useful for endosomal release of transcytosing TM-drug conjugates. Another such protease recognition site, which identifies a peptide substrate for many matrix metalloproteinases (MMPs) comprises the amino acid sequence PLGIIGG (SEQ ID NO:109). Since cancer cells often contain and secrete abundant quantities of MMPs this sequence may be efficiently cleaved specifically in and around cancer cells. Since cancer cells secrete abundant quantities of proteases, the intracellular proteases which are responsible for their processing are also in abundance. One such protease recognition site, which identifies a protease which also may be abundant in cancer cells, comprises residues 30-40 of procathepsin E (SEQ ID NO:39). Another type of protease recognition sequence comprises residues in the CH2 region of human IgA1 (VPSTPPTPSPSTPPTPSPSCCHPRL, SEQ ID NO:112) and is cleavable by IgA specific proteases secreted by microorganisms.

These protease recognition sites are extremely useful in the design of scissile linkers enabling the delivery of drugs, imaging compounds, or other biological agents to the intracellular environment of epithelial cells or to the epithelial barrier in general. Delivery of such compounds to epithelial cells can be accomplished by using residues 585-600 of human pIgR (SEQ ID NO:45) or residues 601-630 (SEQ ID NO:111) as part of the scissile linker joining the biological compound to TM. Delivery of anti-cancer drugs to tumors of epithelial origin can be accomplished using a substrate recognition sequence of MMPs (SEQ ID NO:109) or residues 30-40 of procathepsin E (SEQ ID NO:39) as part of the scissile linker to TM. Alternatively, scissile linkers may be designed from other cancer cell specific or epithelial barrier specific processing proteases which may be identified by the comparison of newly synthesized and secreted proteins or similar techniques. Other types of proteases that can be used to cleave scissile bonds can be found in the mammalian duodenum, for example. The enterokinase recognition sequence, $(Asp)_4$-lys (residues 3-7 of SEQ ID NO:26), can be used as a scissile linker for delivery of biological compounds to the duodenum by TM mediated transcytosis across the duodenum epithelial barrier. Proteolytic cleavage releases the biological agent with a small fragment of linker (e.g., VQYT, SEQ ID NO:40, from procathepsin; EKVAD, SEQ ID NO:41, from pIgR; or IIGG, SEQ ID NO:110 from the general MMP substrate sequence). Such residual linker segments may in turn be further digested by proteolytic enzymes (e.g., carboxypeptidase II or aminopeptidase 1) to yield an unmodified biological agent.

Scissile peptide linkers are generally from about 5 to about 50 amino acid residues in length. They can be covalently linked to TM or to adducts attached to TM by genetic fusion techniques (i.e., in frame with the 5' or 3' sequence of TM codons or adduct codons) or by any of a variety of chemical procedures enabling the joining of various functional groups (e.g., $NH_2$, COOH, SH). Alternatively the scissile peptide can itself comprise an antigen which may then be bound to TMs containing a cognate antigen binding capability. For example a scissile peptide comprising the sequence -Glu-Gln-Lys-Leu-Ile-Ser-Glu-Asp-Leu- (SEQ ID NO: 113) will be recognized and bound by an anti-myc antibody (e.g., Cat. No. R950-25, Invitrogen, Carlsbad, Calif.). Similarly, a scissile peptide containing an oligohistidine at its carboxy terminus will be recognized and bound by an anti-His (C-term) antibody (e.g., Cat. No. R930-25, Invitrogen, Carlsbad, Calif.).

Other substrates for intracellular proteases associated with an epithelial barrier include, but are not limited to, substrates for a phospholipase or glycosidase. Alternatively, a linker may comprise repeating positively charged lysine residues that will bind negatively charged nucleic acid molecules for release in the cell. Peptide linkers may be particularly useful for peptide biological agents, such as the antibiotic cecropins, magainins and mastoparins.

Carbohydrates may be covalently attached to native carbohydrate or to the polypeptide backbone of a TM, and employed as linkers. Suitable carbohydrates include, but are not limited to, lactose (which may be degraded by a lactase residing in, for example, the small intestine), sucrose (digested by a sucrase) and α-limit dextrin (digested by a dextrinase). Enzymes responsible for cleaving carbohydrate linkers can be found attached to the brush border membranes of the luminal surface of the epithelial barrier. Sucrase-isomaltase, for example, will cleave 1,4-α bonds of maltose, maltotriose and maltopentose. An intestinal brush border specific linker would therefore be comprised of any polymer of maltose linked by 1,4-α bonds. When attached to TM, the linker would pass through the epithelial barrier by transcytosis and would only be cleaved by sucrase-isomaltase resident on the apical surface of the epithelial barrier.

Lipids may also, or alternatively, be covalently attached to the polypeptide backbone for use as linkers. A monoglyceride employed in this manner may then be digested by intestinal lipase to release a biological agent linked to glycerol or a fatty acid. Phospholipids may be attached to a TM via a peptide linkage to the phosphatidylserine polar head group or by an ether or ester linkage to one of the hydroxyl groups of the head group of phosphatidyl inositol. The non-polar head group (diacylglycerol) may be substituted entirely by the biological agent in active or inactive form. For example, a penicillin linked via its R group to the phosphate of 1-phospho-myo-inositol-TM will be inactive until released by a phospholipase C derived from a bacterial infection. Other suitable linker moieties will be apparent to those of ordinary skill in the art.

Linkage may also be performed by forming a covalent bond directly between a TM and a biological agent. Regardless of whether a linker is employed, any of a variety of standard methods may be used to form a covalent linkage. For peptide biological agents and linkers, such a covalent bond may be a disulfide bond between cysteine residues of the TM and biological agent. Briefly, such bonds may be formed during the process of secretion from the endomembrane system of higher organisms. In such cases, the peptide biological agent(s) and TM must contain appropriate signals specifying synthesis on endomembranes. Such signals are well known to those of ordinary skill in the art. Reactive antibodies may covalently attach directly to a biological agent or a linker. Antibodies raised against antigens containing reactive groups or transition state analogs for specific reactions may contain residues in the combining site capable of forming covalent interactions with the antigen or with similar molecules. An example of such a reaction occurs between a lysine residue in the combining site of the monoclonal antibody 38C2 which reacts to form a vinylogous amide linkage with diketone and other closely related molecules (Wagner et al., *Science* 270:1797-1800, 1995). A TM containing a reactive antibody or the combining site of a reactive antibody can be used to form covalent bonds with linkers of lipid, peptide, carbohydrate, nucleic acid or other compositions. TMs containing biological agents attached to TM via covalent bonds in the combining site can be expected to have normal conformations and functions in the antibody domain. The absence of modifications to antibody structure outside the antigen combining site minimize the potential for altering the recognition of such molecules as foreign when introduced into the body. Further, the molecules tethered through combining sites of antibodies of human origin are expected to have half-lives in serum and other body compartments similar to those of native antibodies and have a low propensity to stimulate antibody responses against the TM.

As noted above, any therapeutic biological agent may be linked to a TM. Biological agents include, but are not limited to, proteins, peptides and amino acids; nucleic acids and polynucleotides; steroids; vitamins; polysaccharides; minerals; fats; inorganic compounds and cells or cell components.

A biological agent may also be a prodrug that generates an agent having a biological activity in vivo. In general, biological agents may be attached using a variety of techniques as described above, and may be present in any orientation.

The category of peptide biological agents includes a variety of binding agents. As used herein, a "binding agent" is any compound that binds to a molecule within the cell and inactivates and/or facilitates removal of the molecule. Binding agents include single chain antigen binding proteins, which may be used, for example, to inhibit viral pathogen assembly by binding essential components inside the cell and subsequently transcytosing components across the apical boundary; to bind and remove bacterial toxins by transcytosis; to bind and remove serum or cellular toxins or metabolites; or to bind and remove environmental toxins.

A binding agent may also be an antigen combining site such as, but not limited to, a reactive antigen combining site. For example, an antigen combining site may bind to an enzyme (e.g., an active site), and inhibit an activity of the enzyme. An antigen combining site may also bind to other molecules and inhibit other cellular functions such as, for example, a ribosome or transporter.

Enzymes may also be employed, including kinases, transferases, hydrolases, isomerases, proteases, ligases and oxidoreductases such as esterases, phosphatases, glycosidases and peptidases. For example, an enzyme linked to a TM could result in specific proteolytic cleavage of bacterial toxins, attachment proteins or essential cell surface functions (viral or bacterial), proteolytic cleavage of secreted cancer cell specific proteins (such as proteases) that are essential for tumor maintenance or metastases, degradation of cell surface carbohydrates essential to pathogenicity of viruses or bacteria or specific transfer of biochemical functions (such as phosphorylation) to inhibit extracellular cancer cell specific or pathogen specific functions.

Peptide biological agents may also be enzyme inhibitors (e.g., leupeptin, chymostatin or pepstatin); hormones (e.g., insulin, proinsulin, glucagon, parathyroid hormone, colony stimulating factor, growth hormone, thyroid hormone, erythropoetin, follicle stimulating hormone, luteinizing hormone, tumor necrosis factors); hormone releasing hormones (e.g., growth hormone releasing hormone, corticotropin releasing factor, luteinizing hormone releasing hormone, growth hormone release inhibiting hormone (somatostatin), chorionic gonadotropin releasing factor and thyroid releasing hormone); cell receptors (e.g., hormone receptors such as estrogen receptor) and cell receptor subunits; growth factors (e.g., tumor angiogenesis factor, epidermal growth factor, nerve growth factor, insulin-like growth factor); cytokines (e.g., interferons and interleukins); histocompatibility antigens; cell adhesion molecules; neuropeptides; neurotransmitters such as acetylcholine; lipoproteins such as alpha-lipoprotein; proteoglycans such as hyaluronic acid; glycoproteins such as gonadotropin hormone; antibodies (polyclonal, monoclonal or fragment); as well as analogs and chemically modified derivatives of any of the above.

Polynucleotide biological agents include antisense oligonucleotides (DNA or RNA) such as HIV, EBV EBNa-1 or reverse transcriptase antisense nucleotides; polynucleotides directed against active oncogenes or viral-specific gene products and polynucleotides complementary to unique sequences in the autoimmune B-cell immunoglobulin genes or T-cell receptor genes, or to mutant protein alleles (e.g., the mutant β-amyloid protein); and polynucleotides encoding proteins (e.g., DNA within expression vectors or RNA) including drug resistance genes. Also included are polynucleotide agents with catalytic activities (e.g., ribozymes) or with the ability to covalently bind to cellular or viral DNA, RNA or proteins. Nucleotides (e.g., thymine) and radionuclides (e.g., iodine, bromine, lead, palladium, copper) may also be employed.

A wide variety of steroid biological agents may be employed, including progesterone, androgens and estrogens (including contraceptives such as ethinyl estradiol). Similarly, agents such as vitamins (including fat soluble vitamins such as vitamins A, D, E and K and analogs thereof) may be linked to a TM. Inorganic biological agents include oxides, such as iron oxide. Polysaccharide biological agents include any of a variety of carbohydrates, as well as lipopolysaccharides and compounds such as heparin.

Biological agents linked to TMs may have any of a wide variety of activities in vivo. For example, a biological agent may be an antiviral agent (e.g., a nucleotide or nucleoside analog, such as Ara-AMP, DDA or AZT, an antiviral antibody or other agent such as rifampicin and acylovir), an antibacterial agent (e.g., penicillin, sulfanilamides, cecropins, magainins, mastoparans, actinomycin, gramicidin, aminoglycosides such as gentamycin, streptomycin and kanamycin; bleomycins such as bleomycin $A_2$, doxorubicin, daunomycin and antisense nucleotides complementary to the 3' terminus of prokaryotic 16S rRNA), an antifungal agent (e.g., azoles such as fluconazole, polyene macrolides such as aminoptericin B and candicidin), an antiparasitic agent (e.g., antimonials or antisense nucleotides complementary to a conserved sequence of the haem polymerase gene of *Plasmodium falciparum* or to a nucleotide leader sequence common to parasites such as trypanosomes) or an antitumor agent (e.g., 5-fluorouracil, methotrexate and intercalating agents such as cis-diaminodichloroplatimun).

A biological agent may also be a chemoprotective agent (e.g., N-acetyl-L-cysteine, folinic acid); a radioprotective agent (e.g., WR 2721, selenium, melanins, cysteamine derivatives, phenolic functional groups such as 6-hydroxychroman-2 carboxylic acids (e.g., Trolox) and tocopherols) or a cytotoxic agent (e.g., nitrogen mustard agents such as L-phenylalanine nitrogen mustard or cyclophosphamide, antifolates, vinca alkaloids, anthracyclines, mitomycins, cytotoxic nucleosides, the pterine family of drugs, podophyophyllotoxins, sulfonureas, trichothecenes and colchicines; specific cytotoxic agents include aminopterin, taxol, doxorubicin, fostreicin, camptothecin methopterin, dichloromethotrexate, mitomycin C, porfiromycin, 6-mercaptopurine, cytosine arabinoside, podophyllotoxin, etoposide, melphalan, vinblastine, vincristine, desacetylvinblastine hydrazide, leurosidine, vindesine, leurosine, trichothecene, desacetylcolchicine, paclitaxel, caminomycin, 4'-epiadriamycin, 4-demethoxy-daunomycin, 11-deoxydaunorubicin, 13-deoxydaunorubicin, adriamycin-14-benzoate, adriamycin-14-octanoate, adriamycin-14-naphthaleneacetate, N-methyl mitomycin C, dideazatetrahydrofolic acid, cholchicine and cisplatin).

In other embodiments, a biological agent may be an immunomodulating agent or vaccine; an antihistamine (e.g., diphenylhydramine, chlorpheniramine); a drug that affects the cardiovascular, renal or hepatic system; a sympathomimetic drug such as catecholamines (e.g., epinephrine) and non-catecholamines (e.g., phenylephrine and pseudoephedrine); a hormone antagonist; a toxin such as diphtheria toxin, ricin, abrin, pseudomonal aeruginosa endotoxin A, ribosomal inactivating proteins, mycotoxins such as trichothecenes and gelonin; a vasoactive agent; an anticoagulant; an anesthetic or sedative (e.g., dibucane); a decongestant; or a pain reliever (e.g., narcotic).

A biological agent may also be a neuroactive agent, including neuroleptics such as phenothiazines (e.g., compazine, thorazine, promazine, chlorpromazine, acepromazine, aminopromazine, perazine, prochlorperazine, trifluoperazine and thioproperazine); rauwolfia alkaloids (e.g., reserpine and deserpine); thioxanthenes (e.g., chlorprothixene); butyrophenones (e.g., haloperidol, moperone, trifluoperidol, timiperone and droperidol); diphenylbutylpiperidines (e.g., pimozide); benzamides (e.g., sulpride and tiapride); tranquilizers such as glycerol derivatives (e.g., mephenesin and methocarbamol), propanediols (e.g., meprobamate), diphenylmethane derivatives (e.g., orphenadrine, benzotrapine and hydroxyzine) and benzodiazepines (e.g., chlordiazepoxide and diazepam); hypnotics (e.g., zolpdem and butoctamide); betablockers (e.g., propranolol, acebutonol, metoprolol and pindolol); antidepressants such as dibenzazepines (e.g., imipramine), dibenzocycloheptenes (e.g., amitriptyline) and tetracyclics (e.g., mianserine); MAO inhibitors (e.g., phenelzinem iproniazid and selegeline); psychostimulants such as phenylethylamine derivatives (e.g., amphetamines, dexamphetamines, fenproporex, phentermine, amfepramone and pemoline) and dimethylaminoethanlos (e.g., clofenciclan, cyprodenate, a minorex and mazindol); GABA-mimetics (e.g., progabide); alkaloids (e.g., codergocrine, dihydroergocristine and vincamine); cholinergics (e.g., citicoline and physostigmine); vasodilators (e.g., pentoxifyline); or cerebroactive agents (e.g., pyritinol and meclofenoxate).

Table 1 below provides some examples of representative combinations of TM (with or without immunoglobulin-derived sequence(s)) and biological agent(s). In some cases, linkers are also indicated. For such combinations, intracellular delivery may be achieved using appropriate scissile linkers. Alternatively, other intracellular targeting sequences (e.g., KDEL (SEQ ID NO:44)) may be incorporated. In the absence of sequences that direct the TM intracellularly, the TMs provided in Table 1 deliver the biological agent(s) via transcytosis. Multiple orientations for all TM attachments are possible.

TABLE I

Representative Targeting Molecule/Biological Agent Combinations

| Combination | Variations/Comments |
|---|---|
| GENETIC FUSIONS | |
| TM-scabp | |
| scabp-TM | |
| scabp-TM-scabp | |
| TM/alpha3-scabp(s) | Either or both ligands N or C |
| TM/alpha3,2-scabp(s) | " |
| TM/alpha3,2,1-scabp(s) | " |
| TM/mu4-scabp(s) | " |
| TM/mu4,3-scabp(s) | " |
| TM/mu4,3,2-scabp(s) | " |
| TM/mu4,3,2,1-scabp(s) | " |
| TM-Fv | gamma or kappa Fv; associated with complementary Fv to form antigen binding site, Fab |
| Fv-TM | |
| Fv-TM-Fv | |
| TM/alpha3-Fv(s) | Either or both ligands N or C |
| TM/alpha3,2-Fv(s) | " |
| TM/alpha3,2,1-Fv(s) | " |
| TM/mu4-Fv(s) | " |
| TM/mu4,3-Fv(s) | " |
| TM/mu4,3,2-Fv(s) | " |
| TM/mu4,3,2,1-Fv(s) | " |

TABLE I-continued

Representative Targeting Molecule/Biological Agent Combinations

| Combination | Variations/Comments |
|---|---|
| TM-hinge-Fv | gamma or kappa hinge-Fv; associated with complementary Fv-hinge to form antigen binding site, Fab |
| Fv-hinge-TM-hinge-Fv | |
| TM/alpha3,2-hinge-Fv(s) | Either or both ligands N or C |
| TM/alpha3,2,1-hinge-Fv(s) | " |
| TM/mu4-hinge-Fv(s) | " |
| TM/mu4,3-hinge-Fv(s) | " |
| TM/mu4,3,2-hinge-Fv(s) | " |
| TM/mu4,3,2,1-hinge-Fv(s) | " |
| TM-Enz | |
| Enz-TM | |
| Enz-TM-Enz | |
| TM/alpha3-Enz(s) | Either or both ligands N or C |
| TM/alpha3,2-Enz(s) | " |
| TM/alpha3,2,1-Enz(s) | " |
| TM/mu4-Enz(s) | " |
| TM/mu4,3-Enz(s) | " |
| TM/mu4,3,2-Enz(s) | " |
| TM/mu4,3,2,1-Enz(s) | " |
| CHEMICAL MODIFICATIONS | |
| TM-carbo | |
| carbo-TM | |
| carbo-TM-carbo | |
| TM/ligand-carbo(s) | |
| TM-lipid | |
| lipid-TM | |
| lipid-TM-lipid | |
| TM/ligand-lipid(s) | |
| TM-nucleic acid | |
| nucleic acid-TM | |
| nucleic acid-TM-nucleic acid | |
| TM/ligand-nucleic acid(s) | |
| TM-peptide | |
| peptide-TM | |
| peptide-TM-peptide | |
| TM/ligand-peptide(s) | |
| TM-nucleic acid/antiviral | |
| antiviral/nucleic acid-TM | |
| antiviral/nucleic acid-TM-nucleic acid/antiviral | |
| TM/ligand-nucleic acid/antiviral(s) | |
| TM-lipid-antibiotic | |
| antibiotic-lipid-TM | |
| antibiotic-lipid-TM-lipid-antibiotic | |
| TM/ligand-lipid-antibiotic(s) | |
| TM-peptide-antibiotic | |
| antibiotic-peptide-TM | |
| antibiotic-peptide-TM-peptide antibiotic | |
| TM/ligand-peptide-antibiotic(s) | |

TM = targeting molecule;
scabp = single chain antigen binding protein;
enz = enzyme;
carbo = carbohydrate;
ligand = immunoglobulin-derived sequence (alpha3, alpha2 and/or alpha1; mu4, mu3, mu2 and/or mu1);
N = NH$_2$ terminal;
C = COOH terminal Of course, the above examples of biological agents are provided solely for illustrative purposes and are not intended to limit the scope of the invention. Other agents that may be employed within the context of the present invention will be apparent to those having ordinary skill in the art.

In one embodiment, a targeting molecule as described above is linked to a biological agent that is not naturally associated with the targeting molecule. Within the context of this embodiment, the biological agent is not iodine. The biological agent may, for example, be an enzyme, binding agent, inhibitor, nucleic acid, carbohydrate or lipid. In one preferred embodiment the biological agent comprises an antigen combining site.

TMs linked to one or more biological agents may be used for a variety of therapeutic purposes. In general, such TMs may be employed whenever it is advantageous to deliver a biological agent to epithelial tissue (for internalization and/or transcytosis). For example, a variety of conditions associated with an epithelial surface (i.e., conditions where an infectious agent gains access to the body through an epithelial surface; where an infection agent is resident in or on epithelial cells or surfaces; where epithelial barriers are compromised due to a disease condition or where epithelial tissue or cells are dysfunctional, transformed or the focus of an inflammatory response) may be treated and/or prevented using biological agents linked to TMs. Such conditions include, but are not limited to, cancer, viral infection, inflammatory disorders, autoimmune disorders, asthma, celiac disease, colitis, pneumonia, cystic fibrosis, bacterial infection, mycobacterial infection and fungal infection (such as yeast infection). Appropriate biological agents will vary depending on the nature of the condition to be treated and/or prevented and include those provided above, as well as others known to those of ordinary skill in the art.

As used herein, "treatment" refers to a lessening of symptoms or a delay in, or cessation of, the progression of the condition. A biological agent linked to a TM is generally administered to a patient afflicted with the condition in the form of a pharmaceutical composition, at a therapeutically effective dosage. To prepare a pharmaceutical composition, an effective concentration of one or more TM-biological agent complexes is mixed with a suitable pharmaceutical carrier or vehicle. Alternatively, a pharmaceutical composition may contain cells from the host or from another organism (e.g., a myeloma cell, stem cell, dendritic cell, hepatocyte or basal cell) which, when introduced into the body of the host, produce a TM. An amount of a TM (or cells that produce a TM in vivo) that, upon administration, ameliorates the symptoms or treats the disease is considered effective. Therapeutically effective concentrations and amounts may be determined empirically by testing the TMs in known in vitro and in vivo systems; dosages for humans or other animals may then be extrapolated therefrom. Pharmaceutical carriers or vehicles include any such carriers known to those skilled in the art to be suitable for the particular mode of administration.

The compositions of the present invention may be prepared for administration by a variety of different routes, including orally, parenterally, intravenously, intradermally, subcutaneously or topically, in liquid, semi-liquid or solid form and are formulated in a manner suitable for each route of administration. Preferred modes of administration depend upon the indication treated.

Solutions or suspensions used for oral, parenteral, intradermal, subcutaneous or topical application can include one or more of the following components: a sterile diluent, saline solution (e.g., phosphate buffered saline), fixed oil, polyethylene glycol, glycerin, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. In addition, other pharmaceutically active ingredients and/or suitable excipients such as salts, buffers, stabilizers and the like may, but need not, be present within the composition. Liposomal suspensions may also be suitable as pharmaceutically acceptable carriers. These may be prepared according to methods known to those skilled in the art.

A TM may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others.

A pharmaceutical composition is generally formulated and administered to exert a therapeutically useful effect while minimizing undesirable side effects. The number and degree of acceptable side effects depends upon the condition for which the composition is administered. For example, certain toxic and undesirable side effects are tolerated when treating life-threatening illnesses, such as tumors, that would not be tolerated when treating disorders of lesser consequence. The concentration of biological agent in the composition will depend on absorption, inactivation and excretion rates thereof, the dosage schedule and the amount administered, as well as other factors known to those of skill in the art.

The composition may be administered one time, or may be divided into a number of smaller doses to be administered at intervals of time. The precise dosage and duration of treatment is a function of the disease being treated and may be determined empirically using known testing protocols or by extrapolation from in vivo or in vitro test data. Dosages may also vary with the severity of the condition to be alleviated. For any particular subject, specific dosage regimens may be adjusted over time according to the individual need of the patient.

The following examples are offered by way of illustration and not by way of limitation.

EXAMPLES

Example 1

Preparation of Targeting Molecules

This example illustrates the preparation of representative targeting molecules.

A. Purification of Representative TMs from Biological Sources

Preparation of dimeric IgA (dIgA). Ten ml of human IgA myeloma plasma (International Enzymes, Inc., Fallbrook, Calif.) is mixed with an equal volume of PBS, and 20 ml of saturated ammonium sulfate (in $H_2O$) is added dropwise with stirring. After overnight incubation at 4° C., the precipitate is pelleted by centrifugation at 17,000×g for 15 minutes, and the supernatant fraction is discarded. The pellet is resuspended in 2 ml PBS. The resulting fraction is clarified by centrifugation at 13,500×g for 5 minutes and passage through a 0.45 µm filter (Nylon 66, 13 mm diameter, Micron Separations, Inc., Westborough, Mass.). Two ml (about half) of the clarified fraction is applied to a Sephacryl® S-200 column (1.6×51 cm; 0.25 ml/min PBS+0.1% sodium azide) (Pharmacia, Piscataway, N.J.), and 2 ml fractions are collected. Those fractions found to have the highest concentrations of dIgA (by SDS-PAGE analysis of 10 µl of each fraction) are lyophilized, resuspended in 200 µl deionized $H_2O$, and applied to a Superose® 6 column (1.0×30 cm; 0.25 ml/min PBS+0.1% sodium azide) (Pharmacia, Piscataway, N.J.). One ml fractions are collected and analyzed by SDS-PAGE. Fraction 13 is found to contain dIgA at over 90% purity.

Preparation of J chain by mild reduction of dIgA. A 1 ml sample containing less than 10 mg of dIgA is prepared as described above and dialyzed against buffer containing 100 mM sodium phosphate pH 6.0 and 5 mM EDTA. Six mg 2-mercaptoethylamine HCl are added to yield a final concentration of 0.05M, and the sample is incubated at 37° C. for 90 minutes. The reduced protein is passed over a desalting column equilibrated in PBS+1 mM EDTA. The protein-containing fractions are detected by assay with BCA reagent. J chain is then further purified by gel filtration and ion exchange chromatography.

Preparation of secretory IgA (sIgA). One hundred ml of human breast milk (Lee Scientific, Inc., St. Louis, Mo.) is mixed with 100 ml PBS and centrifuged at 17,000×g for 1 hour at 4° C. The clear layer below the fat is transferred to clean centrifuge bottles and centrifuged at 17,000×g for 30 minutes at 4° C. The pH of the sample is adjusted to 4.2 with 2% acetic acid. After incubation at 4° C. for 1 hour, the sample is centrifuged at 17,000×g for 1 hour at 4° C., and the supernatant fraction is transferred to new tubes and adjusted to pH 7 with 0.1 M NaOH. An equal volume of saturated ammonium sulfate is added, with stirring, and the sample is incubated at 4° C. overnight. The precipitated material is pelleted by centrifugation (17,000×g, 90 minutes, 4° C.), resuspended in approximately 7 ml PBS, and dialyzed extensively against PBS at 4° C.

Of the resulting approximately 25 ml, 1.1 ml is further purified. Undissolved solids are removed by centrifugation (13,500×g, 10 minutes) and an equal volume of 0.05 M $ZnSO_4$ is added to the clarified supernatant fraction. The pH is adjusted to 6.85 by addition of approximately 40 µl 1 M NaOH. After allowing the material to sit for 5 minutes at room temperature, the sample is centrifuged at 13,500×g for 10 minutes at room temperature. One and a half ml of the supernatant is mixed with 1.5 ml of saturated ammonium sulfate and allowed to stand at 4° C. for 1 hour. Precipitating material is pelleted by centrifugation (13,500×g, 10 minutes, room temperature) and is found to be greater than 90% sIgA by SDS-PAGE analysis.

Preparation of a molecule consisting of nicked J-chain crosslinked to two alpha-chain-derived peptides (CNBr cleavage fragment). A pellet containing sIgA prepared as described above ("Preparation of sIgA") is resuspended in 375 µl deionized $H_2O$. The sample is transferred to a glass vial and the vial is filled almost to the rim with 875 µl formic acid. Approximately 20 mg solid CNBr is added and a Teflon septum is used to seal the vial. The reaction is allowed to proceed at 4° C. overnight. The sample is then dialyzed against deionized $H_2O$ (two changes) and against PBS at 4° C., and lyophilized, resuspended with 200 µl $H_2O$, and applied to a Superose® 6 column (1.0×30 cm, 0.25 ml/min PBS+0.1% sodium azide). One ml fractions are collected. The fractions containing J chain are identified by immunoblotting of SDS-PAGE-separated proteins from aliquots of each fraction.

The fraction with the highest concentration of J chain is passed through a PD-10 column (Pharmacia, Uppsala, Sweden) equilibrated in 50 mM Tris-CL pH 8.1, and applied to a 20 PI Poros anion exchange column (4.6 mm×100 mm; PerSeptive Biosystems, Inc., Framingham, Mass.). The column is washed with 10 ml of 50 mM Tris-Cl pH 8.1, and eluted with a linear 0-1.0 M NaCl gradient in 50 mM Tris-Cl pH 8.1 (15 ml gradient). Elution of proteins from the column is monitore d as absorbance at 280 nm and the J chain-containing fractions are identified by immunoblotting of SDS-PAGE-separated aliquots.

Alternative Methods for J Chain Purification. A variety of sources are suitable as starting material for isolation of human J chain. Polymeric IgA from sera of patients with IgA multiple myeloma, secretory IgA or IgM from sera of patients with Waldenstroms macroglobulinemia, as well as secretory IgA from human breast milk can be used as starting material for purification of J chain. Although the differences in the molecular weights of J chain (16,000) and L chains (22,500) should be large enough to allow satisfactory separation of these two chains by gel filtration, the unique conformation of J chain and its ability to dimerize often results in co-elution of J chain with L chain. Isolation procedures take advantage of J chain's negative charge (due to the high content of aspartic and glutamic acid residue) further increased by S-sulfitolysis or alkylation of reduced cysteine residues with iodoacetic acid. J chain can be subsequently separated from H and L chains by DEAE- or CM-cellulose chromatography using a linear salt gradient or by preparative electrophoresis in the presence or absence of dissociating agents.

Purification on DEAE-cellulose, which results in the isolation of immunochemically and physicochemically homogeneous J chain. As a starting material, the J chain-containing L chain fraction of polymeric IgA, S-IgA, or IgM, obtained by partial oxidative sulfitolysis and subsequent gel filtration on Sephadex® G-200 in 5 M guanidine-HCl can be used. Alternatively, S-sulfonated IgA or S-IGA can be directly applied on DEAE-cellulose. However, it is usually necessary to perform an additional separation using gel filtration on Sephadex® G-200 in 5 M guanidine-HCl to remove contaminating H chains.

Starting materials consist of the following reagents: L chain fraction of serum polymeric IgA or IgM, or colostral S-IgA; 0.01 M disodium phosphate in deionized 8 M urea solution and the same buffer with 0.7 M NaCl; DEAE-cellulose equilibrated in 0.01 M disodium phosphate containing 8 M urea; Sephadex® G-25 column in 1% $NH_4HCO_3$ solution.

Lyophilized L chain fraction is dissolved in 0.01 M disodium phosphate in 8 M urea, and applied on a DEAE-cellulose column equilibrated in the same phosphate solution. The column is thoroughly washed with this buffer. Absorbed proteins are eluted with a linear gradient of 0.01 M disodium phosphate in 8 M urea and 0.01 M disodium phosphate with 0.7 M NaCl. Two fractions are obtained, the later fraction containing J chain.

The J chain-containing fraction is desalted on a Sephadex® G-25 column in 1% $NH_4HCO_3$ adjusted to neutrality by bubbling with $CO_2$. The purity of J chain can be assessed by alkaline-urea gel-electrophoresis or immunoelectrophoresis with anti-L, H, and J chain reagents.

B. Direct Synthesis of TM Polypeptides

Manual syntheses are performed with BOC-L-amino acids purchased from Biosearch-Milligen (Bedford, Mass.). Machine-assisted syntheses are performed with BOC-L-amino acids from Peptide Institute (Osaka, Japan) and Peptides International (Louisville, Ky.). BOC-D-amino acids are from Peptide Institute. BOC-L-His(DNP) and BOC-L-Aba are from Bachem Bioscience (Philadelphia, Pa.). Boc-amino acid-(4-carboxamidomethyl)-benzyl-ester-copoly (styrene-divinylbenzene) resins [Boc-amino acid-OCH2-Pam-resins] are obtained from Applied Biosystems (Foster City, Calif.) and 4-methylbenzhydrylamine (4Me-BHA) resin is from Peninsula Laboratories, Inc. (Belmont, Calif.). Diisopropylcarbodiimide (DIC) is from Aldrich, and 2-(IH-benzotriazol-t-yl)-1,1,3,3-tetramethyluronium-hexafluorophosphate (HBTU) is obtained from Richelieu Biotechnologies (Quebec, Canada). For manual syntheses N,N-diisopropylethylamine (DIEA), N,N-dimethylformamide (DMF), dichloromethane (DCM) (all peptide synthesis grade) and 1-hydroxybenzotriazole (HOBT) are purchased from Auspep (Melbourne, Australia). For machine-assisted syntheses, DIEA and DCM are from ABI, and DMF is from Auspep. Trifluoroacetic acid (TFA) is from Halocarbon (New Jersey). Acetonitrile (HPLC grade) is obtained from Waters Millipore (Milford, Mass.). HF is purchased from Mallinckrodt (St. Louis, Mo.). Other reagents and solvents are ACS analytical reagent grade. Screw-cap glass peptide synthesis reaction vessels (20 mL) with a # 2 sintered glass filter frit are obtained from Embel Scientific Glassware (Queensland, Australia). A shaker for manual solid phase peptide synthesis is obtained from Milligen (Bedford, Mass.). An all-Kel F apparatus (Toho; from Peptide Institute, Osaka) is used for HF cleavage. Argon, helium and nitrogen (all ultrapure grade) are from Parsons (San Diego, Calif.).

Chain assembly. Syntheses are carried out on Boc-amino acid-OCH2-Pam-resins, or on 4-MeBHA-resin. Boc amino acids are used with the following side chain protection: Arg(Tos); Asp(OBzl) (manual synthesis) and Asp(OcHxl); Cys(Bzl) (machine-assisted synthesis); Asn, unprotected (manual synthesis) and Asn(Xan) (machine-assisted synthesis); Glu(OcHxl); His(DNP); Lys(2CIZ); Thr(Bzl); Trp(InFormyl); and Tyr(BrZ). Gln and Met are used side chain unprotected.

Manual protocol. Syntheses are carried out on a 0.2 mmol scale. The $N^\alpha$-Boc group is removed by treatment with 100% TFA for 2×1 minute followed by a 30 second flow with DMF. Boc amino acids (0.8 mmol) are coupled, without prior neutralization of the peptide-resin salt, as active esters preformed in DMF with either HOBt/DIC (30 minute activation), or HBTU/DIEA (2 minute activation) as activating agents. For couplings with active esters formed by HOBt/DIC, neutralization is performed in situ by adding 1.5 equivalents of DIEA relative to the amount of TFA $O^-.^+$ NH3-peptide-resin salt to the activated Boc-amino acid/resin mixture. For couplings with active esters formed from HBTU/DIEA, an additional 2 equivalents DIEA relative to the amount of TFA $O^-.^+$NH3-peptide-resin salt are added to the activation mixture. Coupling times are 10 minutes throughout without any double coupling. Samples (3-5 mg) of peptide-resin are removed after the coupling step for determination of residual free Boc-amino groups by the quantitative ninhydrin method. Coupling yields are typically >99.9%. All operations are performed manually in a 20 mL glass reaction vessel with a Teflon-lined screw cap. The peptide-resin is agitated by gentle inversion on a shaker during the NII-deprotection and coupling steps.

Deprotection and cleavage. H is(DNP)-containing peptides are treated with a solution of 20% mercaptoethanol/ 10% DIEA in DMF for 2×30 minutes in order to remove the DNP group, prior to the removal of the Boc group. The $N^\alpha$-Boc group is removed from the peptide-resin by treatment with neat TFA (2×1 minute). The peptide-resin is washed with DMF and neutralized with 10% DIEA in DMF (1×1 minute). After removal of the DNP and Boc group, the peptide-resin is treated with a solution of ethanolamine in water/DMF for 2×30 minutes to remove the formyl group of Trp(InFormyl).

The partially-deprotected peptide-resin is dried under reduced pressure after washing with DMF and DCM. Side chain protecting groups are removed and simultaneously the peptide is cleaved from the resin by treatment with HF/p-cresol (9:1 v/v, 0° C., 1 hour) or HF/p-cresol/thiocresol (9:0.5:0.5 by vol., 0° C., 1 hour). The HF is removed under reduced pressure at 0° C. and the crude peptide precipitated and washed with ice-cold diethyl ether, then dissolved in either 20% or 50% aqueous acetic acid, diluted with $H_2O$ and lyophilized.

Peptide joining. Joining of peptide segments of TM produced by the synthetic procedures described above is carried out by chemical ligation of unprotected peptides using previously described procedures (Baca, et al., *J.A.C.S.* 117:1881-1887, 1995; Dawson, et al., *Science* 266:776-779, 1994). These procedures can yield a free sulfhydryl at the junctional peptide bond or can yield a disulfide bond. Alternatively, cysteine residues at specified positions are replaced by L-aminobutyric acid.

In one procedure, a synthetic segment peptide 1, which contains a thioester at the α-carboxyl group, undergoes nucleophilic attack by the side chain thiol of the Cys residue at the amino terminus of peptide 2. The initial thioester ligation product undergoes rapid intramolecular reaction because of the favorable geometric arrangement (involving a five-membered ring) of the α-amino group of peptide 2, to yield a product with the native peptide bond of a cysteine moiety at the ligation site. Both reacting peptide segments are in completely unprotected form, and the target peptide is obtained in final form without further manipulation. Additional cysteine residues in either peptide 1 or peptide 2 are left in their reduced state. The procedure is referred to herein as native chemical ligation.

In another procedure, unprotected peptide segments are ligated via nucleophilic attack of a deprotonated α-thioacid group on a bromoacetyl moiety to form a dimer chemically ligated via thioester. In addition, C terminal cysteamine moieties can be joined to N-terminal mercaptoacetyl groups after derivatization of the cysteamine-containing monomer with 2,2'-dipyridyl disulfide. A disulfide-linked dimer is formed by thiolysis of the S-(2-pyridylsulfenyl) cysteamine derivative.

These procedures are used to derive a variety of TM configurations, such as the representative TMs provided below. The TM core consists of residues 12-101 and the extended TM consists of residues 1-136.

TABLE II

Direct Synthesis of TM Polypeptides

| Segments | Chemistry | Strategy to form Closed Covalent Loop | Representative Attachment Sites |
|---|---|---|---|
| A. TM Core | | | |
| 1. 12-71 | N-cysteine C-glyNH$_2$CH$_2$CH$_2$SH | 71 to 91 via disulfide linker; 12 to 101 via | sulfhydryls at 14 and 68 |

TABLE II-continued

Direct Synthesis of TM Polypeptides

| Segments | Chemistry | Strategy to form Closed Covalent Loop | Representative Attachment Sites |
|---|---|---|---|
| 2. 91-101 | N-glyCOCH$_2$SH<br>C-cysteine | renaturation and oxidation to disulfide | |
| B. TM Core | | | |
| 1. 31-71 | N-BrCH$_2$CO<br>C-glyNH$_2$CH$_2$CH$_2$SH | 71 to 91 via disulfide linker; 30 to 31 via thioester; 12 to 101 exists as peptide bonds (serine-glycine-alanine in place of cys to cys disulfide) | sulfhydryls at 14 and 68 |
| 2. 91-[101-12]-30 | N-glyCOCH$_2$SH<br>C-thioacid | | |
| C. TM Extended | | | |
| 1. 1-67 | N—NH3+<br>C-thioester | 67 to 68 via native chemical ligation; 118 to 119 via thioester; 71 to 91, 12 to 101 and 108 to 133 via renaturation and oxidation to form disulfides | sulfhydryls at 14 and 68 |
| 2. 68-118 | N-cysteine<br>C-thioacid | | |
| 3. 119-136 | N-BrCH$_2$CO<br>C—COO— | | |
| D. TM Core Variations | | | |
| 1. serine 68<br>serine 14 | Same as A or B<br>Same as A or B | Same as A or B<br>Same as A or B | sulfhydryl at 14;<br>sulfhydryl at 68; |
| 2. serine 68 +<br>serine 14 | Same as A or B | Same as A or B | free amines or free carboxyls |
| E. TM Extended Variations | | | |
| 1. 1-70 | N—NH3+<br>C-thioester | 70 to 71 via native chemical ligation; 118 to 119 via thioester; 71 to 91, 12 to 101 and 108 to 133 via renaturation and oxidation to form disulfides; serines at 14 and 68 | reactive group at 136 for attachment of N-mercapto-acetylated peptide linker |
| 71-118 | N-cysteine<br>C-thioacid | | |
| 119-136 | N-BrCH$_2$CO<br>C-glyNH$_2$CH$_2$CH$_2$SH | | |
| 2. 1-70 | N-BrCH$_2$CO<br>C-thioester | 70 to 71 via native chemical ligation; 118 to 119 via thioester; 71-91, 12 to 101 and 108 to 133 via renaturation and oxidation to form disulfides; serines at 14 and 68 | reactive group at 1 for attachment of C-thioester peptide linker |
| 71-118 | N-cysteine<br>C-thioacid | | |
| 119-136 | N-BrCH$_2$CO<br>C—COO— | | |

"Extended" = a TM comprising the 88 residues of the core, plus an additional 48 residues derived from native J chain;
"Core" = residues 12-101 of native J chain;
residues are indicated according to the numbering in FIG. 1

C. Synthesis and Expression of Synthetic DNAs Encoding TM

DNA chains can be synthesized by the phosphoramidite method, which is well known in the art, whereby individual building block nucleotides are assembled to create a desired sequence. Automated DNA synthesis of TM DNAs involves the synthesis and joining of individual oligonucleotides encoding portions of TMs to form the entire desired sequence. Synthetic DNA can be purchased from a number of commercial sources.

Transgenic expression of TMs requires ligation of the synthetic coding DNA into a vector for transformation of the appropriate organism. Techniques of ligation into vectors are well described in the literature. For example, in order to enable the introduction and expression of TMs in insect cells, the synthetic TM DNA is ligated into the pFastBac1 vector (GibcoBRL) to form the pFastBac1-TM recombinant. The recombinant vector is then used to transform *E. coli* bacteria containing a helper plasmid and a baculovirus shuttle vector. High molecular weight shuttle vector DNA containing transposed TM coding sequences is then isolated and used for transfection of insect cells. Recombinant baculovirus are harvested from transfected cells and used for subsequent infection of insect cell cultures for protein expression.

A TM can be synthesized by expressing in cells a DNA molecule encoding the TM. The DNA can be included in an extrachromosomal DNA element or integrated into the chromosomal DNA of the cell expressing the TM. Alternatively, the TM DNA can be included as part of the genome of a DNA or RNA virus which directs the expression of the TM in the cell in which it is resident. An example of a DNA sequence encoding TM is shown in SEQ ID NO:7. This DNA sequence and the amino acid sequence (SEQ ID NO:17) encoded by this TM DNA are also shown in Table III.

One method of synthesizing such a TM gene involves the sequential assembly of oligonucleotides encoding portions of the TM gene into a complete TM gene. The final assembly of the TM gene can occur in a DNA expression vector suitable for expression in a cellular system, or the TM gene can be constructed in a convenient cloning vector and subsequently moved into a DNA expression vector suitable for expression in a cellular system. An advantage of the sequential assembly of the TM gene from partial coding regions is the ability to generate modified versions of the TM gene by using alternative sequences for one or more of its individual portions during the assembly of the TM gene. Alternatively, the restriction endonuclease sites encoded in the TM gene can be used after the assembly of part or all of the TM gene to replace portions of the TM coding sequence to generate alternative TM coding sequences, using well known techniques, as described by Sambrook et al., *Molecular Cloning: A Laboratory Manual*, 2d ed., Cold Spring Harbor Laboratory, Cold Spring Harbor, N.Y., 1989. The TM gene can be divided into several partial coding regions: D1 encoding amino acids approximately -2 to 20; C2 encoding amino acids approximately 19 to 66; L3 encoding amino acids approximately 65 to 102; and T4 encoding amino acids approximately 102 to 142 of the sequence recited in Table III. Unless otherwise indicated, references to amino acid residue numbers in the following section are to the residue indicated in Table III.

Assembly of a synthetic gene encoding TM Core polypeptide. A TM Core gene sequence may be defined by the combination of C2, D1.1 (a modified version of D1, and L3Δ (a modified version of L3). One version of TM Core may be generated from the oligonucleotides 1.1, 2.1, 3, 4, 5, 6, 7, 8, 9L3Δ and 10L3Δ (SEQ ID NOS:48, 49, 54-56, 58, 60, 61, 63, 64) listed in Table IV and encodes a polypeptide of sequence:

DQKCKCARITSRIIRSSEDPNEDI-VERNIRIIVPLNNRENISDPTSPLRTRFVYHLSD LCK-KDEDSATETC (Table IX and SEQ ID NO:18). A gene containing D1.1, C2, and L3Δ or alternate coding sequences that differ only in conservative substitutions or modifications is a complete TM Core gene.

Assembly of C2. In one example, de novo synthesis of a TM gene (including the TM core) may be initiated by assembly of a partial gene, called C2, encoding amino acids 19-66 of the TM. The sequence of C2 DNA and the peptide sequence encoded by the C2 DNA are shown in Table V and SEQ ID NOS:9 and 19. C2 is generated by annealing oligonucleotides 3, 4, 5, 6, 7 and 8 (SEQ ID NOS:54, 55, 56, 58, 60, and 61, respectively) of Table IV into a DNA fragment encoding approximately 48 amino acids of the TM Core polypeptide. Oligonucleotide pairs 3&4, 5&6, and 7&8 are first annealed pairwise into overlapping DNA duplexes, and the 3 double stranded DNAs are then annealed together to form a double stranded DNA complex composed of the 6 individual oligonucleotides. Oligonucleotides 1 and 8 have overhanging unpaired ends compatible with the unpaired ends of DNA restricted with the enzymes Xba I and Bgl II, respectively. C2 is annealed into the vector pMelBac XP, at the Xba I and Bgl II restriction endonuclease sites of the multiple cloning region and the DNA fragments enzymatically ligated to form the vector pTMC (Method 1).

Method 1: Synthesis of C2 DNA from oligonucleotides and insertion into pMelBac XP to form pTMC. Individual oligonucleotides 3, 4, 5, 6, 7, and 8 (SEQ ID NOS:54-56, 58, 60, 61) are separately dissolved in TE buffer (Sambrook et al., *Molecular Cloning: A Laboratory Manual,* 2d ed., Cold Spring Harbor Laboratory, Cold Spring Harbor, N.Y., 1989) at a concentration of 1 mM (1 nanomole/microliter). Two nanomoles of each oligonucleotide are combined with the same amount of its pair (e.g., (3&4), (5&6) or (7&8)) in 10 μL of annealing buffer (10 mM Tris pH 8.0, 100 mM NaCl, 1 mM EDTA) in a microcentrifuge tube, and the tubes immersed in 50 mL boiling water for 5 minutes. The entire boiling water bath, including microcentrifuge tubes, is then removed from the heat source and allowed to cool to room temperature (approximately 24° C.), allowing the oligonucleotides to form base-paired DNA duplexes. After incubating for 30 minutes at room temperature, 1 nanomole of each oligonucleotide pairs (e.g., (3&4), (5&6), and (7&8)) are combined in a single microcentrifuge tube. The tube containing these DNA duplexes is incubated at 55° C. for 15 minutes in a heating block, removed from the heating block and equilibrated to room temperature, allowing overlapping complementary regions of the DNA duplexes to anneal, forming a DNA duplex encoding the partial TM DNA C2.

One nanomole of the oligonucleotide duplex is then mixed with 0.1 picomole of pMelBac XP which has previously been restricted with endonucleases Xba I and Bgl II. pMelBac XP is a DNA vector for cloning and subsequent expression in insect cells of synthetic TM genes, derived from pMelBac B (Invitrogen, San Diego, Calif.). The sequence of the secretion signal and multiple cloning site is (SEQ ID NOS:42 and 43):

met lys phe leu val asn val ala leu val phe met val tyr
atg aaa ttc tta gtc aac gtt gcc ctt ttt atg gtc gta tac
ile ser tyr ile tyr ala asp pro ser ser ser ala
att tct tac atc tat gcg gat ccg agc tcg agt gct cta ga
tct gca gct ggt acc atg gaa ttc gaa gct tgg agt cga ctc
tgc tga The mixture of vector DNA and synthetic gene fragment is then heated to 35° C. for 15 minutes, then 1/10 volume of Ligation Stock Buffer is added, DNA ligase is added and the reaction mixture incubated at 12° C. for 12 hours to ligate the phosphodiester bonds among oligonucleotides and vector DNA, as described in Sambrook et al., *Molecular Cloning. A Laboratory Manual,* 2d ed., Cold Spring Harbor Laboratory, Cold Spring Harbor, N.Y., 1989. DNA is then used for transfection of competent *E. coli* cells by standard methods (see Sambrook et al. supra). Plasmid DNA is isolated from these cells and is evaluated by restriction endonuclease digestion or DNA sequencing to evaluate the success of synthetic DNA assembly and cloning. The resulting plasmid, pTMC is then used as a framework for successive addition of synthetic TM sequences.

Assembly of D1.1 and insertion into the TM synthetic gene. A fragment of the TM DNA proximal to C2, called D1.1, encodes amino acids 9 to 20 of the TM. The DNA sequence and primary amino acid peptide sequence of D1.1 are shown in Table VI and SEQ ID NOS:10 and 20. D1.1 encodes the proximal amino acids of the TM Core polypeptide (residues 12 to 20) as well as a short peptide of three amino acids which serve to join the TM Core with a leader peptide (appropriate for the expression system employed for synthesis of TM). D1.1 is generated by annealing oligonucleotides 1.1 and 2.1 (SEQ ID NOS:48 and 49 respectively) into a DNA duplex as described in Method 1. Oligonucleotides 1.1 and 2.1 have overhanging unpaired ends compatible with the unpaired ends of BamHI (or Bgl II) and Xba I, respectively. D1.1 is annealed into pTMC at the BamHI and Xba I restriction endonuclease sites of the multiple cloning region and the DNA fragments enzymatically ligated, in a manner similar to that described in Method 1 for pTMC, to form the vector pTMD1.1C.

Assembly of L3Δ and insertion into the TM synthetic gene. A fragment of the TM DNA distal to C2, called L3Δ, encodes a contiguous polypeptide of amino acids 66-70 and 92-101 of the TM provided in Table III. The DNA sequence and peptide sequence of L3 are shown in Table VII and SEQ ID NOS:11 and 21. L3Δ is generated by annealing oligonucleotides 9L3Δ and 10L3Δ (SEQ ID NOS:63 and 64, respectively) into a DNA duplex as described in Method 1 to generate the distal portion of the TM Core DNA encoding approximately 14 amino acids. Oligonucleotides 9L3Δ and 10L3Δ have overhanging unpaired ends compatible with the unpaired ends of Bgl II and EcoRI, respectively. L3Δ is ligated into the vector pTMD1.1C at the Bgl II and EcoRI restriction endonuclease sites and the DNA fragments enzymatically ligated, in a manner similar to that described in Method 1 for pTMC, to form the vector pTMCore.

A TM may also be synthesized as described above, except that L3 (discussed below) is used in place of L3Δ. The sequence of such a TM is provided in Table X and SEQ ID NO:13.

Assembly of a synthetic gene encoding a full length TM polypeptide. A full length TM gene sequence may be defined by the combination of D1, C2, L3 and T4. One example of a full length TM gene (SEQ ID NO:7) is generated from the oligonucleotides 1, 2, 3, 4, 5, 6, 7, 8, 9, 10, 11, 12, 13, 14, 15, and 16 (SEQ ID NOS:46, 47, 54-56, 58, 60-62, 73-79, respectively) listed in Table IV. A gene containing D1, C2, L3, and T4 or coding sequences that differ only in conservative substitutions or modifications is a full length TM gene.

Assembly of D1 and insertion into the TM synthetic gene. A fragment of the TM DNA proximal to C2, called D1, encodes amino acids −2 to 20 of the TM. The DNA sequence and peptide sequence of D1 are shown in Table VI.A and SEQ ID NOS:15 and 25. D1 encodes the proximal amino acids of the TM Core polypeptide (residues 12 to 20) as well as a peptide of 13 amino acids which serves to join the TM Core with a leader peptide (appropriate for the expression system employed for synthesis of TM). D1 is generated by annealing oligonucleotides 1 and 2 (Table IV). Oligonucleotides 1 and 2 have overhanging unpaired ends compatible with the unpaired ends of BamHI (or Bgl II) and Xba I, respectively. D1 is annealed into pTMC at the BamHI and Xba I restriction endonuclease sites of the multiple cloning region and the DNA fragments enzymatically ligated, in a manner similar to that described in Method 1 for pTMC, to form the vector pTMDC.

Assembly of L3 and insertion into the TM synthetic gene. A fragment of the TM DNA distal to C2, called L3, encodes amino acids 66-101 of TM. The DNA sequence and peptide sequence of L3 are shown in Table VII.A and SEQ ID NOS:14 and 24. L3 is generated by annealing oligonucleotides 9, 10, 11, and 12 (SEQ ID NOS:62, 73-75, respectively) (Table IV) into a DNA duplex to generate the distal portion of the TM Core DNA encoding approximately 35 amino acids. Oligonucleotide pairs 9 & 10 and 11 & 12 are first annealed together to form a double stranded DNA complex composed of the 4 individual oligonucleotides. Oligonucleotides 9 and 12 have overhanging unpaired ends compatible with the unpaired ends of Bgl II and Pst I, respectively. L3 is annealed into the vector pTMDC at the Bgl II and PstI restriction endonuclease sites and the DNA fragments enzymatically ligated, in a manner similar to that described in Method 1 for pTMC, to form the vector pTMDCL.

Assembly of T4 and insertion into the TM synthetic gene. A fragment of the TM DNA distal to L3, called T4, encodes amino acids 102-141 of the TM. The DNA sequence and peptide sequence of L4 are shown in Table VIII and SEQ ID NOS:12 and 22. L3 is generated by annealing oligonucleotides 13, 14, 15, and 16 (SEQ ID NOS:76-79, respectively) (Table IV) into a DNA fragment which is the distal portion of the full length TM DNA encoding approximately 36 amino acids. Oligonucleotide pairs 13&14 and 15&16 are first annealed pairwise into overlapping DNA duplexes, and the two double stranded DNAs are subsequently annealed together to form a double stranded DNA complex composed of the 4 individual oligonucleotides. Oligonucleotides 13 and 16 have overhanging unpaired ends compatible with the unpaired ends of Pst I and EcoRI, respectively. T4 is annealed into the vector pTMDCL at the Pst I and Eco RI restriction endonuclease sites and the DNA fragments enzymatically ligated, in a manner similar to that described in Method 1 for pTMC, to form the vector pTM.

Assembly of synthetic genes encoding modified TM polypeptides. Other versions of TM genes, in which the peptide sequence is altered from the full length TM or TM Core, can be synthesized by using alternative oligonucleotides to 1, 2, 3, 4, 5, 6, 7, 8, 9, 10, 11, 12, 13, 14, 15, or 16 (SEQ ID NOS:46, 47, 54-56, 58, 60-62, 73-79, respectively) listed in Table IV. These alternative oligonucleotides can be employed during synthesis of a partial TM gene, or can be used to generate DNA fragments which can replace coding sequences in an assembled TM gene or TM gene fragment by removing DNA fragments with restriction endonucleases, and replacing the original sequence with an alternative coding sequence. In addition, DNA sequences encoding polypeptides unrelated to TM can be inserted into the TM coding sequences at various positions.

Assembly of a synthetic gene encoding an aglycosylated TM polypeptide. In one example oligonucleotides 5 and 6 are replaced during the assembly of C2 with oligonucleotides 5.1dg and 6.1dg (SEQ ID NOS:57 and 59) (Table IV) to form a new fragment called C2Δglyco. This oligonucleotide substitution results in an altered C2 DNA sequence so that the asparagine encoded at residue 48 is changed to a histidine. With the exception of the oligonucleotides 5.1dg and 6.1dg, C2Δglyco is created in the same manner as C2. C2Δglyco can be used in the synthesis of a variety TM sequences in a manner similar to that described for TM Core and full length TM sequences.

Assembly of a synthetic gene encoding a TM polypeptide with a modified L3 domain. In another example, TM amino acid residues 71-91 are replaced with the three amino acid peptide: ser-asp-ile. In this example oligonucleotides 9.2Δ3 and 10.2Δ3 (SEQ ID NOS:67 and 68) (Table IV) are first annealed into a DNA duplex and subsequently annealed into the vector pTMDC at the Bgl II and Eco RI restriction endonuclease sites. The annealed DNA fragments are then enzymatically ligated to form the vector pTMLΔ3.

Assembly of synthetic genes encoding a TM polypeptide with cysteine residue 68 replaced. In other examples, the oligonucleotide pairs 9.3Δ3ser&10.3Δ3ser (SEQ ID NOS: 69 and 70) or 9.3Δ3val&10.3Δ3val (SEQ ID NOS:71 and 72) are annealed into DNA duplexes and digested with the enzyme ClaI and subsequently annealed into pTMLΔ3 which has been digested with restriction enzymes ClaI and PstI. These two oligonucleotide pairs, when inserted into pTM1Δ3, result in a TMΔ3 molecule with the cysteine at position 68 replaced by serine or valine, respectively.

Assembly of synthetic genes encoding a TM polypeptide with cysteine residue 14 replaced. In another example the oligonucleotide pairs 1.2ser&2.2ser (SEQ ID NOS:50 and 51) or 1.2val&2.2val (SEQ ID NOS:52 and 53) can be annealed to generate an alternative domain to D1 with the cysteine residue 14 replaced with serine or valine, respectively. These oligonucleotide pairs are then annealed, in the same manner as described above for D1, into pTMC at the BamHI and Xba I restriction endonuclease sites of the multiple cloning region and the DNA fragments enzymatically ligated to form alternatives to the vector pTMD1C.

Assembly of a synthetic gene encoding a TM core polypeptide containing an endomembrane retention signal. In a further example TM core is synthesized with the endomembrane retention signal KDEL (SEQ ID NO:44) as the carboxyterminal amino acid residues. In this example oligonucleotides 9L3ΔKDEL and 10L3ΔKDEL (SEQ ID NOS:65 and 66) are substituted for oligonucleotides 9L3Δ and 10L3Δ during synthesis of TM core described above to form the vector pTMLΔ3KDEL.

Assembly of a synthetic gene encoding a full length TM polypeptide containing an endomembrane retention signal. In another example TM is synthesized with the endomembrane retention signal KDEL (SEQ ID NO:44) as the carboxyterminal amino acid residues. In this example oligonucleotides 15 KDEL and 16 KDEL (SEQ ID NOS:80 and 81) are substituted for oligonucleotides 15 and 16 as described above for synthesis of T4. The substitution of these two oligonucleotides results in the formation of coding sequence T4 KDEL which when substituted for T4 in the above described synthesis of p™ results in the formation of the vector pTMKDEL.

Assembly of a synthetic gene encoding a TM polypeptide containing an additional amino terminal sequence. In one example a TM gene is synthesized with the polyimmunoglobulin receptor sequence from residues 585-600 (AIQDPRLFAEEKAVAD; SEQ ID NO:45) included as part of the amino terminal domain. The oligonucleotides P1 and P2 (SEQ ID NOS:82 and 83) encode this polyimmunoglobulin receptor sequence and amino acid residues of D1. P1 and P2 have overhanging unpaired ends compatible with the unpaired ends of Bam HI and XbaI, respectively. The oligonucleotides P1 and P2 are annealed into a DNA duplex which can be used in place of D1.1 or D1 in the synthesis of a TM expression vectors as described above.

Assembly of a synthetic gene encoding a TM polypeptide in which a component of TM is replaced by another peptide domain, TpS2. In this example, a TM gene is synthesized with a peptide replacing TM Domains 4, 5 and 6. This peptide, referred to as TpS2, encodes an enterokinase cleavable peptide between the terminal residue of Domain 2 and the coding sequence for the trefoil peptide pS2 (as reported in Suemori et al., *Proc. Natl. Acad. Sci.* 88:11017-11021, 1991). The DNA sequence and peptide sequence of TpS2 are shown in Table XI and SEQ ID NOS:16 and 26. TpS2 is generated by annealing oligonucleotides Tp1, Tp2, Tp3, Tp4, Tp5 and Tp6 (SEQ ID NOS:103-108, respectively) (Table IV) into a DNA fragment which encodes approximately 64 amino acids. Oligonucleotide pairs Tp1 & Tp2, Tp3 & Tp4 and Tp5 & Tp6 are first annealed pairwise into overlapping DNA duplexes, and the two double stranded DNAs are subsequently annealed together to form a double stranded DNA complex composed of the 6 individual oligonucleotides. Oligonucleotides Tp1 and Tp6 have overhanging unpaired ends compatible with the unpaired ends of PstI and EcoRI restriction sites, respectively. TpS2 is annealed into the vector pTMDCL at the PstI and EcoRI restriction endonuclease sites and the DNA fragments enzymatically ligated, in a manner similar to that described in Method 1 for pTMC, to form a vector pTMpSp2, which encodes a TM with the trefoil peptide pS2 included as a replacement for TM Domains 4, 5, and 6.

D. Isolation and Expression of cDNA Encoding Human J Chain.

Two human small intestine cDNA libraries (Clontech Laboratories, Palo Alto, Calif.; cat #HL1133a and dHL1133b) are screened using a synthetic DNA complementary to the 5' end of the human J chain messenger RNA. The probes are labeled with [$^{32}$P] using polynucleotide kinase in standard reactions. The library screening is performed as described by the manufacturer (Clontech). Hybridization is carried out according to Church and Gilbert, *Proc. Natl. Acad. Sci. USA* 81:1991-1995, 1984. After autoradiography, positive plaques are isolated and the phage are disrupted by boiling for 10 minutes. The cDNA inserts are amplified by PCR in a total volume of 50 μL containing standard PCR buffer, 25 pmoles of primers complementary to the 5' and 3' ends of the human J chain cDNA, 200 μM of each dNTP, and 1.0 unit of Taq polymerase. The DNA is denatured for 3 minutes at 94° C. prior to 35 cycles of amplification. Each cycle consisted of 1 min at 94° C., 1 min at 62° C., and 1 min at 72° C. The PCR fragments are cloned into pUC19 and sequenced. Full length cDNA inserts are then subcloned into the appropriate insect expression vector (pMelBacXP) utilizing restriction sites placed in the two PCR primers.

TABLE III

DNA Sequence and Primary Amino Acid Structure of a Representative Full Length TM Molecule

| -2 | -1 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| *asp* | *gln* | *glu* | *asp* | *glu* | *arg* | *ile* | *val* | *leu* | *val* | *asp* | *asn* | *lys* | *cys* | *lys* | *cys* | *ala* | *arg* |
| gat | cag | gaa | gat | gaa | cgt | att | gtt | ctg | gtt | gac | aac | aag | tgc | aag | tgt | gct | cgt |
| cta | gtc | ctt | cta | ctt | gca | taa | caa | gac | caa | ctg | ttg | ttc | acg | ttc | aca | cga | gca |

| 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|
| *ile* | *thr* | *ser* | *arg* | *ile* | *ile* | *arg* | *ser* | *ser* | *glu* | *asp* | *pro* | *asn* | *glu* | *asp* | *ile* | *val* | *glu* |
| att | act | tct | aga | atc | atc | cgt | agc | tca | gag | gac | cca | aat | gaa | gat | ata | gtc | gaa |
| taa | tga | aga | tct | tag | tag | gca | tcg | agt | ctc | ctg | ggt | tta | ctt | cta | tat | cag | ctt |

| 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|
| *arg* | *asn* | *ile* | *arg* | *ile* | *ile* | *val* | *pro* | *leu* | *asn* | *asn* | *arg* | *glu* | *asn* | *ile* | *ser* | *asp* | *pro* |

TABLE III-continued

DNA Sequence and Primary Amino Acid Structure of a Representative Full Length TM Molecule

```
cgt aac atc cgt atc atc gtc cca ctg aat aac cgg gag aat atc tca gat cct
gca ttg tag gca tag tag cag ggt gac tta ttg gcc ctc tta tag agt cta gga 53  54  55  56  57  58  59  60  61  62  63  64  65  66  67  68  69  70
thr ser pro leu arg thr arg phe val tyr his leu ser asp leu cys lys lys
aca agt ccg ttg cgc aca cgc ttc gta tac cac ctg tca gat ctg tgt aag aag
tgt tca ggc aac gcg tgt gcg aag cat atg gtg gac agt cta gac aca ttc ttc 71  72  73  74  75  76  77  78  79  80  81  82  83  84  85  86  87  88
cys asp pro thr glu val glu leu asp asn gln ile val thr ala thr gln ser
tgt gat cca aca gag gta gag ctg gac aat cag ata gtc act gcg act caa agc
aca cta ggt tgt ctc cat ctc gac ctg tta gtc tat cag tga cgc tga gtt tcg 89  90  91  92  93  94  95  96  97  99 100 101 102 103 104 109 110 111
asn ile cys asp glu asp ser ala thr glu thr cys ser thr tyr asp arg asn
aac att tgc gat gag gac agc gct aca gaa acc tgc agc acc tac gat agg aac
ttg taa acg cta ctc ctg tcg cga tgt ctt tgg acg tcg tgg atg cta tcc ttg 112 113 114 115 116 117 118 119 120 121 122 123 124 125 126 127 128 129
lys cys tyr thr ala val val pro leu val tyr gly gly glu thr lys met val
aaa tgc tac acg gcc gtg gtt ccg ctc gtg tat ggt gga gag aca aaa atg gtg
ttt acg atg tgc cgg cac caa ggc gag cac ata cca cct ctc tgt ttt tac cac 130 131 132 133 134 135 136 137 138 139 140 141
glu thr ala leu thr pro asp ala cys tyr pro asp OPA
                                              (SEQ ID NO:17)

gaa act gcc ctt acg ccc gat gca tgc tat ccg gac tga attc
                                              (SEQ ID NO:7)

ctt tga cgg gaa tgc ggg cta cgt acg ata ggc ctg act taag
                                              (SEQ ID NO:27)
```

TABLE IV

Oligonucleotides for Construction of Representative Partial TM Genes

| OLIGO | SEQUENCE |
|---|---|
| 1: | gat cag gaa gat gaa cgt att gtt ctg gtt gac aac aag tgc aag tgt gct cgt att act t |
| 2: | cta gaa gta ata cga gca cac ttg cac ttg ttg tca acc aga aca ata cgt tca tct tcc t |
| 1.1: | gat cag aag tgc aag tgt gct cgt att act t |
| 2.1: | ct aga agt aat acg agc aca ctt gca ctt ct |
| 1.2ser: | gat cag gaa gat gaa cgt att gtt ctg gtt gac aac aag tgc aag tgc gct cgt att act t |
| 2.2ser: | cta gaa gta ata cga gcg gac ttg cac ttg ttg tca acc aga aca ata cgt tca tct tcc t |
| 1.2val: | gat cag gaa gat gaa cgt att gtt ctg gtt gac aac aag tgc aag gtt gct cgt att act t |
| 2.2val: | cta gaa gta ata cga gca acc ttg cac ttg ttg tca acc aga aca ata cgt tca tct tcc t |
| 3: | cta gaa tca tcc gta gct cag agg acc caa atg aag ata tag tcg aa |
| 4 | gat acg gat gtt acg ttc gac tat atc ttc att tgg gtc ctc tga gct acg gat gat t |
| 5: | cgt aac atc cgt atc atc gtc cca ctg aat aac cgg gag aat atc tca g |
| 5.1dg: | cgt aac atc cgt atc atc gtc cca ctg aat aac cgg gag cac atc tca g |
| 6: | acg gac ttg tag gat ctg aga tat tct ccc ggt tat tca gtg gga cga t |
| 6.1dg: | acg gac ttg tag gat ctg aga tgt gct ccc ggt tat tca gtg gga cga t |
| 7: | atc cta caa gtc cgt tgc gca cac gct tcg tat acc acc tgt ca |
| 8: | gat ctg aca ggt ggt ata cga agc gtg tgc gca |
| 9: | gat ctg tgt aag aag tgt gat cca aca gag gta gag ctg gac aat cag ata gtc act gca |
| 9L3Δ: | gat ctg tgt aag aag gat gag gac agc gct aca gaa acc tgc tg |
| 10L3Δ: | aat tca gca ggt ttc tgt agc gct gtc ctc atc ctt ctt aca ca |
| 9L3ΔKDEL: | gat ctg tgt aag aag gat gag gac agc gct aca gaa acc tgc tac gag aag gat gag ctg tg |
| 10L3ΔKDEL: | aat tca cag ctc atc ctt ctc gta gca ggt ttc tgt agc gct gtc ctc atc ctt ctt aca ca |
| 9.2Δ3: | gat ctg tgt aag aag tct gat atc gat gaa gat tcc gct aca gaa acc tgc agc aca tg |

TABLE IV-continued

Oligonucleotides for Construction of Representative Partial TM Genes

| OLIGO | SEQUENCE |
|---|---|
| 10.2Δ3: | aat tca tgt gct gca ggt ttc tgt agc gga atc ttc atc gat atc aga ctt ctt aca ca |
| 9.3Δ3/ser68: | gat ctg tct aag aag tct gat atc gat gaa gat tac aga ttc ttc aga cta tag cta ctt cta a |
| 10.3Δ3/ser68: | aat ctt cat cga tat cag act tct tag aca |
| 9.3Δ3/val68: | gat ctg gtt aag aag tct gat atc gat gaa gat tac caa ttc ttc aga cta tag cta ctt cta a |
| 10.3Δ3/val68: | aat ctt cat cga tat cag act tct taa cca |
| 10: | att gtc cag ctc tac ctc tgt tgg atc aca ctt ctt aca ca |
| 11: | act caa agc aac att tgc gat gag gac agc gct aca gaa acc tgc a |
| 12: | ggt ttc tgt agc gct ctg ctc atc gca aat gtt gct ttg agt cgc agt gac tat ctg |
| 13: | gc acc tac gat agg aac aaa tgc tac acg gcc gtg gtt ccg ctc gtg tat ggt gga gag |
| 14: | gag cgg aac cac ggc cgt gta gca ttt gtt cct atc gta ggt gct gca |
| 15: | aca aaa atg gtg gaa act gcc ctt acg ccc gat gca tgc tat ccg gac tg |
| 16: | aat tca gtc cgg ata gca tgc atc ggg cgt aag ggc agt ttc cac cat ttt tgt ctc tcc acc ata cac |
| 15KDEL: | aca aaa atg gtg gaa act gcc ctt acg ccc gat gca tgc tat ccg gac aag gat gaa ttg tg |
| 16KDEL: | aat tca caa ttc atc ctt gtc cgg ata gca tgc atc ggg cgt aag ggc agt ttc cac cat ttt tgt ctc tcc acc ata cac |
| P1: | gat cag gtc gct gcc atc caa gac ccg agg ctg ttc gcc gaa gag aag gcc gtc gct gac tcc aag tgc aag tgt gct cgt att act t |
| P2: | ct aga agt aat acg agc aca ctt gca ctt gga gtc agc gac ggc ctt ctc ttc ggc gaa cag cct cgg gtc ttg gat ggc agc gac ct |
| Tp1: | gc gat gac gac gat aag gcc caa acg gag acc tgt act gtt gcg cct cgt gaa cgg caa aac tgc gga ttc ccg gga |
| Tp2: | gtt ttg ccg ttc acg agg cgc aac agt aca ggt ctc cgt ttg ggc ctt atc gtc gtc atc gct gca |
| Tp3: | gta aca ccc tct cag tgc gct aat aaa ggc tgc tgt ttt gat gac acg gta cgg ggc gtt ccg tgg tgc ttc |
| Tp4: | gcc ccg tac cgt gtc atc aaa aca gca gcc ttt att agc gca ctg aga ggg tgt tac tcc cgg gaa tcc gca |
| Tp5: | tac ccc aat aca att gac gtt ccg cct gaa gaa gag tgc gag ttt taa g |
| Tp6: | aattc tta cgg ctc gca ctc ttc ttc agg cgg caa gtc aat tgt att ggg gta gaa gca cca aaa aac |

TABLE V

Peptide and DNA sequence of Domain C2 of TM (TM aa residues 19-65)

```
 19  20  21  22  23  24  25  26  27  28  29  30  31  32  33  34  35  36
ser arg ile ile arg ser ser glu asp pro asn glu asp ile val glu arg asn
>>>>>>>>>>>>>>>>>>>>>>> oligo #3 >>>>>>>>>>>>>>>>>>>>>>>>>>>>>>>/>>>>>>>
 ct aga atc atc cgt agc tca gag gac cca aat gaa gat ata gtc gaa cgt aac
 t tag tag gca tcg agt ctc ctg ggt tta ctt cta tat cag ctt gca ttg
<<<<<<<<<<<<<<<<<<<<< oligo #4 <<<<<<<<<<<<<<<<<<<<<<<<<<<<<<<<<

37  38  39  40  41  42  43  44  45  46  47  48  49  50  51  52  53  54
ile arg ile ile val pro leu asn asn arg glu asn ile ser asp pro thr ser
>>>>>>>>>>>>>>>>>>>> oligo #5 >>>>>>>>>>>>>>>>>>>>>>>/>>>>>>>>>>>>
atc cgt atc atc gtc cca ctg aat aac cgg gag aat atc tca gat cct aca agt
tag gca tag tag cag ggt gac tta ttg gcc ctc tta tag agt cta gga tgt tca
<<<<<<<< oligo #6 <<<<<<<<<<<<<<<<<<<<<<<<<<<<<<<<<<<<<<<<<<<<<<

55  56  57  58  59  60  61  62  63  64  65  66     amino acid number
pro leu arg thr arg phe val tyr his leu ser asp leu  amino acid
                                   (SEQ ID NO:19)
>>>>>>>>>>> oligo #7 >>>>>>>>>>>>>>>>>>>>>>>           coding strand oligo
ccg ttg cgc aca cgc ttc gta tac cac ctg tca           coding strand
                                   (SEQ ID NO:9)
ggc aac gcg tgt gcg aag cat atg gtg gac agt cta g     noncoding strand
                                   (SEQ ID NO:29)
<<<</<<<<<< oligo #8 <<<<<<<<<<<<<<<<<<<<<<<<<        noncoding strand
                                                           oligo
```

TABLE VI

DNA sequence and primary amino acid structure of Domain D1.1 of TM (TM aa residues 9-20)

```
  9  10  11  12  13  14  15  16  17  18  19  20
asp gln lys cys lys cys ala arg ile thr ser arg (SEQ ID NO:20)
>>>>>>>>>>> oligo D1.1>>>>>>>>>>>>>>>>>>>>>
gat cag aag tgc aag tgt gct cgt att act t (SEQ ID NO:10)
    tc ttc acg ttc aca cga gca taa tga aga tc (SEQ ID NO:30)
       <<<<<<<<<<<<<< oligo D2.1<<<<<<<<<<<<<<
```

TABLE VI.A

DNA sequence and primary amino acid structure of Domain D1 of TM (TM aa residues -2-20)

```
 -2  -1   1   2   3   4   5   6   7   8   9  10  11  12  13  14  15
asp gln glu asp glu arg ile val leu val asp asn lys cys lys cys ala
gat cag gaa gat gaa cgt att gtt ctg gtt gac aac aag tgc aag tgt gct
tc  ctt cta ctt gca taa caa gac caa ctg ttg ttc acg ttc aca cga 16  17  18  19  20
arg ile thr ser arg (SEQ ID NO:25)
cgt att act t       (SEQ ID NO:15)
gca taa tga aga tc  (SEQ ID NO:35)
```

TABLE VII

Peptide and DNA sequence of Domain L3Δ of TM (TM aa residues 66-70 and 92-101)

```
 66  67  68  69  70  92  93  94  95  96  97  99 100 101
asp leu cys lys lys asp glu asp ser ala thr glu thr cys OPA
                                                          (SEQ ID NO:21)
gat ctg tgt aag aag gat gaa gat tcc gct aca gaa acc tgc tg
                                                          (SEQ ID NO:11)
    ac aca ttc ttc cta ctt ctc agg cga tgt ctt tgg acg act taa
                                                          (SEQ ID NO:31)
```

TABLE VII.A

Peptide and DNA sequence of Domain L3 of TM (TM aa residues 66-101)

```
 66  67  68  69  70  71  72  73  74  75  76  77  78  79  80  81
asp leu cys lys lys cys asp pro thr glu val glu leu asp asn gln
gat ctg tgt aag aag tgt gat cca aca gag gta gag ctg gac aat cag
cta gac aca ttc ttc aca cta ggt tgt ctc cat ctc gac ctg tta gtc 82  83  84  85  86  87  88  89  90  91  92  93  94  95  96  97
ile val thr ala thr gln ser asn ile cys asp glu asp ser ala thr
ata gtc act gcg act caa agc aac att tgc gat gag gac agc gct aca
tat cag tga cgc tga gtt tcg ttg taa acg cta ctc ctg tcg cga tgt 100
glu thr cys
gaa acc tgc  (SEQ ID NO:24)
ctt tgg acg  (SEQ ID NO:14)
             (SEQ ID NO:34)
```

TABLE VIII

DNA and Primary Amino Acid Sequence of T4 Fragment (TM aa residues 102-141)

```
    102 103 104 109 110 111 112 113 114 115 116 117 118 119 120 121
    ser thr tyr asp arg asn lys cys tyr thr ala val val pro leu val
     gc acc tac gat agg aac aaa tgc tac acg gcc gtg gtt ccg ctc gtg
acg tcg tgg atg cta tcc ttg ttt acg atg tgc cgg cac caa ggc gag cac
```

TABLE VIII-continued

DNA and Primary Amino Acid Sequence of T4 Fragment (TM aa residues 102-141)

| 122 | 123 | 124 | 125 | 126 | 127 | 128 | 129 | 130 | 131 | 132 | 133 | 134 | 135 | 136 | 137 | 138 |
|---|---|---|---|---|---|---|---|---|---|---|---|---|---|---|---|---|
| *tyr* | *gly* | *gly* | *glu* | *thr* | *lys* | *met* | *val* | *glu* | *thr* | *ala* | *leu* | *thr* | *pro* | *asp* | *ala* | *cys* |
| tat | ggt | gga | gag | aca | aaa | atg | gtg | gaa | act | gcc | ctt | acg | ccc | gat | gca | tgc |
| ata | cca | cct | ctc | tgt | ttt | tac | cac | ctt | tga | cgg | gaa | tgc | ggg | cta | cgt | acg |

| 139 | 140 | 141 | | |
|---|---|---|---|---|
| *tyr* | *pro* | *asp* | *OPA* | (SEQ ID NO:22) |
| tac | cct | gac | tg | (SEQ ID NO:12) |
| atg | gga | ctg | act | taa (SEQ ID NO:32) |

TABLE IX

DNA Sequence and Primary Amino Acid Sequence of a Representative TM Core Element

| 9 | 10 | 11 | 12 | 13 | 14 | 15 | 16 | 17 | 18 | 19 |
|---|---|---|---|---|---|---|---|---|---|---|
| *asp* | *gln* | *lys* | *cys* | *lys* | *cys* | *ala* | *arg* | *ile* | *thr* | *ser* |
| gat | cag | aag | tgc | aag | tgt | gct | cgt | att | act | tct |
| cta | gtc | ttc | acg | ttc | aca | cga | gca | taa | tga | aga |

| 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|
| *arg* | *ile* | *ile* | *arg* | *ser* | *ser* | *glu* | *asp* | *pro* | *asn* | *glu* | *asp* | *ile* | *val* | *glu* | *arg* | *asn* |
| aga | atc | atc | cgt | agc | tca | gag | gac | cca | aat | gaa | gat | ata | gtc | gaa | cgt | aac |
| tct | tag | tag | gca | tcg | agt | ctc | ctg | ggt | tta | ctt | cta | tat | cag | ctt | gca | ttg |

| 37 | 38 | 39 | 40 | 41 | 42 | 43 | 44 | 45 | 46 | 47 | 48 | 49 | 50 | 51 | 52 | 53 |
|---|---|---|---|---|---|---|---|---|---|---|---|---|---|---|---|---|
| *ile* | *arg* | *ile* | *ile* | *val* | *pro* | *leu* | *asn* | *asn* | *arg* | *glu* | *asn* | *ile* | *ser* | *asp* | *pro* | *thr* |
| atc | cgt | atc | atc | gtc | cca | ctg | aat | aac | cgg | gag | aat | atc | tca | gat | cct | aca |
| tag | gca | tag | tag | cag | ggt | gac | tta | ttg | gcc | ctc | tta | tag | agt | cta | gga | tgt |

| 54 | 55 | 56 | 57 | 58 | 59 | 60 | 61 | 62 | 63 | 64 | 65 | 66 | 67 | 68 | 69 | 70 |
|---|---|---|---|---|---|---|---|---|---|---|---|---|---|---|---|---|
| *ser* | *pro* | *leu* | *arg* | *thr* | *arg* | *phe* | *val* | *tyr* | *his* | *leu* | *ser* | *asp* | *leu* | *cys* | *lys* | *lys* |
| agt | ccg | ttg | cgc | aca | cgc | ttc | gta | tac | cac | ctg | tca | gat | ctg | tgt | aag | aag |
| tca | ggc | aac | gcg | tgt | gcg | aag | cat | atg | gtg | gac | agt | cta | gac | aca | ttc | ttc |

| 92 | 93 | 94 | 95 | 96 | 97 | 99 | 100 | 101 | | |
|---|---|---|---|---|---|---|---|---|---|---|
| *asp* | *glu* | *asp* | *ser* | *ala* | *thr* | *glu* | *thr* | *cys* | *OPA* | Eco RI (SEQ ID NO:18) |
| gat | gag | gac | agc | gct | aca | gaa | acc | tgc | tg | (SEQ ID NO:8) |
| cta | ctc | ctg | tcg | cga | tgt | ctt | tgg | acg | act | taa (SEQ ID NO:28) |

TABLE XI

DNA and Primary Amino Acid Sequence of TpS2

```
101                                                                         102
cys ser asp asp asp asp lys ala gln thr glu thr cys thr val ala pro
    gc  gat gac gac gat aag gcc caa acg gag acc tgt act gtt gcg cct
   acg  tcg cta ctg ctg cta ttc cgg gtt tgc ctc tgg aca tga caa cgc gga
arg glu arg gln asn cys gly phe pro gly val thr pro ser gln cys ala
cgt gaa cgg caa aac tgc gga ttc ccg gga/gta aca ccc tct cag tgc gct
gca ctt gcc gtt ttg/acg cct aag ggc cct cat tgt ggg aga gtc acg cga
asn lys gly cys cys phe asp asp thr val arg gly val pro trp cys phe
aat aaa ggc tgc tgt ttt gat gac acg gta cgg ggc gtt ccg tgg tgc ttc/
tta ttt ccg acg aca aaa cta ctg tgc cat gcc ccg/caa ggc acc acg aag
tyr pro asn thr ile asp val pro pro glu glu glu cys glu phe
tac ccc aat aca att gac gtt ccg cct gaa gaa gag tgc gag ttt taa g
atg ggg tta tgt taa ctg caa ggc gga ctt ctt ctc acg ctc aaa att
cttaa --
```

Example 2

Linkage of Biological Agents to a TM

This example illustrates the attachment of representative biological agents to a TM.

A. Preparation of an Anti-Influenza Virus Single Chain Antigen Binding Protein (SCABP) Attached to TM A TM containing a full length native J chain domain may be attached to Cα3-Fv(γ+κ)-anti-influenza virus SCABP.

Virus culture. Influenza virus A/Puerto Rico/8-Mount Sinai is grown in fertilized chicken eggs and concentrated and purified by differential centrifugation. Virus is quantified in a plaque assay on Madin-Darby canine Kidney (MDCK) cells and, when desired, is inactivated with 0.05% β-propiolactone plus 6 minutes of UV irradiation 20 cm from a germicidal lamp.

Production and characterization of anti-influenza virus MAbs. IgA and IgG anti-influenza virus MAbs are produced by a mucosal immunization protocol. Briefly, BALB/c mice are immunized intragastrically four times over an 8-week period, the first three times with 0.5 mg of inactivated influenza virus plus 10 μg of cholera toxin (List Biological Laboratories, Inc. Campbell, Calif.). For the last immunization, cholera toxin is omitted and in addition to intragastric virus administration, mice also receive an intravenous booster immunization with 30 μg of inactivated virus. Three days later, mice are sacrificed and their splenic lymphocytes are hybridized to SP2/0 murine myeloma cells. Clones are screened for secretion of IgA and IgG anti-influenza virus antibody by an enzyme-linked immunosorbent assay (ELISA). After multiple subclonings, stable IgA secretors are injected intraperitoneally into pristane primed Balb-C mice and the ascitic fluid is harvested and the specificities of the MAbs are confirmed by Western blotting techniques. The biological activities of the MAbs are characterized by determining an ELISA titer, neutralization titer, and hemagglutination inhibition activity.

Isolation of mRNAs and Synthesis of cDNAs. mRNA derived from cell lines producing IgA antibodies is isolated by established procedures using the FastTrack™ mRNA isolation kit (Invitrogen). Specific primers are employed to prime polymerase chain reactions resulting in the amplification of the Fvγ section, the Cα3 section, and the Fvκ section in separate amplification reactions.

Fv heavy forward primers (SEQ ID NO:84):
  5' TGGTACGAATTCCAGGT(G/C)(A/C)A(A/G)CTG-CAG(G/C)AGTC (A/G)G Fv heavy back primer (SEQ ID NO:85):
  5' ACAGATATCGGGATTTCTCGCAGACTC The forward primer is 32-fold degenerate as indicated by the nucleotides in parentheses. The back primer encodes the first six amino acid of the CH1 constant region of the alpha chain.

Cα3 forward primer (SEQ ID NO:86):
  5' ACAGATATCGTGAACACCTTCCCACCC

Cα3 back primer (SEQ ID NO:87):
  5' ACAAAGCTTTTATTTACCCGACAGACGGTC

The stop codon for the hybrid transcript is contained in the Cα3 back primer.

Fvκ forward primers (SEQ ID NO:88):
  5' GTCCCCCCTCGAGCGA(T/C)AT(T/C)(C/G)(A/T)G (C/A)T(G/C) ACCCA(A/G)TCT Fvκ back primer (SEQ ID NO:89):
  5' ACACTGCAGCAGTTGGTGCAGCATCAGC Linker segment (SEQ ID NO:90):
  5' CTGCAGGAAGCGGAAGCGGAGGAAGCG-GAAGCGGAGGAA GCGGAAGCGAATTC The linker segment is synthesized using a PerSeptive Biosystems 8909 DNA Synthesizer and encodes glycine and serine residues which enable the proper folding of the antibody variable regions in the final protein. Sequences at the termini enable ligation into the PstI and EcoRI sites of pBluescript. The linker segment is first annealed with the following complementary DNA prior to ligation into the vector (all other DNAs derived from PCR are double stranded and restricted with the appropriate enzyme prior to ligation).

Linker complement (SEQ ID NO:91):
  5' CCTTCGCCTTCGCCTCCTTCGCCTTCGC-CTCCTTCGCCTTCGCT TAA Similarly, a signal peptide segment to enable translation of the final protein into the endomembrane system of the insect cell is synthesized, annealed to its complement and ligated into the BamH1 and Sma1 sites of pBluescript.

Signal peptide (SEQ ID NO:92):
  5' ACAGGATCCATGGAAACCCCAGCG-CAGCTTCTCTTCCTCCTGC TACTCTGGCTC-CCAGATACCACCGGACCCGGG The TM segment, synthesized by the phosphoramidite method so as to contain cysteines at positions 14 and 68, also contains SacII and SpeI restriction sites at its 5' and 3' end respectively. It is ligated directly into the p2Bac™ vector (Invitrogen). The ligation reactions are performed essentially as described in Sambrook et al. The other segments are first ligated into pBluescript in the following order: linker segment (PstI/EcoRI), Fvκ (SmaI/PstI), Fvγ (EcoRI/EcoRV), Cα3 (EcoRV/HindIII). The hybrid cDNA is excised from the bacterial vector by BamHI and HindIII restriction enzyme digestion, gel purification and ligated into the p2Bac™ vector (Invitrogen) at the BglII and HindIII sites. After cloning, the plasmids containing cDNAs in the appropriate orientation are isolated and used for transformation of insect cells as described above.

The resulting (Fvκ-linker-Fvγ-Cα3)$_2$:TM (anti-HA-TM) protein containing two κγα segments per TM, joined by disulfide bridges at the Cys14 and Cys68 residues of TM, is purified by column chromatography essentially as described above. Additional amino acids are incorporated into the fusion protein at the DNA junction points as follows (the dash indicates the fusion site of the individual segments): Pro-Gly at the SmaI site, Pro-Ala at the PstI site, Glu-Phe at the EcoRI site, and Asp-Ile at the EcoRV site.

As a control Fvκ-linker-Fvγ-Cα3 (anti-HA) is separately purified from insect cells which do not co-express TM.

B. Preparation of Functional Genes Attached to TM

Preparation of TM-polylysine conjugates. TM isolated from biological sources as described above, is covalently linked to poly (L-lysine) (Mr 20,000 D) using the heterobifunctional crosslinking reagent N-succinimidyl 3-(2-pyridyldithio) proprionate (SPDP) as previously described (Ferkol, et al., *J. Clin. Invest.* 92:2394-2400, 1993). After reduction of the SPDP, TM is incubated with a fifteenfold molar excess of poly (L-lysine)-SPDP and the reaction is carried out at 2° C. for 24 hours. The conjugate is dialyzed to remove low molecular weight reaction products, and analyzed by separating the resultant proteins using 0.1% SDS-7.5% polyacrylamide gel electrophoresis.

Reporter genes and plasmid preparation. The plasmids PRSVZ and PRSVCAT, containing the Escherichia coli lacZ and chloramphenicol acetyltransferase genes, respectively, ligated to the Rous sarcoma virus long terminal repeat promoter inserted into a modified pBR322 vector, are used as reporter genes. The plasmids are grown in E. coli DH5α, extracted and purified by standard techniques. Digestions of the plasmids with restriction endonucleases yields the appropriate fragments, and purity is established by 1.0% agarose gel electrophoresis.

Preparation of TM-Polylysine-DNA Complexes. Complexes are Formed by combining plasmid DNA with the TM-polylysine in 3M NaCl. The charge ratio of the DNA phosphate to lysine is ~1.2:1. Samples are incubated for 60 minutes at 22° C., then dialyzed against 0.15 NaCl for 16 hours through membranes with a 3,500-dalton molecular mass limit. The complexes are filtered through a Millipore filter with 15 μm pore size, and maintained at 4° C. prior to use.

Determination of optimal conjugate to DNA proportion. To determine the optimal proportion of conjugate to DNA, increasing amounts of the conjugate are added to 10 μg of PRSVZ, producing 1:4, 1:8, 1:16, and 1:32 DNA to carrier (TM) molar ratios. Samples are incubated as described above, and dialyzed overnight against 0.15 M NaCl. The complexes are filtered before use. Samples containing equal amounts of DNA (1 Hg) are separated by 1.0% agarose gel electrophoresis and stained with ethidium bromide. The plasmid DNA is transferred onto a nitrocellulose filter and analyzed by Southern blot hybridization, using the 2,3-kB EcoRI fragment of PRSVZ as a DNA probe.

C. Preparation of an Anti-C. Difficile Toxin A Attached to TM

Cells and cultures. Cell media, culture, fusion procedures, and ascites production to obtain monoclonal antibodies (MAbs) are as described by Harlow and Lane, "Antibodies: A Laboratory Manual," Cold Spring Harbor Laboratory, Cold Spring Harbor, N.Y., 1988. Mice receive subcutaneously 4.5 μg of inactivated toxin (4% Formalin for 1 week at 4° C.) with Freund's complete adjuvant (at days −200, −190, and −120). On days −30 and −4, they receive by the same route 200 ng of native toxin without adjuvant. On the day of fusion, after hemisplenectomy, spleen cells are fused with SP2Ø myeloma cells. Screening procedures began 10 days later with the neutralization assay, enzyme immunoassay, and immunoblot procedures described below. Subcloning is done by the limiting dilution method, and typing of MAbs is done by using a mouse MAb isotyping kit (Amersham).

Approximately 10% hybridomas are found to produce antibodies that react with toxin A by immunoblot and by ELISA. Ascites are produced with the most interesting clones (after the subcloning procedure) and analyzed for immunoreactivity with native toxin A.

Toxin A (partially purified after acid precipitation as described by Towbin et al., Proc. Natl. Acad. Sci. USA 76:4350-4354, 1979) is neutralized by ascites fluid as follows. The dose of toxin A used is adjusted to cause 100% mortality within 24 hours postinoculation (about 1 ng per mouse). The toxin is mixed with MAb ascites (final dilution 1:3), incubated for 1 hour at 37° C., and injected intraperitoneally into mice (five animals per group). Survival is determined 15 hours later. For the toxin A antibody ELISA, microtiter wells are coated with 0.5 μg of native toxin A overnight in carbonate buffer, pH 9.6. Wells are washed, and 0.1 ml of ascites fluid is added for 1 hour and then serially diluted. Wells are washed and goat anti-mouse IgG (whole molecule)-alkaline phosphatase conjugate (1:1,000) is added. Wells are washed and incubated with para-nitrophenol phosphate (Sigma 104 tablets; Sigma Chemical Co., St. Louis, Mo.) in ethanolamine buffer (pH 9.8). The absorbance at 405 nm is determined after 1 hour at room temperature. Wells that give an $A_{405}$ value two times higher than background are considered positive.

Titers correspond to the $\log_{10}$ of the highest dilution of sample which had an optical density of twice the background. Sodium dodecyl sulfate (SDS)—PAGE is done by the method of Laemmli. Samples are subsequently transferred to nitrocellulose as described by Towbin et al. and screened with 1:3 dilutions of hybridoma tissue culture or ascites fluids, followed by the addition of a 1:500 dilution of goat anti-mouse IgG (whole molecule)-horseradish peroxidase conjugate. Staining is done with diaminobenzidene (5 mg/mL) and hydrogen peroxide. Double agar diffusion (1.59% agar concentration) is performed with crude *C. difficile* supernatant containing toxin A (1 mg/ml) and ascites fluid (diluted 1:10). Positive reactions are observed 2 days later.

Isolation of mRNAs and Synthesis of cDNAs. mRNA derived from cell lines producing IgG antibodies is isolated by established procedures using the FastTrack™ mRNA isolation kit (Invitrogen). Specific linkers are employed to prime polymerase chain reactions resulting in the amplification of the Fv-Cγ1 section, and the entire κ chain in separate amplification reactions.

Heavy chain forward primer (SEQ ID NO:93):

5' TGGTACAGATCTAGGT(G/C)(A/C)A(A/G)CTG-CAG(G/C)AGTC (A/G)G

Heavy chain back primer (SEQ ID NO:94):

5' ACAGAATTCAATTTTCTTGTCCACCTT

The forward primer is 32-fold degenerate as indicated by the nucleotides in parentheses. The back primer encodes the last six amino acids of the $C_H1$ constant region of the gamma chain. The kappa chain is amplified in its entirety.

Kappa forward primers (SEQ ID NO:95):

5' GTTCTAGAGA(T/C)AT(T/C)(C/G)(A/T)G(C/A)T(G/C)ACCCA(A/G) TCT

Kappa back primer (SEQ ID NO:96):

5' ACACCGCGGCAGTTGGTGCAGCATCAGC

A signal peptide segment enabling translation of the final protein into the endomembrane system of the insect cell is synthesized, annealed to its complement and ligated into the BamHI and BglII sites of p2Bac™ vector (Invitrogen) heavy chain-TM expression and into to SpeI and XbaI sites of p2Bac™ for expression of the kappa chain.

Signal peptides:

Heavy chain (SEQ ID NO:97)

5' ACAGGATCCATGGAAACCCCAGCG-CAGCTTCTCTTCCTCCTG CTACTCTGGCTC-CCAGATACCACCGGAAGATCT

Light chain (SEQ ID NO:98)

5' ACAACTAGTATGGAAACCCCAGCG-CAGCTTCTCTTCCTCCTG CTACTCTGGCTC-CCAGATACCACCGGATCTAGA

The TM segment, synthesized by the phosphoramidite method to contain serines at positions 14 and 68, also contains EcoRI and HindIII restriction sites at its 5' and 3' end respectively. A stop codon is included in the proper reading frame to halt translation of the fusion transcript.

The segments are ligated directly into the p2Bac vector in the following order for the heavy chain-TM fusion: signal sequence (BamHI-BglI), heavy chain segment (BglII-EcoRI), TM segment (EcoRI-HindIII). The order for the kappa chain: signal sequence (SpeI-XbaI), kappa chain (Xba-SacII).

The resulting heavy chain (Fv, $C_H1$)-TM:kappa chain hybrid protein (anti-*C. difficile*-TM) joined by disulfide bridges through the constant regions of the heavy and light chains, is purified by column chromatography essentially as described above. Additional amino acids are incorporated into the fusion protein at the DNA junction points as follows (the dash indicates the fusion site of the individual segments): Arg-Ser at the BglII site, Glu-Phe at the EcoRI site, Ser-Arg at the XbaI site.

D. Preparation of TM with Various Linkers to Fluorescent Compounds or Anticancer Drugs.

General method for fmoc synthesis of peptide linkers. Reactions were generally performed at the 0.2 mmol scale and follow previously described procedures (M. Bodanszky, A. Bodanszky, The Practice of Peptide Synthesis, Springer-Verlag, Berlin, 1984; M. Bodanszky, Peptide Chemistry; A Practical Textbook, Springer-Verlag, Berlin, 1988). Coupling reactions were initiated at the carboxy terminus using a protected amino acid (amino acid #1) immobilized to a p-alkoxybenzyl alcohol resin (e.g., Fmoc-Lys(Boc)-resin, Peninsula Laboratories (Belmont, Calif.) product #FM058AAR, 0.2-0.5 meq/g). Protecting groups for the primary amines comprised the 9-fluorenylmethyloxycarbonyl group, fmoc. R group protection (e.g., trityl, t-butyl, butoxycarbonyl, acetamidomethyl, ethylthio) depended on the nature of the R group. Reactions were carried out in a funnel containing a scintered glass filter (e.g., Kimax #28400-301) fitted with a two way stopcock. The fmoc protecting group on amino acid #1 was first removed by incubation in 20% piperidine in dimethylformamide (DMF) for 15 minutes at room temperature. Piperidine was then washed out with excess DMF. Fmoc protected amino acid #2 (1 mmol) dissolved in minimal DMF (~1 ml) was added to the resin followed by the addition of 1 mmol hydroxybenzotriazole also dissolved in minimal DMF. Coupling was initiated by the addition of 1 mmol diisopropylcarbodiimide. The reaction was allowed to proceed at room temperature with gentle shaking for 1 hour. The resin was then washed with excess DMF to remove all reagents. The efficiency of the reaction was monitored using a standard ninhydrin assay (Pierce product #21205). The procedures were then repeated (i.e., deprotect, wash, couple, wash) for the addition of each amino acid comprising the desired sequence. The final peptide was removed from the resin by incubation at room temperature for 1-3 hours in 95% TFA containing water and scavengers (e.g., triisoproylsilane, ethanedithiol, thioanisole, bromotrimethylsilane). This procedure removes all R-group protection as well. Peptide was precipitated from the TFA solution by the addition of 4 volumes of diethyl ether, the peptide pellet was redissolved in DMF, and purified by reverse phase liquid chromatography.

Fluorescent compound with a scissile linker attachment to synthetic TM. The polyimmunoglobulin receptor sequence from residues 585-600 (AIQDPRLFAEEKAVAD; SEQ ID NO:45), which is the substrate for an intracellular processing protease, is synthesized by peptide coupling as described above. The peptide is synthesized from a Gly-thioester resin support yielding a C terminal Gly-αCOSH after cleavage. Prior to release from the column, the amino terminus of the peptide is reacted with NHS-fluorescein (1 mmol dissolved in 1 ml DMF) (Pierce product #46100). The peptide is then released from the column to yield a fluoresceinated amino terminus and a reactive thioester group at the carboxy end. The fluoresceinated peptide (10 μmol) is attached to TM (1 μmol) by reaction of the peptidyl thioester group with bromoacteyl group at residue 1 of TM (structure E #2, Table II). The derivatized TM is then purified from the reaction mixture by column chromatography (NAP-10 column, Pharmacia). This compound is referred to as TM-peptide-FL. Control preparations are performed in identical fashion except the synthetic peptide linker has no cleavage site: VAVQSAGTPASGS (SEQ ID NO:99).

Fluorescent compound with a scissile linker attachment to purified dimeric IgA The peptide was synthesized with an additional cysteine residue at the C terminus to yield the sequence AIQDPRLFAEEKAVADC (SEQ ID NO:45). Prior to release from the column, the amino terminus of the peptide is reacted with NHS-fluorescein (1 mmol dissolved in 1 ml DMF) (Pierce product #46100). The peptide is then released from the column to yield a fluoresceinated amino terminus and a reactive sulfhydryl group at the carboxy end. Dimeric IgA (100 nmol) purified from biological sources as described above is reacted with sulfosuccinimidyl 4-[N-maleimidomethyl]cyclohexane-1-carboxylate (sulfo-SMCC, 10 μmol, Pierce product #22322) according to the manufacturers protocol. The compound reacts with free amino groups via the sulfosuccinimidyl moiety and thereby attaches a reactive maleimide group for reaction with free sulfhydryls. The dIgA-SMCC derivative is purified from the reaction mixture by column chromatography in 25 mM phosphate buffer, pH 6.8, containing 1 mM EDTA (NAP-10 column, Pharmacia). The purified dIgA in ~1 ml buffer is immediately reacted with the fluoresceinated peptide containing a free sulfhydryl group (10 μmol dissolved in 200 μl DMF) for 12 hours at 4° C. The derivatized dIgA is then purified from the reaction mixture by column chromatography (NAP-10 column, Pharmacia). This compound is referred to as dIgA-peptide-FL. Control preparations are performed in identical fashion except the synthetic peptide linker has no cleavage site: VAVQSAGTPASGS (SEQ ID NO:99).

Anti-cancer drug attached to TM via a scissile peptide and a pH-sensitive hydrazide linker. 3-deamino-3-(4-morpholinyl)-doxorubicin (MRA) is prepared from doxorubicin (Aldrich, Milwaukee, Wis.) by reaction via dialdehyde, followed by a reaction with sodium cyanoborohydrate as previously described (Mueller et al., *Antibody, Immunoconjugates, and Radiopharmaceuticals* 4:99-106, 1991). MRA is purified after separation on a silica gel column, and is modified with a peptide spacer by the following procedure. First, the peptide PLGIIGG (SEQ ID NO: 109) is esterified to yield the corresponding methyl ester. This is followed by condensation of the amino terminal of the peptide with succinic anhydride, followed by reaction of the ester terminal with hydrazine hydrate to yield the monohydrazide. The hydrazide moiety of this activated peptide is then reacted via the C-13 carbonyl group of MRA to yield MRA-PLGIIGG (SEQ ID NO:109), which is purified by preparative thin layer chromatography (TLC). The purified drug-linker intermediate is reacted at the succinic acid terminal with dicyclohexyl carbodiimide (DCC) and N-hydroxysuccinimide (NHS). This activated compound is again purified by TLC and then coupled to the lysine residues of TM by adding a 20-fold excess of MRA-PLGIIGG (SEQ ID NO:109) to purified TM at pH 8 for 3 hr. The TM used in this preparation is isolated from biological sources as described above. This conjugate is referred to as TM(bio)-MRA.

The conjugation reaction mixture is centrifuged to remove precipitated material and is applied to a column of Sephadex G-50 equilibrated with 50 mM sodium phosphate, 0.1 M NaCl (pH 7.0). The fractions containing TM(bio)-MRA conjugate are pooled and stored at 4° C. The drug-to-TM ratio is determined by spectrophotometry at 280 and 480 nm using extinction coefficients of 9.9 mM$^{-1}$ cm$^{-1}$ and 13 mM$^{-1}$ cm$^{-1}$, respectively. The conjugates are analyzed by HPLC on a Dupont GF-250 gel filtration column and by NaDodSO4/PAGE on 7.5% acrylamide gels under nonreducing conditions.

Anti-cancer drug attached to dimeric IgA via a scissile peptide and a pH-sensitive hydrazide linker. The activated drug linker compound, prepared as described above, is coupled to the lysine residues of dimeric IgA by adding a 20-fold excess of MRA-PLGIIGG (SEQ ID NO:109) to purified dIgA at pH 8 for 3 hr. The dIgA used in this preparation is isolated from biological sources as described above. This conjugate is referred to as dIgA-MRA.

The conjugation reaction mixture is centrifuged to remove precipitated material and is applied to a column of Sephadex G-50 equilibrated with 50 mM sodium phosphate, 0.1 M NaCl (pH 7.0). The fractions containing dIgA-PLGIIGG-MRA (SEQ ID NO:109) conjugate are pooled and stored at 4° C. The drug-to-dIgA ratio is determined by spectrophotometry at 280 and 480 nm using extinction coefficients of 9.9 mM$^{-1}$ cm$^{-1}$ and 13 mM$^{-1}$ cm$^{-1}$, respectively. The conjugates are analyzed by HPLC on a Dupont GF-250 gel filtration column and by NaDodSO$_4$/PAGE on 7.5% acrylamide gels under nonreducing conditions.

Fluorescent compound targeted for retention in the endoplasmic reticulum. The scissile peptide AIQDPRLFAEEKAVAD (SEQ ID NO:45) is prepared as described above to contain an amino terminal fluorescein and a free sulfhydryl from an additional cysteine at the carboxy terminal. TM (100 nmol) purified from transgenic insect cells as described above is reacted with sulfosuccinimidyl 4-[N-maleimidomethyl]cyclohexane-1-carboxylate (sulfo-SMCC, 10 µmol, Pierce product #22322) and purified as described above. The purified TM-SMCC in ~1 ml buffer is immediately reacted with the fluoresceinated peptide containing a free sulfhydryl group (10 µmol dissolved in 200 µl DMF) as described above. The derivatized TM is then purified from the reaction mixture by column chromatography (NAP-10 column, Pharmacia). The ER retention signal KDEL (SEQ ID NO:44) is synthesized as part of the TM core protein by phosphoramidite oligonucleotide coupling as described above and ligated into an insect expression vector to create pTM. The final compound is referred to as TM(kdel)-peptide-FL.

Anti-cancer drug targeted for retention in the endoplasmic reticulum. The activated drug linker compound, prepared as described above, is coupled to the lysine residues of TM by adding a 20-fold excess of MRA-PLGIIGG (SEQ ID NO:109) and purified as described above. The TM used in this preparation is isolated from transgenic insect cells. The ER retention signal KDEL (SEQ ID NO:44) is synthesized as part of the TM core gene by phosphoramidite oligonucleotide coupling as described above and ligated into an insect expression vector to create pTM. This conjugate is referred to as TM(KDEL)-MRA.

Fluorescent compound targeted to the nucleus. Two nuclear targeting sequences AAPKKKRKV (SEQ ID NO:100) and AAKRPAAIKKAGQAKKKK (SEQ ID NO:101) are synthesized with amino terminal fluorescein and an additional carboxy terminal cysteine as described above. TM (100 mmol) purified biological sources as described above is reacted with sulfo-SMCC and purified as described above. The purified TM-SMCC in ~1 ml buffer is immediately reacted with the fluoresceinated peptide containing a free sulfhydryl group (10 µmol dissolved in 200 µl DMF) as described above. The derivatized TM is then purified from the reaction mixture by column chromatography (NAP-10 column, Pharmacia). The final compound is referred to as TM-peptide(nuc)-FL. Control preparations are performed in identical fashion except the synthetic peptide linker has no targeting function: VAVQSAGTPASGS (SEQ ID NO:99).

Anti-cancer drug tethered to an antigen combining site. The linker peptide PLGIIGG (SEQ ID NO:109) is first coupled to MRA via the hydrazide as described above. In this procedure however the succinic anhydride step is omitted, yielding a peptide-MRA containing a free amino terminus. The purified drug-linker intermediate is reacted at the amino terminal with dicyclohexyl carbodiimide (DCC) and N-hydroxysuccinimide (NHS) and a 20-fold excess of diketone 1 (Wagner et al., Science 270:1797-1800, 1995). The 1,3-diketone 1 is synthesized as described in Wagner et al.

The diketone-peptide-MRA conjugate is reacted with the antigen combining site of antibody 38C2 (Wagner et al.) engineered to be covalently linked to TM. The engineering procedures to produce TM-38C2 are essentially as described above in Example 2C. mRNA derived from a cell line producing 38C2 antibody is isolated by established procedures. Specific linkers are employed to prime polymerase chain reactions resulting in amplification of the Fv-Cγ1 section, and the entire kappa chain in separate amplification reactions as described above.

The resulting heavy chain (Fv-C$_H$1)-TM:kappa hybrid antibody joined by disulfide bridges through the constant regions of heavy and light chains is purified as described above.

Reaction of the hybrid antibody with the diketone-peptide-MRA results in a stable vinylogous amide linkage between the diketone moiety and the epsilon amino group of a lysine residue in the binding pocket. The final compound is referred to as TM(38C2)-MRA.

Intestinal trefoil factor attached to TM via a carbohydrate linker. The porcine intestinal trefoil factor (ITF) is purified using a specific antibody as described (Suemori et al., Proc. Natl. Acad. Sci. USA 88:11017-11021, 1991). TM, synthesized as described above by peptide coupling and corresponding to the structure described in Table II E. #2 is linked to the enterokinase recognition sequence, (Asp)4-Lys (residues 3-7 of SEQ ID NO:26), by procedures described above. The recognition sequence is synthesized from a Gly-thioester resin support yielding a C terminal Gly-αCOSH after cleavage. The sequence is further modified to contain an amino terminal cysteine. The released peptide is coupled to TM by reaction of the thioester and the bromoacetyl functional groups. ITF is then derivatized to be reactive with sulfhydryl groups by reaction with sulfo-SMCC as described above. After purification, ITF-SMCC is coupled to the (Asp)4-Lys-TM (residues 3-7 of SEQ ID NO:26) and purified as described above. The reaction results in coupling of ITF to TM via a peptide linker which is a substrate for enterokinase associated with the apical surface of the intestinal epithelial barrier. The compound is referred to as TM-ITF.

Example 3

Intracellular Delivery of a Biological Agent

This example illustrates the use of a TM prepared as described in Example 2 for delivery of biological agents to epithelial cells.

A. Intracellular Colocalization of TM and HA Viral Protein and Neutralization of Virus Intracellular Co-localization of TM and HA. MDCK cells stably transfected with cDNA encoding the rabbit pIgR are cultured on nitrocellulose filters in microwell chambers (Millicell, Millipore, Bedford, Mass.). Confluent pIgR+ MDCK cell monolayer filters are infected with influenza virus (1 PFU per cell) via the apical surface for 60 minutes at 37° C. After 8 hours, equivalent ELISA titers of either anti-HA-TM or anti-HA is added to the lower compartment. Twenty-four hours after the addition of antibody, cells are detached with trypsin (0.25% in 0.02% EDTA) (JRH Biosciences, Lenexa, Kans.), cytocentrifuged onto glass slides, and fixed with acetone. Two-color immunofluorescence is used to detect HA glycoprotein and $C\alpha 3$ simultaneously. The slides are incubated with fluorescein-labeled goat anti-murine IgA (Southern Biotechnology Associates, Inc., Birmingham, Ala.) and after extensive washing with PBS, biotin-labeled murine IgG anti-HA-MAb (directed against a different epitope from the anti-HA and anti-HA-TM antibody added to the cells in culture) in 1% bovine serum albumin in phosphate-buffered saline (PBS) is added for 1 hour at room temperature. After the slides are washed in PBS, HA protein is detected with Texas Red-conjugated streptavidin (Fisher Biotech, Pittsburgh, Pa.).

Anti-HA-TM colocalizes with HA viral proteins as documented by two-color immunofluorescence by which identical microscopic fields are viewed through separate filters that discriminated the appropriate wavelengths. Compartments containing anti-HA-TM are green, while those containing HA proteins are red. In double exposures, cellular sites in which both anti-HA-TM and HA proteins are present appear yellow. These observations are consistent with the hypothesis that during epithelial transcytosis, specific anti-HA-TM antibody can interact with newly synthesized viral HA protein. It contrast, infected monolayers treated with specific anti-HA containing no TM do not demonstrate intracellular antibody localization since IgG sequences are not transported through the epithelium Influenza infected cells treated with irrelevant IgAs, including IgA anti-Sendai virus HN and IgA anti-dinitrophenol, do not stain for the presence of antibody, indicating that accumulation of intracellular anti-HA-TM is due to combination with viral protein and not a result of nonspecific interference of IgA transport by the viral infection. In addition, uninfected monolayers treated with specific anti-HA without TM do not demonstrate intracellular aggregation of antibody. Collectively, these studies document that in cells infected with virus, transport of specific anti-HA-TM but not irrelevant IgA or anti-HA without TM, is impeded, resulting in intracellular accumulation only of specific anti-HA-TM.

Neutralization of Virus. The following experiments demonstrate that anti-HA-TM can interact with intracellular HA proteins within infected epithelial cells in such a manner as to reduce viral titers. Confluent MDCK cells expressing the pIgR are infected with influenza virus as described above. Six hours later, equivalent ELISA titers of anti-HA, anti-HA-TM, or MOPC-315, an irrelevant murine IgA, or anti-Sendai virus HN MAbs was added to the lower chamber. In some experiments, anti-murine IgA, in an amount that is predetermined to effectively inhibit specific IgA from binding to and neutralizing virus as documented in ELISA and plaque reduction assays, was added to the apical chamber of some groups. After an additional 4 hours, the specific IgA was removed from the basal chamber and the basal surface of the cell layer is washed. Monolayers are then incubated for an additional 24 hours at 37° C., at which time the apical supernatants are removed. Cells are scraped off the filters into PBS and disrupted by three successive freeze-thaw cycles. Cellular debris is removed from the lysate by centrifugation. The apical supernatants and cell lysates are tested for virus by plaque assay in which samples are pretreated with 5 μg of trypsin (Gibco, Grand Island, N.Y.) to activate virus. Comparisons among groups in each experiment are made by one-way analysis of variance with Fisher's protected t test.

Mean virus titers are significantly reduced in both the supernatants and cell lysates of polarized epithelial monolayers treated with anti-HA-TM compared with those from monolayers receiving anti-HA without TM. IgA anti-Sendai virus HN does not reduce influenza virus titers nor does an irrelevant IgA, MOPC-315. In addition, high titers of anti-IgA added to the apical surface of the cells does not reduce the ability of anti-HA-TM to neutralize the virus demonstrating that the neutralization is occurring inside the epithelial cell and is not the result of anti-HA-TM accumulating in the apical supernatant.

B. Delivery of Genes to Epithelial Cells Using TM-Polylysine

Cells and cell culture. Human colonic carcinoma (HT29) cells are cultured as described by Chintalacharuvu et al., *J. Cell. Physiol.* 148:35-47, 1991, and maintained in RPMI Media 1640. Human tracheal epithelial cells are harvested from necropsy specimens less than 24 hours postmortem and cultured as described by Ferkol et al., *J. Clin. Invest.* 92:2394-2400, 1993. Cells are grown on collagen gel matrices or on uncoated plates. Transfections are performed when the cells are 50 to 95% confluent. Viability of cells is determined by trypan blue exclusion.

DNA delivery to cells. Four days before transfection, the HT29 cells are washed twice with PBS, pH 7.4. Half of the cells are returned to RPMI Media 1640, and the remaining half are grown in Leibovitz L15 Media, a glucose-deficient culture medium. Human gamma interferon, 100 U/ml, is added to half of the cells grown in glucose-deficient media 2 days before transfection. Transfer of HT29 cells to glucose-free media increases expression of pIgR, as does treatment with human gamma interferon. Cell density is approximately $5 \times 10^4$ cells per plate at the time of transfection. Growth medium is changed and the cells are washed with PBS. Solutions containing TM-polylysine-DNA complex (2.5 μmol DNA noncovalently bound to 10, 20, 40, or 80 μmol TM), polylysine-DNA complex (2.5 μmol DNA complexed with 1.2 nmol polylysine), TM-polylysine (80 μmol) alone, or 2.5 μmol (20 μg) DNA alone, are added to individual plates. Each sample is filtered prior to transfection of cells. After the cells are incubated for 48 hours at 37° C., either in vitro or in situ, β-galactosidase assays are performed.

When primary cultures of human tracheal epithelial cells are 50% confluent, cells are washed once with PBS, pH 7.4, and the media is changed immediately before transfection. The conjugate-DNA complex, containing 10 μg (~1.3 pmol) plasmid, is applied and permitted to remain on the cells for 48 hours. The cells are then either harvested for protein extraction or fixed for in situ β-galactosidase assays.

Assays for β-galactosidase activity. The cells are washed in cold phosphate buffer once, then scraped from the plate in a solution consisting of 10 mM Tris, pH 7.5, 150 mM NaCl, and 1 mM EDTA. Centrifuged at 10,000 rpm for 1 minute, the cell pellets are resuspended in 100 μl 250 mM Tris, pH 7.8, and lysed by repeated freezing and thawing. Aliquots of the supernatant are assayed for protein content, and samples of supernatants containing equal amounts of protein are incubated at 37° C. for 12 hours with 520 mg ONPG as described by Lim and Chase, *BioTechniques* 7:576, 1989. The optical density of the samples is measured at 420 nm.

Individual cells expressing β-galactosidase are also identified following incubation with X-gal as described by Lim and Chase. Briefly, the cells are fixed with a solution of 1% glutaraldehyde in PBS for 15 minutes, and then incubated with a solution containing 0.5% X-gal for 12 to 16 hours at either 22 or 37° C. Blue colored cells are identified by phase-contrast light microscopy. A minimum of 100 cells are counted to determine the percentage of cells expressing β-galactosidase.

Immunohistochemical staining of cells for pIgR. The expression of pIgR in human tracheal epithelial cells transfected with the plasmid PRSVZ is determined by indirect immunofluorescence. After in situ β-galactosidase staining, the cells are fixed with a solution containing 2% paraformaldehyde, 10 mM $NaIO_4$, 37 mM $Na_2HPO_4$, and 75 mm lysine, pH 6.2, for 2 hours. The cells are made permeable by treatment with PBS containing 0.1% (w/v) ovalbumin and 0.5% saponin, then incubated sequentially with rabbit anti-human SC and fluorescein conjugated goat anti-rabbit IgG. Both antibodies are diluted 1:100 in PBS containing 0.1% (w/v) ovalbumin and 0.5% saponin. Between each incubation, the cells are washed three times with PBS containing 0.1% (w/v) ovalbumin. The stained cells are examined by fluorescence microscopy.

Expression of β-galactosidase in epithelial cells. Immunohistochemical evaluation and measurement of β-galactosidase activity is used to assess delivery of functional vector sequences to epithelial cells. The percentage of cells expressing β-galactosidase is comparable to the percentage of cells that express pIgR.

In general, the results demonstrate that expression plasmids noncovalently bound to TM-polylysine can be introduced efficiently into epithelial cells. Delivery is specific for cells that express pIgR, since human tracheal epithelial cells grown on plastic, a condition that down-regulates the expression of the receptor, fail to express the reporter gene whereas cells from the same trachea maintained on collagen gels can be transfected. The transfection of HT29 cells is also dependent on the level of expression of pIgR, since cells grown in conditions that up-regulate the receptor express the reporter gene more than cells grown in undifferentiated conditions. Competition for the pIgR with dimeric IgA in a fourfold molar excess blocks the delivery of the complex, indicating that the binding site(s) on the pIgR for dimeric IgA and TM-polylysine overlap. Uptake is not due to a non-specific increase in pinocytosis secondary to the presence of the TM-polylysine in the culture medium since the addition of TM-polylysine with uncomplexed DNA or the carrier-DNA complex after dissociation with DTT does not result in an increase in reporter gene expression. Moreover, the use of complexes with Fab fragments from irrelevant antibodies does not permit the uptake and expression of the reporter gene. Thus, the uptake and expression of the reporter gene is mediated by the specific interaction of the TM-polylysine with pIgR.

C. Protection Against Pseudomembranous Colitis in Mice Using Anti-*C. Difficile*-TM.

*C. difficile* strain VPI 10463 (referred to as VPI) is grown in brain-heart infusion (BHI) broth (Difco Laboratories, Detroit, Mich.). For plate counts, samples are homogenized, serially diluted, and plated on BHI agar. Colony counting is performed after incubation at 37° C. for 2 days. The toxin A preparation is obtained by using *C. difficile* grown within a dialysis bag in flasks containing autoclaved BHI. Flasks are incubated for 4 days at 37° C. in an anaerobic chamber. Toxin A is purified as described previously. The purified toxin gives a single band in polyacrylamide gel electrophoresis and Western immunoblot analysis and has a molecular mass of 400 kDa.

C3He/J axenic adult mice are reared in a Trexler-type isolator fitted with a rapid transfer system (La Calhone, Vdlizy, France) and fed a rodent diet (RO340, UAR, Villemoisson, France) ad libitum. All materials used for the mice are sterilized by heat or gamma irradiation.

Pseudomembranous cecitis is induced as follows. Axenic mice are inoculated through the orogastric route with 1 ml of a 24-hour culture of *C. difficile* VPI (ca. 104 vegetative cells per ml). Under these conditions, mice developed a disease characterized by an intense cecal abrasion together with a severe inflammatory process. All the animals die within 2 days. For passive protection studies, ascites fluids diluted 1:3 are injected intravenously (0.2 ml at the eye orbital sinus) into axenic mice. Three days later, serum samples are collected, and mice are challenged with toxinogenic *C. difficile* on day 4. Mortality is determined 2 days later. Surviving mice are killed on day 8 (4 days following challenge with the organism). Each cecum is weighed and homogenized in phosphate-buffered saline. Bacterial cells are counted, and supernatant fluids are analyzed for toxins A and B. Levels of serum antibodies to toxin A are estimated.

Ascites fluids are injected intravenously into axenic mice, and the stability of the antibodies in serum is examined by ELISA. Antibody titers remained high for at least 8 days, and the levels on day 8 are similar to those observed on day 3. Four days after the administration of ascites, mice are challenged with *C. difficile* VPI. The results show that mice injected with anti-C. diff-TM are protected against the disease (no mortality or diarrhea is observed). Analysis of fecal specimens showed that the protected mice contained similar levels of vegetative cells, toxin A, and toxin B. Toxin A levels are reduced in mice protected by anti-C. diff-TM compared with toxin A levels in dying untreated mice.

D. Delivery of Drugs and Fluorescent Compounds Attached to TM with Linkers

Delivery of a fluorescent compound attached to TM. Confluent $pIgR^+$ MDCK cell monolayer filters are incubated at the basolateral surface for twenty-four hours with TM-peptide-FL prepared as described above. Cells are then detached with trypsin (0.25% in 0.02% EDTA) (JRH Biosciences, Lenexa, Kans.), cytocentrifuged onto glass slides, and fixed with acetone. Fluorescence microscopy (491 nm excitation, 518 nm emission wavelengths) is used to detect the presence of fluorescein. Cells incubated with TM-peptide-FL yielded a detectable level of fluorescence whereas the control construct, containing a non-scissile peptide, had no detectable fluorescence.

Delivery of a fluorescent compound attached to dimeric IgA. Confluent $pIgR^+$ MDCK cell monolayer filters are incubated at the basolateral surface for twenty-four hours with dIgA-peptide-FL prepared as described above. Cells are then detached with trypsin (0.25% in 0.02% EDTA) (JRH Biosciences, Lenexa, Kans.), cytocentrifuged onto glass slides, and fixed with acetone. Fluorescence microscopy (491 nm excitation, 518 nm emission wavelengths) is used to detect the presence of fluorescein. Cells incubated with dIgA-peptide-FL yielded a detectable level of fluorescence whereas the control construct, containing a non-scissile peptide, had no detectable fluorescence.

Delivery to tumors of an anti-cancer drug linked to TM. The human colon carcinoma cell line HT-29 (expressing pIgR at its basolateral surface) is grown in RPMI tissue culture media supplemented with 10% fetal bovine serum (FBS). In vitro cell lines are used in establishing xenografts in nude mice. Eight to ten week old female athymic (nu/nu) mice (National Cancer Institute, Bethesda, Md.) are injected subcutaneously into the flank with cell suspensions taken from in vitro cultures. Each mouse receives a single injection of $2 \times 10^6$ cells to generate solid tumors. Tumor growth is followed by measurements in two perpendicular diameters. Measurements are made at periodic intervals to establish tumor growth time curves until animal death. Starting on day 3 after tumor inoculation groups of mice are treated with TM(bio)-MRA (prepared as described above; 100 µg in 200 µL sterile saline) by intraperitoneal injection. Control mice are treated with TM containing no doxorubicin.

Mice treated with TM(bio)-MRA showed a significant level of tumor suppression compared to the controls.

Delivery to tumors of an anti-cancer drug linked to dimeric IgA. Tumors are initiated as described above and growth is followed by measurements in two perpendicular diameters. Measurements are made at periodic intervals to establish tumor growth time curves until animal death. Starting on day 3 after tumor inoculation groups of mice are treated with dIgA-MRA (prepared as described above; 300 µg in 200 µL sterile saline) by intraperitoneal injection. Control mice are treated with TM containing no doxorubicin.

Mice treated with dIgA-MRA showed a significant level of tumor suppression compared to the controls.

Delivery to tumors of an anti-cancer drug linked to the antigen combining site of a hybrid antibody. Tumors are initiated as described above and growth is followed in two perpendicular diameters. Measurements are made at periodic intervals to establish tumor growth time curves until animal death. Starting on day 3 after tumor inoculation, groups of mice are treated with TM(382C2)-MRA (prepared as described above; 300 µg in 200 µL sterile saline) by intraperitoneal injection. Control mice are treated with TM(38C2)-MRA containing a non-scissile peptide (VAVQSAGTPASGS) (SEQ ID NO:99). Mice treated with TM(38C2)-MRA showed a significant level of tumor suppression compared to control mice.

Delivery of a fluorescent compound targeted for retention in the endoplasmic reticulum. Confluent pIgR+ MDCK cell monolayer filters are incubated at the basolateral surface for twenty-four hours with TM(kdel)-peptide-FL prepared as described above. Cells are then detached with trypsin (0.25% in 0.02% EDTA) (JRH Biosciences, Lenexa, Kans.), cytocentrifuged onto glass slides, and fixed with acetone. Fluorescence microscopy (491 nm excitation, 518 nm emission wavelengths) is used to detect the presence of fluorescein. Cells incubated with TM(kdel)-peptide-FL yielded a detectable level of fluorescence whereas the control construct, containing a non-scissile peptide, had no detectable fluorescence. Fluorescence is further localized to intracellular structures consistent with endomembrane organelles.

Delivery to tumors of anti-cancer drug targeted for retention in the endoplasmic reticulum. Tumors are initiated as described above and growth is followed by measurements in two perpendicular diameters. Measurements are made at periodic intervals to establish tumor growth time curves until animal death. Starting on day 3 after tumor inoculation groups of mice are treated with TM(KDEL)-MRA (prepared as described above; 300 µg in 200 µL sterile saline) by intraperitoneal injection. Control mice are treated with TM containing no doxorubicin.

Mice treated with TM(KDEL)-MRA showed a significant level of tumor suppression compared to the controls.

Delivery of a fluorescent compound to nuclei. MDCK cells stably transfected with cDNA encoding the rabbit pIgR are cultured on nitrocellulose filters in microwell chambers (Millicell, Millipore, Bedford, Mass.). Confluent pIgR+ MDCK cell monolayer filters are incubated with TM-peptide(nuc)-FL containing nuclear targeting sequences or the control TM-peptide-TR with no sequences, via the lower compartment. Twenty-four hours after the addition of TM, cells are detached with trypsin (0.25% in 0.02% EDTA) (JRH Biosciences, Lenexa, Kans.), cytocentrifuged onto glass slides, and fixed with acetone. Immunofluorescence is used to detect Texas Red.

TM-peptide(nuc)-FL localizes nuclei as documented by immunofluorescence. These observations indicate that during epithelial transcytosis, specific TM-peptide(nuc)-FL antibody can interact with cytoplasmic or endomembrane receptors and undergo transport to the nucleus. In contrast, infected monolayers treated with TM containing no nuclear targeting signal do not demonstrate nuclear fluorescence localization. These studies document that MDCK cells transport specific TM-peptide(nuc)-TR containing nuclear targeting sequences to the nucleus.

Delivery of the intestinal trefoil factor attached to TM via the enterokinase recognition sequence to the intestinal mucosa. Mice lacking intestinal trefoil factor are produced by targeted gene disruption as described (Mashimo et al., *Science* 274:262-265, 1996). To elicit mild colonic epithelial injury with ulceration, mice are given dextran sulfate sodium (DSS, 2.5% w/v) in their drinking water. After 1 day, mice are given a daily injection of 50 µg of TM-ITF, prepared as described above, by tail vein injection.

At nine days after the beginning of the DSS regimen, 50% of control mice develop bloody diarrhea and die. In contrast, only 5% of the TM-ITF treated mice develop bloody diarrhea. Inspection of the colons of control mice after DSS treatment demonstrates the presence of multiple stages of obvious ulceration and hemorrhage. In contrast, the colons of most of the TM-ITF treated mice are indistinguishable from mice receiving no DSS.

From the foregoing, it will be appreciated that, although specific embodiments of the invention have been described herein for the purpose of illustration, various modifications may be made without deviating from the spirit and scope of the invention.

SUMMARY OF SEQUENCE LISTING

SEQ ID NO: 1 is amino acid sequence of human J chain
SEQ ID NO:2 is amino acid sequence of mouse J chain
SEQ ID NO:3 is amino acid sequence of rabbit J chain
SEQ ID NO:4 is amino acid sequence of bovine J chain
SEQ ID NO:5 is amino acid sequence of bull frog J chain
SEQ ID NO:6 is amino acid sequence of earth worm J chain SEQ ID NO:7 is nucleotide sequence of "full length" TM cDNA (Table III)
SEQ ID NO:8 is nucleotide sequence of Core TM cDNA (Table IX)
SEQ ID NO:9 is nucleotide sequence of C2 fragment (Table V)
SEQ ID NO:10 is nucleotide sequence of D1.1 fragment (Table VI)
SEQ ID NO: 11 is nucleotide sequence of L3D fragment (Table VII)
SEQ ID NO: 12 is nucleotide sequence of T4 fragment (Table VIII)
SEQ ID NO:13 is nucleotide sequence of Core TM cDNA using L3 (Table X)
SEQ ID NO: 14 is nucleotide sequence of L3 fragment (Table VII.A)
SEQ ID NO: 15 is nucleotide sequence of DL fragment (Table VI.A)
SEQ ID NO: 16 is nucleotide sequence of TpS2 (Table XI)
SEQ ID NO: 17 is amino acid sequence of "full length" TM cDNA (Table III)
SEQ ID NO: 18 is amino acid sequence of Core TM cDNA (Table IX)
SEQ ID NO: 19 is amino acid sequence of C2 fragment (Table V)
SEQ ID NO:20 is amino acid sequence of D1.1 fragment (Table VI)
SEQ ID NO:21 is amino acid sequence of L3D fragment (Table VII)
SEQ ID NO:22 is amino acid sequence of T4 fragment (Table VIII)
SEQ ID NO:23 is amino acid sequence of Core TM cDNA using L3 (Table X)
SEQ ID NO:24 is amino acid sequence of L3 fragment (Table VII.A)
SEQ ID NO:25 is amino acid sequence of D1 fragment (Table VI.A)
SEQ ID NO:26 is amino acid sequence of TpS2 (Table XI)
SEQ ID NO:27 is complementary nucleotide sequence of "full length" TM cDNA (Table III)
SEQ ID NO:28 is complementary nucleotide sequence of Core TM cDNA (Table IX)
SEQ ID NO:29 is complementary nucleotide sequence of C2 fragment (Table V)
SEQ ID NO:30 is complementary nucleotide sequence of D1.1 fragment (Table VI)
SEQ ID NO:31 is complementary nucleotide sequence of L3D fragment (Table VII)
SEQ ID NO:32 is complementary nucleotide sequence of T4 fragment (Table VIII)
SEQ ID NO:33 is complementary nucleotide sequence of Core TM cDNA using L3 (Table X)
SEQ ID NO:34 is complementary nucleotide sequence of L3 fragment (Table VII.A)
SEQ ID NO:35 is complementary nucleotide sequence of D1 fragment (Table VI.A)
SEQ ID NO:36 is complementary nucleotide sequence of TpS2 (Table XI)
SEQ ID NO:37 is Domain 1, 13 amino acid peptide with substantial α-sheet character
SEQ ID NO:38 is peptide recognized by the tobacco etch virus protease Nia
SEQ ID NO:39 is amino acid residues from pro-cathepsin E
SEQ ID NO:40 is linker from procathepsin
SEQ ID NO:41 is linker from polyimmunoglobulin receptor
SEQ ID NO:42 is nucleotide sequence of secretion signal from pMelBac
SEQ ID NO:43 is amino acid sequence of secretion signal from pMelBac
SEQ ID NO:44 is endomembrane retention signal
SEQ ID NO:45 is residues 585-600 of polyimmunoglobulin receptor (human)
SEQ ID NO:46 is Oligonucleotide 1
SEQ ID NO:47 is Oligonucleotide 2
SEQ ID NO:48 is Oligonucleotide 1.1
SEQ ID NO:49 is Oligonucleotide 2.1
SEQ ID NO:50 is Oligonucleotide 1.2ser
SEQ ID NO:51 is Oligonucleotide 2.2ser
SEQ ID NO:52 is Oligonucleotide 1.2val
SEQ ID NO:53 is Oligonucleotide 2.2val
SEQ ID NO:54 is Oligonucleotide 3
SEQ ID NO:55 is Oligonucleotide 4
SEQ ID NO:56 is Oligonucleotide 5
SEQ ID NO:57 is Oligonucleotide 5.3dg
SEQ ID NO:58 is Oligonucleotide 6
SEQ ID NO:59 is Oligonucleotide 6.5dg
SEQ ID NO:60 is Oligonucleotide 7
SEQ ID NO:61 is Oligonucleotide 8
SEQ ID NO:62 is Oligonucleotide 9
SEQ ID NO:63 is Oligonucleotide 9L3Δ
SEQ ID NO:64 is Oligonucleotide 10L3Δ
SEQ ID NO:65 is Oligonucleotide 9L3Δ KDEL
SEQ ID NO:66 is Oligonucleotide 10L3Δ KDEL
SEQ ID NO:67 is Oligonucleotide 9.2Δ3
SEQ ID NO:68 is Oligonucleotide 10.2Δ3
SEQ ID NO:69 is Oligonucleotide 9.3Δ3/ser68
SEQ ID NO:70 is Oligonucleotide 10.3Δ3/ser68
SEQ ID NO:71 is Oligonucleotide 9.3Δ3/val68
SEQ ID NO:72 is Oligonucleotide 10.3Δ3/val68
SEQ ID NO:73 is Oligonucleotide 10
SEQ ID NO:74 is Oligonucleotide 10
SEQ ID NO:75 is Oligonucleotide 12
SEQ ID NO:76 is Oligonucleotide 13
SEQ ID NO:77 is Oligonucleotide 14
SEQ ID NO:78 is Oligonucleotide 15
SEQ ID NO:79 is Oligonucleotide 16
SEQ ID NO:80 is Oligonucleotide 15 KDEL
SEQ ID NO:81 is Oligonucleotide 16 KDEL
SEQ ID NO:82 is Oligonucleotide P1
SEQ ID NO:83 is Oligonucleotide P2
SEQ ID NO:84 is Fv heavy forward primer
SEQ ID NO:85 is Fv heavy back primer
SEQ ID NO:86 is Cα3 forward primer
SEQ ID NO:87 is Cα3 back primer
SEQ ID NO:88 is Fvκ forward primer
SEQ ID NO:89 is Fvκ back primer
SEQ ID NO:90 is nucleotide linker segment
SEQ ID NO:91 is nucleotide linker complement
SEQ ID NO:92 is nucleotide signal peptide
SEQ ID NO:93 is heavy chain forward primer
SEQ ID NO:94 is heavy chain back primer
SEQ ID NO:95 is kappa forward primer
SEQ ID NO:96 is kappa back primer
SEQ ID NO:97 is nucleotide heavy chain signal peptide
SEQ ID NO:98 is nucleotide light chain signal peptide
SEQ ID NO:99 is synthetic peptide linker
SEQ ID NO:100 is nuclear targeting sequence 1
SEQ ID NO:101 is nuclear target sequence 2
SEQ ID NO:102 is HDEL linker sequence for intracellular targeting
SEQ ID NO:103 is Oligonucleotide Tp1
SEQ ID NO:104 is Oligonucleotide Tp2
SEQ ID NO:105 is Oligonucleotide Tp3
SEQ ID NO:106 is Oligonucleotide Tp4

SEQ ID NO:107 is Oligonucleotide Tp5
SEQ ID NO:108 is Oligonucleotide Tp6
SEQ ID NO:109 is the substrate recognition sequence for matrix metalloproteinases
SEQ ID NO: 110 is linker from substrate recognition sequence for MMPs
SEQ ID NO:111 is the polyimmunoglobulin receptor from residues 601 to 630
SEQ ID NO:112 is a portion of human IgA1 CH2 region
SEQ ID NO: 113 is a scissile peptide recognized and bound by the anti-myc antibody.

The invention claimed is:

1. A composition for delivery of a biological agent to a basolateral factor of an epithelial surface, said composition comprising a targeting molecule covalently linked via a peptide bond to at least one biological agent, wherein said targeting molecule comprises a polypeptide that: (a) forms a closed covalent loop; and (b) contains at least three peptide domains having beta-sheet character, each of the domains being separated by domains lacking beta-sheet character, wherein said targeting molecule comprises the J chain portion encoded by nucleotides 1-213 of SEQ ID NO: 8 and wherein said biological agent is not native to the targeting molecule and is not iodine.

2. The composition of claim 1 wherein said targeting molecule contains at least four peptide domains having β-sheet character, separated by domains lacking β-sheet character.

3. The composition of claim 1 wherein said targeting molecule further comprises a linear N-terminal domain.

4. The composition of claim 3 wherein said N-terminal domain comprises an amino acid sequence selected from the group consisting of SEQ ID NOS:125, 126, 127, 128, 129, and Asn Lys.

5. The composition of claim 1 wherein said targeting molecule comprises the C-terminal domain of a J chain.

6. The composition of claim 5 wherein said C-terminal domain comprises a linear peptide having β-sheet character.

7. The composition of claim 6 wherein said linear peptide comprises an amino acid sequence selected from the group consisting of SEQ ID NOS:130, 131, 132, 133, and 134.

8. The composition of claim 5 wherein said C-terminal domain comprises a covalently closed loop.

9. The composition of claim 8 wherein said covalently closed loop comprises an amino acid sequence selected from the group consisting of SEQ ID NOS:135, 136, 137, 138, 139 and 140.

10. The composition of claim 1, wherein said biological agent is selected from the group consisting of enzymes, antibodies, single chain antigen binding proteins, antigen combining sites, nucleic acids, carbohydrates and lipids.

11. A pharmaceutical composition for delivery of a biological agent to a basolateral factor of an epithelial surface, comprising the composition of claim 1 and a pharmaceutically acceptable carrier.

12. The composition of claim 1, wherein said targeting molecule comprises an immunoglobulin heavy chain or portion thereof linked to said J-chain portion.

13. The composition of claim 1, wherein said targeting molecule does not comprise an immunoglobulin light chain.

14. The composition of claim 13, wherein said targeting molecule comprises an immunoglobulin heavy chain or portion thereof linked to said J-chain portion.

15. The composition of claim 1, wherein said targeting molecule does not contain at least one of the domains selected from $C_H1$, $C_H2\alpha$, $C_H3\alpha$ and $C_L$.

16. The composition of claim 15, wherein said targeting molecule contains at least four peptide domains having β-sheet character, separated by domains lacking β-sheet character.

17. The composition of claim 1, wherein said targeting molecule comprises the CH2 and CH3 domains of IgA or IgM but does not comprise a full-length immunoglobulin.

* * * * *

UNITED STATES PATENT AND TRADEMARK OFFICE
CERTIFICATE OF CORRECTION

PATENT NO. : 7,311,912 B1 Page 1 of 1
APPLICATION NO. : 09/005318
DATED : December 25, 2007
INVENTOR(S) : Hein et al.

It is certified that error appears in the above-identified patent and that said Letters Patent is hereby corrected as shown below:

Column 55,
Line 60: "substantial α-sheet" should read --substantial β-sheet--

Column 56,
Line 17: "5.3dg" should read --5.1dg--
Line 19: "6.5dg" should read --6.1dg--
Line 34: "SEQ ID NO:74 is Oligonucleotide 10" should read
--SEQ ID NO:74 is Oligonucleotide 11--

Column 116,
Line 36: "from $C_H 1$" should read --from $C_H 1\alpha$--

Signed and Sealed this

Third Day of June, 2008

JON W. DUDAS
*Director of the United States Patent and Trademark Office*